US012805696B2

(12) United States Patent
Mino et al.

(10) Patent No.: US 12,805,696 B2
(45) Date of Patent: Nov. 24, 2026

(54) AI-BASED ENDOSCOPIC TARGET IDENTIFICATION AND PROCEDURE PLANNING, INTER-FACILITY ENDOSCOPIC PROCEDURE PLANNING, AND RISK MANAGEMENT OF ADVERSE EVENTS IN ENDOSCOPY

(71) Applicant: Olympus Corporation, Tokyo (JP)

(72) Inventors: Hiroyuki Mino, Westborough, MA (US); Hirokazu Horio, Allentown, PA (US); Atanaska Gospodinova, Hamburg (DE); Gloria Yee, Wellesley, MA (US); Brandon Ranalli, Quincy, MA (US); Shintaro Inoue, Westborough, MA (US); Makoto Ishikake, Hachioji (JP); Shohei Hemmi, Tokyo (JP); Genri Inagaki, Fuchu (JP); Masayasu Chida, Yokohama (JP); Kenji Murakami, Hino (JP); Seiichiro Sakaguchi, Akishima (JP)

(73) Assignee: Olympus Corporation, Tokyo (JP)

( * ) Notice: Subject to any disclaimer, the term of this patent is extended or adjusted under 35 U.S.C. 154(b) by 80 days.

(21) Appl. No.: 18/314,398

(22) Filed: May 9, 2023

(65) Prior Publication Data

US 2026/0198756 A1 Jul. 16, 2026

Related U.S. Application Data

(60) Provisional application No. 63/364,564, filed on May 12, 2022, provisional application No. 63/364,437, (Continued)

(51) Int. Cl.
*A61B 1/00* (2006.01)
*A61B 34/10* (2016.01)
(Continued)

(52) U.S. Cl.
CPC .... *A61B 1/000096* (2022.02); *A61B 1/00006* (2013.01); *A61B 34/10* (2016.02); *A61B 17/22* (2013.01); *A61B 2034/301* (2016.02)

(58) Field of Classification Search
CPC .......... A61B 1/000096; A61B 1/00006; A61B 34/10; A61B 17/22; A61B 2034/301
See application file for complete search history.

(56) References Cited

U.S. PATENT DOCUMENTS 6,174,291 B1 * 1/2001 McMahon ........... A61B 5/0084 600/564
2017/0151027 A1 * 6/2017 Walker ................... A61B 34/37
(Continued)

FOREIGN PATENT DOCUMENTS

WO WO-2021193024 A1 * 9/2021

*Primary Examiner* — Kaitlyn E Sebastian
(74) *Attorney, Agent, or Firm* — Schwegman Lundberg & Woessner, P.A.

(57) ABSTRACT

Systems, devices, and methods for anatomical target identification and procedure planning in an endoscopic procedure are disclosed. An endoscopic system comprises a steerable elongate instrument to be positioned and navigated in a patient anatomy, and a processor. The processor can receive patient information including an image of an anatomical target, apply the image to a trained machine-learning (ML) model to identify the anatomical target and a characteristic thereof, and generate a treatment plan including a tool recommendation and operational parameters of the tool for use in a procedure to treat the anatomical target. The anatomical target characteristic and the treatment plan can be presented to a user as a procedure guidance, or used to robotically facilitate operation of the steerable elongate instrument or a treatment tool to treat the anatomical target.

20 Claims, 30 Drawing Sheets

Related U.S. Application Data filed on May 10, 2022, provisional application No. 63/364,453, filed on May 10, 2022.

(51) Int. Cl.

| | |
|---|---|
| *A61B 17/22* | (2006.01) |
| *A61B 34/30* | (2016.01) |

(56) References Cited

U.S. PATENT DOCUMENTS

| | | | | |
|---|---|---|---|---|
| 2018/0247153 | A1 * | 8/2018 | Ganapati | G06F 18/285 |
| 2020/0171327 | A1 * | 6/2020 | Levy | A61N 5/1048 |
| 2020/0297422 | A1 * | 9/2020 | Gocho | A61B 1/00055 |
| 2021/0038300 | A1 | 2/2021 | Bukesov et al. | |
| 2021/0038306 | A1 * | 2/2021 | McLoughlin | A61B 5/0084 |
| 2021/0121251 | A1 * | 4/2021 | Aljuri | G16H 20/40 |

* cited by examiner

AI-BASED ENDOSCOPIC TARGET IDENTIFICATION AND PROCEDURE PLANNING, INTER-FACILITY ENDOSCOPIC PROCEDURE PLANNING, AND RISK MANAGEMENT OF ADVERSE EVENTS IN ENDOSCOPY

CROSS REFERENCE TO RELATED APPLICATIONS

This application based upon and claims the benefit of priority from U.S. Provisional Patent Application Ser. No. 63/364,453, filed on May 10, 2022, U.S. Provisional Patent Application Ser. No. 63/364,437, filed on May 10, 2022, and U.S. Provisional Patent Application Ser. No. 63/364,564, filed on May 12, 2022, the entire contents of which are incorporated herein by reference.

CROSS REFERENCE TO RELATED APPLICATIONS

This application is related to commonly assigned U.S. Provisional Patent Application Ser. No. 63/263,711, entitled "IMAGE GUIDANCE DURING CANNULATION", filed on Nov. 8, 2021, U.S. Provisional Patent Application Ser. No. 63/263,715, entitled "PROCEDURE GUIDANCE FOR SAFETY", filed on Nov. 8, 2021, U.S. Provisional Patent Application Ser. No. 63/263,720, entitled "ENDOLUMINAL TRANSHEPATIC ACCESS PROCEDURE", filed on Nov. 8, 2021, U.S. Provisional Patent Application Ser. No. 63/263,732, entitled "AUTOMATIC POSITIONING AND FORCE ADJUSTMENT IN ENDOSCOPY", filed on Nov. 8, 2021, U.S. Provisional Patent Application Ser. No. 63/363,446, entitled "AUTOMATIC POSITIONING AND FORCE ADJUSTMENT IN ENDOSCOPY", filed on c, 2022, U.S. Provisional Patent Application Ser. No. 63/364,564, entitled "RISK MANAGEMENT OF ADVERSE EVENTS IN ENDOSCOPY", filed on May 12, 2022, U.S. Provisional Patent Application Ser. No. 63/364,566, entitled "AI-BASED ENDOSCOPIC TISSUE ACQUISITION PLANNING", filed on May 12, 2022, which are incorporated by reference in their entirety.

FIELD OF THE DISCLOSURE

The present document relates generally to endoscopic systems, and more particularly to systems and methods for computer-assisted anatomical target identification and endoscopic procedure planning using artificial intelligence.

BACKGROUND

Endoscopes have been used in a variety of clinical procedures, including, for example, illuminating, imaging, detecting and diagnosing one or more disease states, providing fluid delivery (e.g., saline or other preparations via a fluid channel) toward an anatomical region, providing passage (e.g., via a working channel) of one or more therapeutic devices or biological matter collection devices for sampling or treating an anatomical region, and providing suction passageways for collecting fluids (e.g., saline or other preparations), among other procedures. Examples of such anatomical region can include gastrointestinal tract (e.g., esophagus, stomach, duodenum, pancreaticobiliary duct, intestines, colon, and the like), renal area (e.g., kidney(s), ureter, bladder, urethra) and other internal organs (e.g., reproductive systems, sinus cavities, submucosal regions, respiratory tract), and the like.

Some endoscopes include a working channel through which an operator can perform suction, placement of diagnostic or therapeutic devices (e.g., a brush, a biopsy needle or forceps, a stent, a basket, or a balloon), or minimally invasive surgeries such as tissue sampling or removal of unwanted tissue (e.g., benign or malignant strictures) or foreign objects (e.g., calculi). Some endoscopes can be used with a laser or plasma system to deliver energy to an anatomical target (e.g., soft or hard tissue or calculi) to achieve desired treatment. For example, laser has been used in applications of tissue ablation, coagulation, vaporization, fragmentation, and lithotripsy to break down calculi in kidney, gallbladder, ureter, among other stone-forming regions, or to ablate large calculi into smaller fragments.

In conventional endoscopy, the distal portion of the endoscope can be configured for supporting and orienting a therapeutic device, such as with the use of an elevator. In some systems, two endoscopes can work together with a first endoscope guiding a second endoscope inserted therein with the aid of the elevator. Such systems can be helpful in guiding endoscopes to anatomic locations within the body that are difficult to reach. For example, some anatomic locations can only be accessed with an endoscope after insertion through a circuitous path.

Peroral cholangioscopy is a technique that permits direct endoscopic visualization, diagnosis, and treatment of various disorders of patient biliary and pancreatic ductal system using miniature endoscopes and catheters inserted through the accessory port of a duodenoscope. Peroral cholangioscopy can be performed by using a dedicated cholangioscope that is advanced through the accessory channel of a duodenoscope, as used in Endoscopic Retrograde Cholangio-Pancreatography (ERCP) procedures. ERCP is a technique that combines the use of endoscopy and fluoroscopy to diagnose and treat certain problems of the biliary or pancreatic ductal systems, including the liver, gallbladder, bile ducts, pancreas, or pancreatic duct. In ERCP, an cholangioscope (also referred to as an auxiliary scope, or a "daughter" scope) can be attached to and advanced through a working channel of a duodenoscope (also referred to as a main scope, or a "mother" scope). Typically, two separate endoscopists operate each of the "mother-daughter" scopes. Although biliary cannulation can be achieved directly with the tip of the cholangioscope, most endoscopists prefer cannulation over a guidewire. A tissue retrieval device can be inserted through the cholangioscope to retrieve biological matter (e.g., gallstones, bill duct stones, cancerous tissue) or to manage stricture or blockage in bile duct.

In ERCP, the duodenoscope can be passed through the mouth and esophagus and down to the duodenum, access the papilla of Vater in the duodenum. Contrast dyes can be injected through the papilla into the ductal system, and fluoroscopic images taken to show lesions, stones, strictures or blockages. One treatment involving the use of ERCP is sphincterotomy, which involves making a small cut in the papilla of Vater to enlarge the opening of the bile duct and/or pancreatic duct to improve the drainage or to remove biliary ductal calculi. Another ERCP treatment involves placing a stricture management device (e.g., a stent) in a blocked or narrowed duct portion to improve drainage or to facilitate passing a device therethrough. Yet another ERCP treatment is tissue acquisition, such as a biopsy to remove samples for pathology assessment.

Peroral cholangioscopy can also be performed by inserting a small-diameter dedicated endoscope directly into the bile duct, such as in a Direct PerOral Cholangioscopy (DPOC) procedure. In DPOC, a slim endoscope (cholangioscope) can be inserted into patient mouth, pass through the upper GI tract, and enter into the common bile duct for visualization, diagnosis, and treatment of disorders of the biliary and pancreatic ductal systems.

SUMMARY

The present disclosure recognizes several technological problems to be solved with conventional endoscopes, such as duodenoscopes used for diagnostics and retrieval of sample biological matter. One of such problems is increased difficulty in navigating endoscopes, and instruments inserted therein, to locations in anatomical regions deep within a patient. For example, in ERCP procedures, as the duodenoscope, the cholangioscope, and the tissue retrieval device become progressively smaller due to being inserted sequentially in progressively smaller lumens, it has become more difficult to maneuver and navigate the endoscope through the patient anatomy, maintain endoscope stabilization, and maintain correct cannulation position in a narrow space (e.g., the bile duct). It can also be difficult to maintain an appropriate cannulation angle due to limited degree of freedom in scope elevator. Cannulation and endoscope navigation require advanced surgical skills and manual dexterity, which can be particularly challenging for less-experienced operating physicians (e.g., surgeons or endoscopists).

The difficulty in cannulation and endoscope navigation may also be attributed to variability of patient anatomy, especially in patients with surgically altered or otherwise difficult anatomy. For example, in ERCP procedures, some patients may have altered anatomy to a portion of the GI tract or the pancreaticobiliary system (e.g., the ampulla). In some patients, stricture ahead of pancreas can compress the stomach and part of duodenum, making it difficult to navigate the duodenoscope in a limited lumen of the compressed duodenum and to navigate the cholangioscope to reach the duodenal papilla, the point where the dilated junction of the pancreatic duct and the bile duct (ampulla of Vater) enter the duodenum. In another example, some patients have alternated papilla anatomy. With the duodenoscope designed to be stable in the duodenum, it can be more difficult to reach the duodenal papilla in surgically altered anatomy.

Another identified problem of conventional endoscopy is the lack of continuous and in-vivo anatomical target identification. Conventional target identification is largely a manual approach, where a human observer (e.g., a surgeon) visualizes a target site and its surrounding environment through an endoscope. In case of a tight access to an operation site, the manual operation may lack accuracy due to limited surgical view, and it generally cannot provide immediate identification or characterization of the target matter (e.g., type and composition of a calculus). Biopsy techniques have been used to extract the target structure out of the body to analyze its composition in vitro. However, in many clinical applications, it is desirable to determine tissue composition in vivo to reduce surgery time and complexity and improve therapy efficacy. For example, in laser lithotripsy, automatic and in vivo identification and characterization of calculi (e.g., chemical composition of a kidney stone, a pancreobiliary stone, or a gallbladder stone) and distinguishing it from surrounding tissue would allow a physician to adjust a laser setting (e.g., power, exposure time, or firing angle) to apply proper laser energy to break apart or dust a calculous, while at the same time avoiding irradiating non-treatment tissue neighboring the target stone.

Conventional endoscopic laser therapy also has a limitation that tissue type or composition cannot be continuously monitored in a procedure. There are many moving parts during an endoscopic procedure, and the tissue viewed at from the endoscope may change throughout the procedure. Because the conventional biopsy techniques require the removal of a tissue sample to identify the composition, they cannot monitor the composition of the tissue throughout the procedure. Continuous monitoring and recognition of structure type (e.g., soft or hard tissue type, normal tissue versus cancerous tissue, or composition of calculi) at the tip of the endoscope may give physicians more information to better adapt the treatment during the procedure.

Another unmet need in endoscopy (and ERCP in particular) is automatic or computer-assisted identification or selection of proper tools or devices suitable for a particular type of endoscopic procedure, particularly in patients with surgically altered or otherwise difficult anatomy. For example, in endoscopic procedures for calculi management, ablation or fragmentation tools may include, for example, a mechanical lithotripsy device, a laser lithotripsy device, or an electrohydraulic lithotripsy device. Calculi removal tools may include, for example, a balloon, a basket, or a snare, among others. In endoscopic biopsy procedures, various tissue acquisition tools may be used, including, for example, a brush, a snare, forceps, or a suction device, among others. Conventionally, an operating physician (e.g., an endoscopist) may be required to take into consideration a multitude of factors, including size, characteristics, and location of the anatomical target, neighboring environment of the anatomical target, patient general health status and local conditions at the surgical site (e.g., tissue inflammation), to decide a proper tool or device for use in a procures. For certain patients especially those with surgically altered or otherwise difficult anatomy, identifying properties of an anatomical target of interest and choosing proper tools for use in treatment (e.g., calculi removal or tissue acquisition) can be challenging and time consuming, especially for inexperienced physicians. Conventional endoscopic systems generally lack the capability of automatic or computer-assisted treatment planning, including finding suitable tools or devices and recommending proper methods of operating such tools or devices in procedures for diagnostic imaging, stricture management, or tissue or calculi extraction, particularly in a limited or restricted surgical site.

The present disclosure can help solve these and other problems by providing systems, devices, and method for automated treatment planning in an endoscopic procedure such as ERCP. Artificial intelligence (AI) or machine learning (ML) may be used to facilitate anatomical target recognition, endoscope navigation, treatment tool or device selection, and computer-guided or robot-assisted maneuvering of the tools or devices, among other procedure planning tasks. According to one embodiment, an endoscopic system comprises a steerable elongate instrument configured to be positioned and navigated in a patient anatomy, and a processor. The steerable elongate instrument can include diagnostic or therapeutic endoscopes, cannulas, catheters, guidewires, or guide sheaths, among others. The processor can be configured to receive patient information including an image of an anatomical target, apply the image of the anatomical target to a trained machine-learning (ML) model to identify the anatomical target (e.g., soft tissue, hard tissue, or a calculi structure) and a characteristic thereof (e.g., type, size, location, hardness, or composition), and generate a treatment plan for treating the anatomical target. The treatment plan may include, among other parameters, a tool recommendation and operational parameters of the tool for use in a procedure to treat the anatomical target. The anatomical target characteristic and the treatment plan can be presented on a user interface as a peri-operative guidance to assist the operating physician during the procedure. In some examples, the system can include a controller configured to control an actuator to robotically facilitate an operation of the steerable elongate instrument or a treatment tool associated therewith (e.g., the recommended tool) to treat the anatomical target.

The AI-based anatomical target identification as described in this document allows for continuous monitoring of target properties (e.g., composition) throughout the procedure. In an example, the continuously monitored composition may be used as a feedback to automatically control laser output or to alert the user to manually adjust laser output. In an example, a machine learning (ML) model may be trained to recognize the anatomical target and to determine a proper setting of the laser system based on spectroscopic data of the anatomical target. By adapting the laser therapy to target type and composition, stone ablation or dusting procedure can be performed faster and in a more energy-efficient manner.

The AI-based procedure planning as described in this document (including tool recommendation and proper methods of operating the recommended tool) can improve endoscopic procedure accuracy and efficiency, particularly in patients with surgically altered or otherwise difficult anatomy. Compared to conventional manual procedure planning, the automated procedure planning as discussed in this document can help ease the burden and shorten the planning time, reduce variability of procedure outcome due to variations in experience and dexterity across the operating physicians, and improve the endoscopic procedure prognostic predictability. As a result, overall procedure efficiency, accuracy, patient safety, and endoscopic procedure success rate can be improved.

Example 1 is an endoscopic system, comprising: a steerable elongate instrument configured to be positioned and navigated in a patient anatomy; a processor configured to: receive patient information including an image of an anatomical target; and apply the received image of the anatomical target to at least one trained machine-learning (ML) model to (i) identify the anatomical target and a characteristic thereof, and (ii) generate a treatment plan for treating the anatomical target; and a user interface configured to present the identified characteristic of the anatomical target and the generated treatment plan to a user.

In Example 2, the subject matter of Example 1 optionally includes a controller circuit configured to generate a control signal to an actuator to robotically facilitate operation of the steerable elongate instrument or a treatment tool associated therewith to treat the anatomical target in accordance with the generated treatment plan.

In Example 3, the subject matter of any one or more of Examples 1-2 optionally includes the processor that can be configured to use the at least one trained ML model to identify the anatomical target as a calculi target, and to determine a characteristic including one or more of size, shape, hardness, or composition of the calculi target.

In Example 4, the subject matter of any one or more of Examples 1-3 optionally includes the processor that can be configured to use the at least one trained ML model to identify the anatomical target as a tissue target, and to determine a characteristic including one or more of inflammation status, level of stricture, or malignancy state of the tissue target.

In Example 5, the subject matter of any one or more of Examples 1-4 optionally includes the processor that can be configured to use the at least one trained ML model to generate the treatment plan including a recommended tool of a specific type or size for use in treating the anatomical target.

In Example 6, the subject matter of Example 5 optionally includes the anatomical target that can include a calculi target, and wherein the recommended tool includes one of a mechanical lithotripsy device, a laser lithotripsy device, or an electrohydraulic lithotripsy device for ablating or fragmenting the calculi target.

In Example 7, the subject matter of any one or more of Examples 5-6 optionally includes the recommended tool that can include one of a balloon, a basket, or a snare for extracting the anatomical target or a portion thereof.

In Example 8, the subject matter of any one or more of Examples 5-7 optionally includes the processor that can be configured to determine the recommended tool further based on one or more of: a position of the anatomical target; spatial restrictions of an environment of the anatomical target; or sizes or geometries of candidate tools for treating the anatomical target.

In Example 9, the subject matter of any one or more of Examples 5-8 optionally includes the generated treatment plan that can further include one or more operational parameters for using the recommended tool to treat the anatomical target.

In Example 10, the subject matter of Example 9 optionally includes the anatomical target that can include a calculi target, and wherein the one or more operational parameters include an energy output of a lithotripsy device for ablating or fragmenting the calculi target.

In Example 11, the subject matter of any one or more of Examples 9-10 optionally includes the one or more operational parameters that can include a position, a heading direction, or an angle of at least a portion of the recommended tool with respect to the anatomical target.

In Example 12, the subject matter of any one or more of Examples 9-11 optionally includes the one or more operational parameters that can include a navigation path for navigating the steerable elongate instrument or maneuvering the recommended tool with respect to the anatomical target.

In Example 13, the subject matter of any one or more of Examples 1-12 optionally includes the anatomical target that can include a calculi target, and wherein the processor is configured to use the at least one trained ML model to generate the treatment plan including a geometric location on the calculi target and an aiming angle or orientation of a laser lithotripsy device to direct laser energy at the geometric location to ablate or fragment the calculi target.

In Example 14, the subject matter of any one or more of Examples 1-13 optionally includes the anatomical target that can include a plurality of anatomical structures to be treated, and wherein the processor is configured to use the at least one trained ML model to generate the treatment plan including to determine an order of treating the plurality of structures.

In Example 15, the subject matter of any one or more of Examples 1-14 optionally includes the processor that can be configured to use the at least one trained ML model to determine a probability of success or an estimate of treatment time in accordance with the generated treatment plan.

In Example 16, the subject matter of any one or more of Examples 1-15 optionally includes the processor that can include a training module configured to train an ML model using a training dataset comprising procedure data from past endoscopic procedures on a plurality of patients, the procedure data including (i) images of anatomical targets of the plurality of patients and (ii) identified characteristics of the anatomical targets and assessments of treatment plans for treating respective anatomical targets.

In Example 17, the subject matter of Example 16 optionally includes the training module that can be configured to train the ML model using supervised learning or unsupervised learning.

In Example 18, the subject matter of any one or more of Examples 1-17 optionally includes the anatomical target that can include a plurality of targets, and wherein the user interface is configured to: display images of the plurality of targets; and responsive to a user selection of one of the plurality of targets, display the identified characteristic of the selected target and the generated treatment plan for treating the selected target.

Example 19 is a method of identifying an anatomical target and planning an endoscopic procedure via a endoscopic system, the method comprising: providing patient information including an image of the anatomical target; applying the image of the anatomical target to at least one trained machine-learning (ML) model to (i) identify the anatomical target and a characteristic thereof, and (ii) generate a treatment plan for treating the anatomical target; and presenting the identified characteristic of the anatomical target and the generated treatment plan on a user interface.

In Example 20, the subject matter of Example 19 optionally includes providing a control signal to an actuator to robotically facilitate operation of a steerable elongate instrument or a treatment tool associated therewith to treat the anatomical target in accordance with the generated treatment plan.

In Example 21, the subject matter of any one or more of Examples 19-20 optionally includes the identified target that can include a calculi target, and the identified characteristic includes one or more of size, shape, hardness, or composition of the calculi target.

In Example 22, the subject matter of any one or more of Examples 19-21 optionally includes the identified anatomical target that can include a tissue target, and the identified characteristic includes one or more of inflammation status, level of stricture, or malignancy state of the tissue target.

In Example 23, the subject matter of any one or more of Examples 19-22 optionally includes the generated treatment plan that can include a recommended tool of a specific type or size for use in treating the anatomical target.

In Example 24, the subject matter of Example 23 optionally include the recommended tool being determined further using one or more of: a position of the anatomical target; spatial restrictions of an environment of the anatomical target; or sizes or geometries of candidate tools for treating the anatomical target.

In Example 25, the subject matter of any one or more of Examples 23-24 optionally includes the generated treatment plan that can further include one or more operational parameters for using the recommended tool to treat the anatomical target.

In Example 26, the subject matter of Example 25 optionally includes the one or more operational parameters for using the recommended tool that can include: an energy output of a lithotripsy device for ablating or fragmenting a calculi target; a position, a heading direction, or an angle of at least a portion of the recommended tool with respect to the anatomical target; or a navigation path for navigating a steerable elongate instrument or maneuvering the recommended tool with respect to the anatomical target.

In Example 27, the subject matter of any one or more of Examples 19-26 optionally includes applying the image of the anatomical target to the at least one trained ML model to determine one or more of a probability of success or an estimate of treatment time in accordance with the generated treatment plan.

In Example 28, the subject matter of any one or more of Examples 19-27 optionally includes, via a training module, training an ML model using a training dataset comprising procedure data from past endoscopic procedures on a plurality of patients, the procedure data including (i) images of anatomical targets of the plurality of patient and (ii) identified characteristics of the anatomical targets and assessments of treatment plans for treating respective anatomical targets.

In Example 29, the subject matter of any one or more of Examples 19-28 optionally includes displaying images of the plurality of targets on the user interface; and responsive to a user selection of one of a plurality of targets, displaying the identified characteristic of the selected target and the generated treatment plan for treating the selected target.

The presented techniques are described in terms of health-related procedures, but are not so limited. This summary is an overview of some of the teachings of the present application and not intended to be an exclusive or exhaustive treatment of the present subject matter. Further details about the present subject matter are found in the detailed description and appended claims. Other aspects of the disclosure will be apparent to persons skilled in the art upon reading and understanding the following detailed description and viewing the drawings that form a part thereof, each of which are not to be taken in a limiting sense. The scope of the present disclosure is defined by the appended claims and their legal equivalents.

DETAILED DESCRIPTION

This document describes AI-based systems, devices, and methods for anatomical target identification and procedure planning in an endoscopic procedure. According to one embodiment, an endoscopic system comprises a steerable elongate instrument configured to be positioned and navigated in a patient anatomy, and a processor configured to receive patient information including an image of an anatomical target, apply the image of the anatomical target to a trained machine-learning (ML) model to identify the anatomical target and a characteristic thereof, and generate a treatment plan for treating the anatomical target. The treatment plan may include a tool recommendation and operational parameters of the tool for use in a procedure to treat the anatomical target. The anatomical target characteristic and the treatment plan can be presented to a user, or used to robotically facilitate operation of the steerable elongate instrument or a treatment tool associated therewith to treat the anatomical target.

Figure 1:
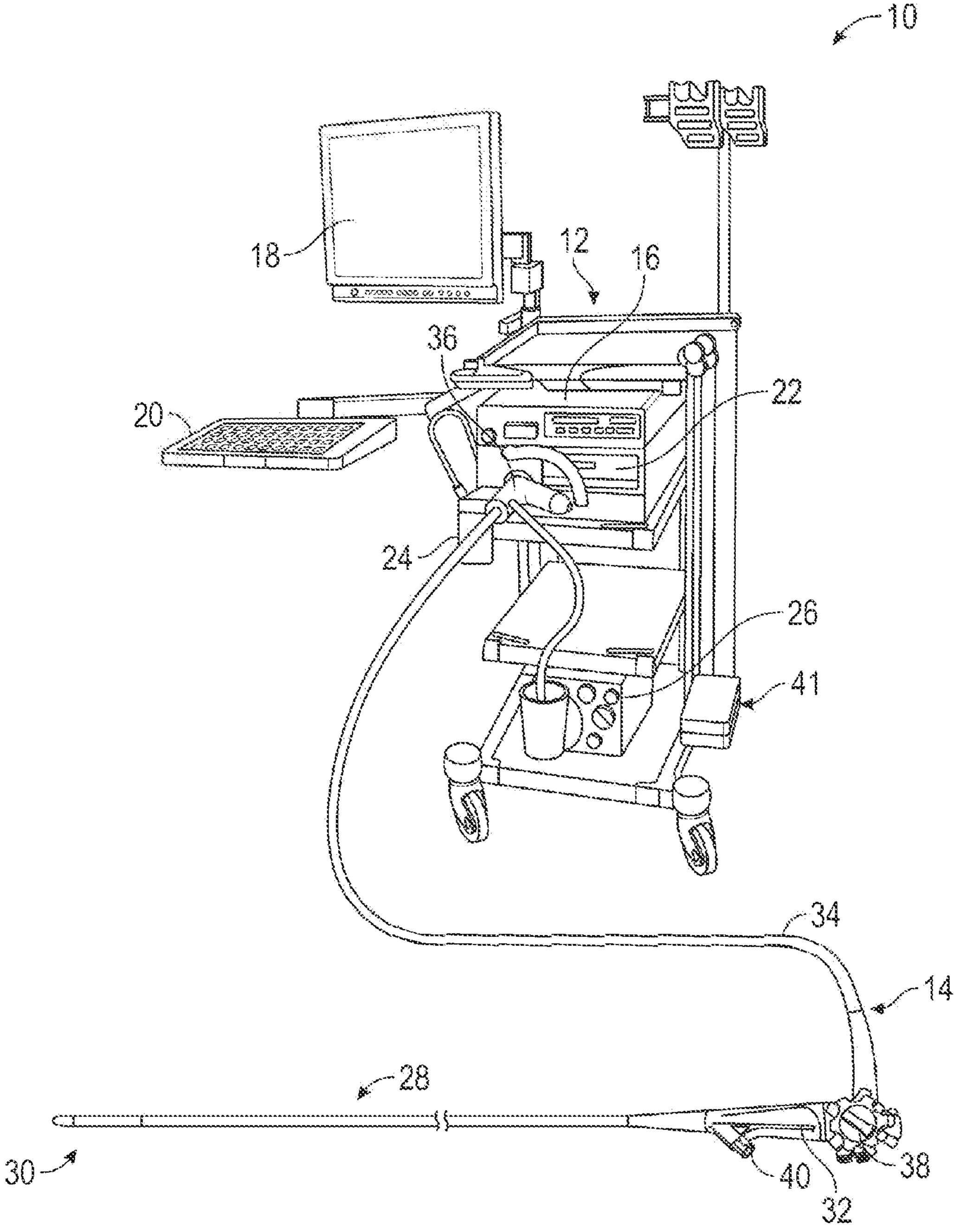
FIGS. 1-2 are schematic diagrams illustrating an example of an endoscopy system for use in endoscopic procedures such as an ERCP procedure.

FIG. 1 is a schematic diagram illustrating an example of an endoscopy system 10 for use in endoscopic procedures, such as an ERCP procedure. The system 10 comprises an imaging and control system 12 and an endoscope 14. The endoscopy system 10 is an illustrative example of an endoscopy system suitable for patient diagnosis and/or treatment using the systems, devices and methods described herein, such as tethered and optically enhanced biological matter and tissue collection, retrieval and storage devices and biopsy instruments that can be used for obtaining samples of tissue or other biological matter to be removed from a patient for analysis or treatment of the patient. According to some examples, the endoscope 14 can be insertable into an anatomical region for imaging and/or to provide passage of or attachment to (e.g., via tethering) one or more sampling devices for biopsies, or one or more therapeutic devices for treatment of a disease state associated with the anatomical region.

The imaging and control system 12 can comprise a control unit 16, an output unit 18, an input unit 20, a light source 22, a fluid source 24, and a suction pump 26. The imaging and control system 12 can include various ports for coupling with endoscopy system 10. For example, the control unit 16 can include a data input/output port for receiving data from and communicating data to the endoscope 14. The light source 22 can include an output port for transmitting light to the endoscope 14, such as via a fiber optic link. The fluid source 24 can comprise one or more sources of air, saline or other fluids, as well as associated fluid pathways (e.g., air channels, irrigation channels, suction channels) and connectors (barb fittings, fluid seals, valves and the like). The fluid source 24 can be in communication with the control unit 16, and can transmit one or more sources of air or fluids to the endoscope 14 via a port. The fluid source 24 can comprise a pump and a tank of fluid or can be connected to an external tank, vessel or storage unit. The suction pump 26 can comprise a port used to draw a vacuum from the endoscope 14 to generate suction, such as for withdrawing fluid from the anatomical region into which the endoscope 14 is inserted.

The output unit 18 and the input unit 20 can be used by a human operator and/or a robotic operator of endoscopy system 10 to control functions of endoscopy system 10 and view output of the endoscope 14. In some examples, the control unit 16 can additionally be used to generate signals or other outputs for treating the anatomical region into which the endoscope 14 is inserted. Examples of such signals or outputs can include electrical output, acoustic output, a radio-frequency energy output, a fluid output and the like for treating the anatomical region with, for example, cauterizing, cutting, freezing and the like.

The endoscope 14 can interface with and connect to the imaging and control system 12 via a coupler section 36. In the illustrated example, the endoscope 14 comprises a duodenoscope that may be use in a ERCP procedure, though other types of endoscopes can be used with the features and teachings of the present disclosure. The endoscope 14 can comprise an insertion section 28, a functional section 30, and a handle section 32, which can be coupled to a cable section 34 and the coupler section 36.

Figure 4A:
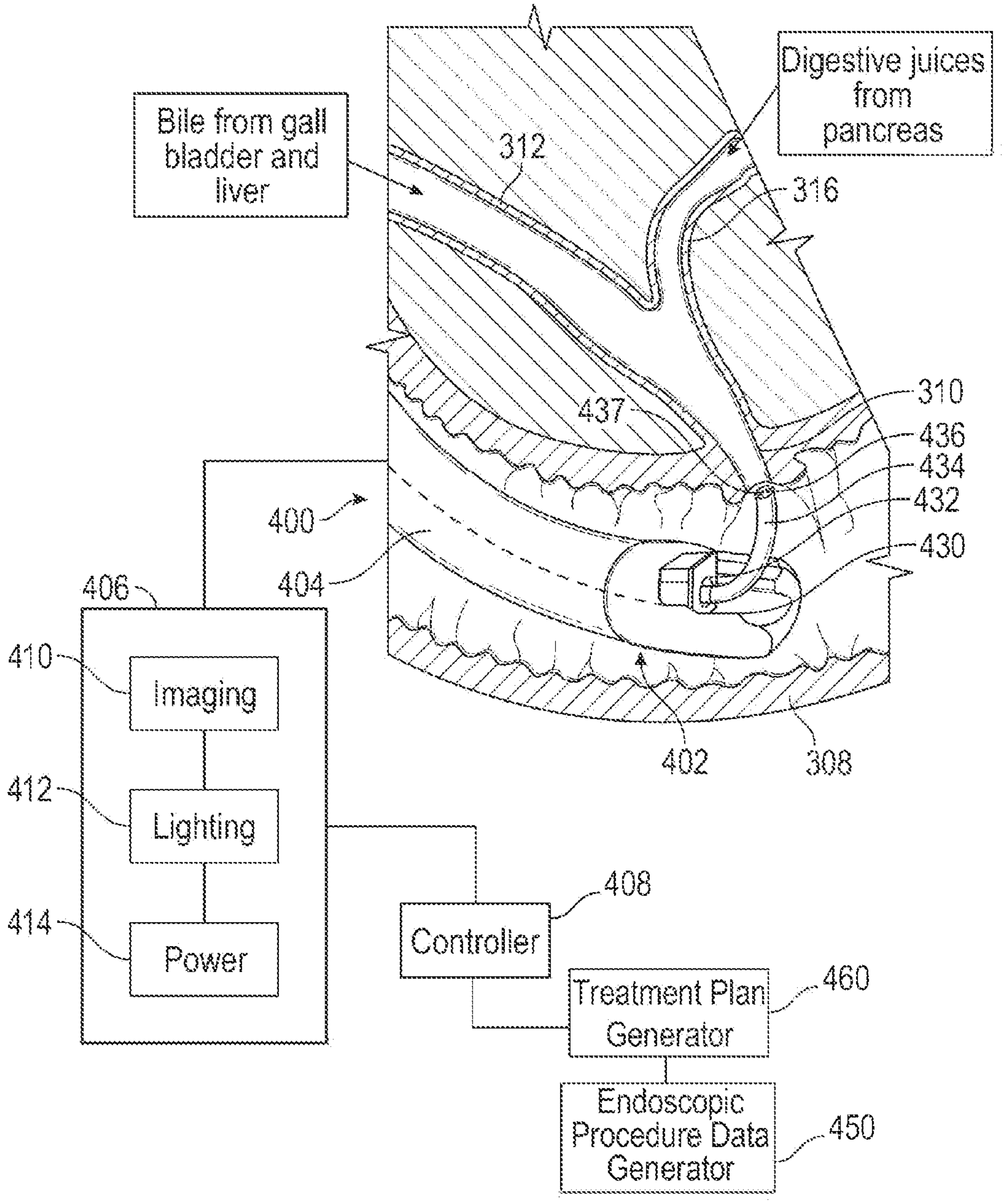
FIGS. 4A-4C are diagrams illustrating an example of mother-daughter endoscopes used in ERCP and a portion of patient anatomy of the procedure site, and endoscopic calculi treatment through ERCP.
Figure 4B:
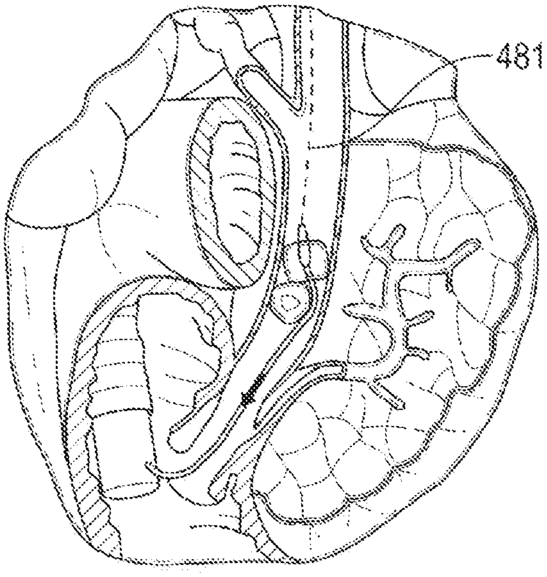
Figure 4C:
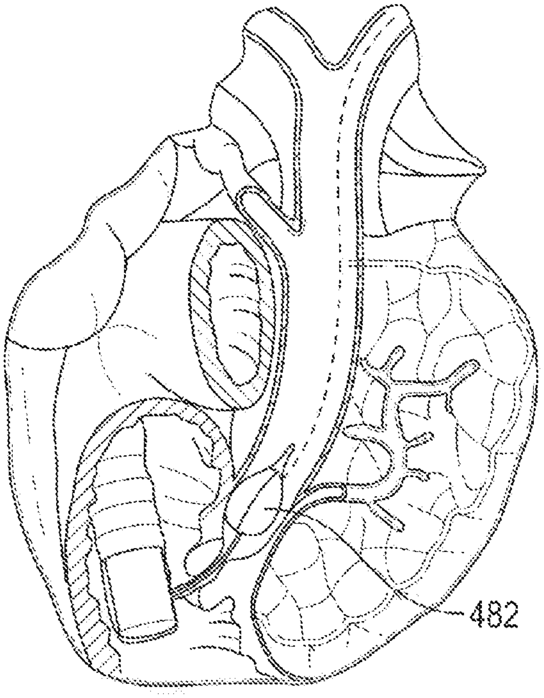

The insertion section 28 can extend distally from the handle section 32, and the cable section 34 can extend proximally from the handle section 32. The insertion section 28 can be elongate and include a bending section, and a distal end to which functional section 30 can be attached. The bending section can be controllable (e.g., by control knob 38 on the handle section 32) to maneuver the distal end through tortuous anatomical passageways (e.g., stomach, duodenum, kidney, ureter, etc.). Insertion section 28 can also include one or more working channels (e.g., an internal lumen) that can be elongate and support insertion of one or more therapeutic tools of functional section 30, such as a cholangioscope as shown in FIGS. 4A-4C. The working channel can extend between handle section 32 and functional section 30. Additional functionalities, such as fluid passages, guide wires, and pull wires can also be provided by insertion section 28 (e.g., via suction or irrigation passageways, and the like).

The handle section 32 can comprise a control knob 38 and ports 40. The ports 40 can be configured to couple various electrical cables, guide wires, auxiliary scopes, tissue collection devices of the present disclosure, fluid tubes and the like to handle section 32 for coupling with insertion section 28. The control knob 38 can be coupled to a pull wire, or other actuation mechanisms, extending through insertion section 28. The control knob 38 can be used by a user to manually advance or retreat the insertion section 28 of the endoscope 14, and to adjust bending of a bending section at the distal end of the insertion section 28. In some examples, an optional drive unit 46 (FIG. 2) can be used to provide motorized drive for advancing a distal section of endoscope 14 under the control of the control unit 16.

The imaging and control system 12, according to examples, can be provided on a mobile platform (e.g., cart 41) with shelves for housing light source 22, suction pump 26, image processing unit 42 (FIG. 2), etc. Alternatively, several components of the imaging and control system 12 shown in FIGS. 1 and 2 can be provided directly on the endoscope 14 such that the endoscope is "self-contained."

The functional section 30 can comprise components for treating and diagnosing anatomy of a patient. The functional section 30 can comprise an imaging device, an illumination device, and an elevator. The functional section 30 can further comprise optically enhanced biological matter and tissue collection and retrieval devices. For example, the functional section 30 can comprise one or more electrodes conductively connected to handle section 32 and functionally connected to the imaging and control system 12 to analyze biological matter in contact with the electrodes based on comparative biological data stored in the imaging and control system 12. In other examples, the functional section 30 can directly incorporate tissue collectors.

In some examples, the endoscope 14 can be robotically controlled, such as by a robot arm attached thereto. The robot arm can automatically, or semi-automatically (e.g., with certain user manual control or commands), via an actuator, position and navigate an instrument such as the endoscope 14 (e.g., the functional section 30 and/or the insertion section 28) in an anatomical target, or position a device at a desired location with desired posture to facilitate an operation on the anatomical target (e.g., to remove biliary ductal calculi using a basket, a balloon, or a snare). According to some examples, a controller can use artificial intelligence (AI) to determine cannulation and navigation parameters and/or tool operational parameters (e.g., position, angle, posture, force, and navigation path), and generate a control signal to the actuator of the robot arm to facilitate operation of such instrument or tools in accordance with the determined navigation and operational parameters in a robot-assisted procedure.

Figure 2:
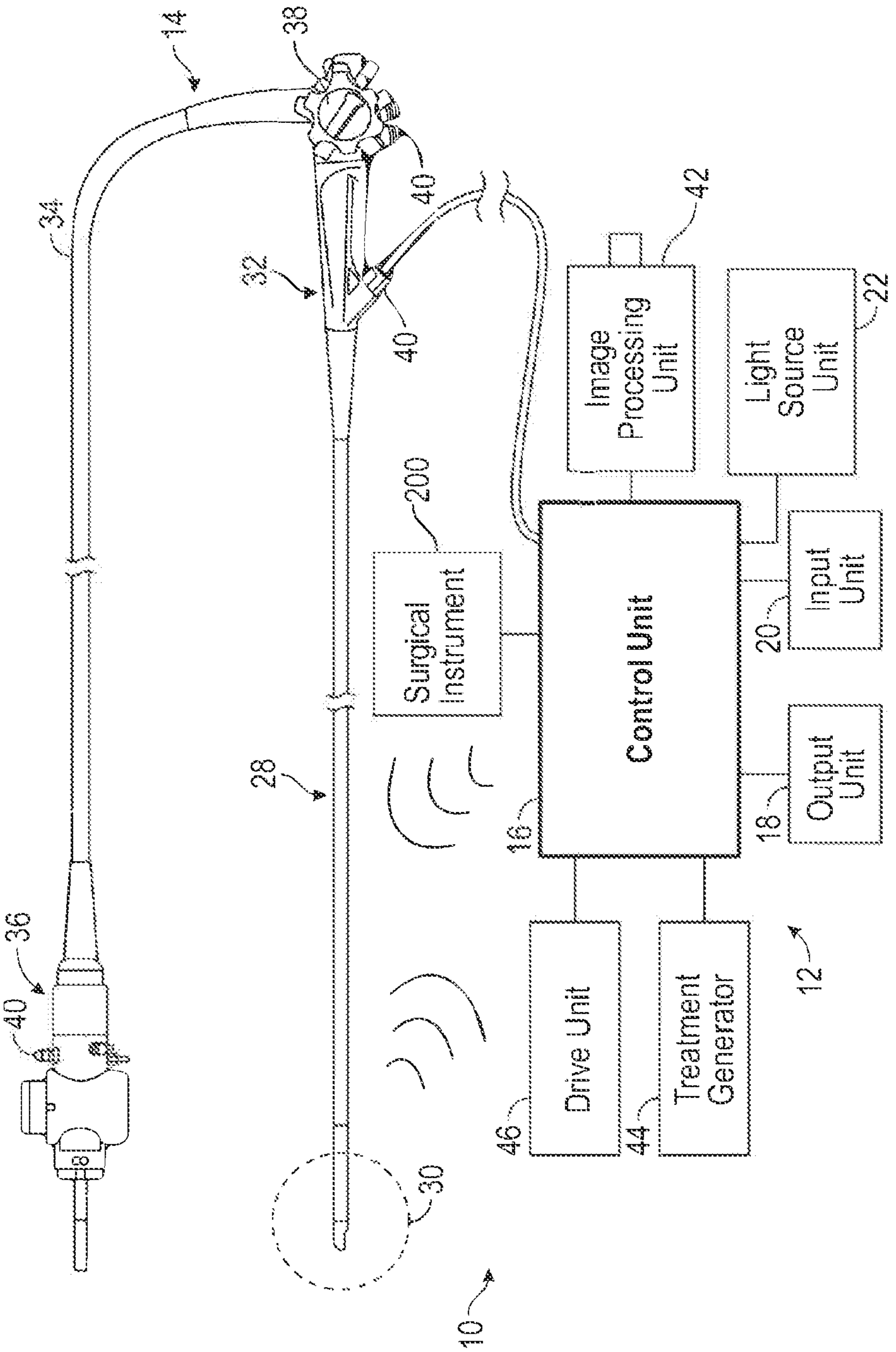

FIG. 2 is a schematic diagram of the endoscopy system 10 shown in FIG. 1, which comprises the imaging and control system 12 and the endoscope 14. FIG. 2 schematically illustrates components of the imaging and control system 12 coupled to the endoscope 14, which in the illustrated example comprises a duodenoscope. The imaging and control system 12 can comprise a control unit 16, which can include or be coupled to an image processing unit 42, a treatment generator 44, and a drive unit 46, as well as the light source 22, the input unit 20, and the output unit 18 as discussed above with reference to FIG. 1. The control unit 16 can comprise, or can be in communication with, a surgical instrument 200 comprising a device configured to engage tissue and collect and store a portion of that tissue and through which an imaging device (e.g., a camera) can view target tissue via inclusion of optically enhanced materials and components. The control unit 16 can be configured to activate an imaging device (e.g., a camera) at the functional section of the endoscope 14 to view target tissue distal of surgical instrument 200 and endoscopy system 10, which can be fabricated of a translucent material to minimize the impacts of the camera being obstructed or partially obstructed by the tissue retrieval device. Likewise, the control unit 16 can be configured to activate the light source 22 to shine light on the surgical instrument 200, which can include select components that are configured to reflect light in a particular manner, such as tissue cutters being enhanced with reflective particles.

The image processing unit 42 and the light source 22 can each interface with the endoscope 14 (e.g., at the functional section 30) by wired or wireless electrical connections. The imaging and control system 12 can accordingly illuminate an anatomical region using the light source 22, collect signals representing the anatomical region, process signals representing the anatomical region using the image processing unit 42, and display images representing the anatomical region on the output unit 18. The imaging and control system 12 can include the light source 22 to illuminate the anatomical region using light of desired spectrum (e.g., broadband white light, narrow-band imaging using preferred electromagnetic wavelengths, and the like). The imaging and control system 12 can connect (e.g., via an endoscope connector) to the endoscope 14 for signal transmission (e.g., light output from light source, video signals from the imaging device such as positioned at the distal portion of the endoscope 14, diagnostic and sensor signals from a diagnostic device, and the like).

The treatment generator 44 can generate a treatment plan, which can be provided with the operating physician as a guidance for maneuvering the endoscope 14 during an endoscopic procedure, or used by the control unit 16 to control the operation of the endoscope 14. In some examples, the treatment generator 44 can identify an anatomical target and a characteristic thereof, such as type, location, size, composition, among other characteristics. The treatment generator 44 can generate a treatment plan, including an identification of suitable tools for use in treating the anatomical target (e.g., calculi removal or tissue acquisition), methods of operating and navigating such tools and the endoscope 14 over which such tools are deployed, navigation paths for placing the tools to the treatment site or for retrieving the tools after the treatment, among other treatment or control parameters. The treatment generator 44 can generate the treatment plan using patient information including images of the anatomical target. Examples of the images can include endoscopic images, images from external imaging devices such as X-ray or fluoroscopy images, electrical potential map or an electrical impedance map, computer tomography (CT) images, magnetic resonance imaging (MRI) images obtained in Magnetic resonance cholangiopancreatography (MRCP), or acoustic images such as endoscopic ultrasonography (EUS) images, among others. In some examples, the treatment generator 44 can identify the anatomical target and determine proper tools for use in treating the anatomical target using artificial intelligence (AI) or machine learning (ML). The treatment plan can be presented to an operating physician (e.g., an endoscopist) as a guidance during the procedure. Additionally or alternatively, the treatment plan can be provided to a robotic system to facilitate a robot-assisted endoscopic procedure. Examples of AI-based anatomical target recognition and tool identification are discussed below with reference to FIGS. 5, 6, and 7A-7B.

Figure 3A:
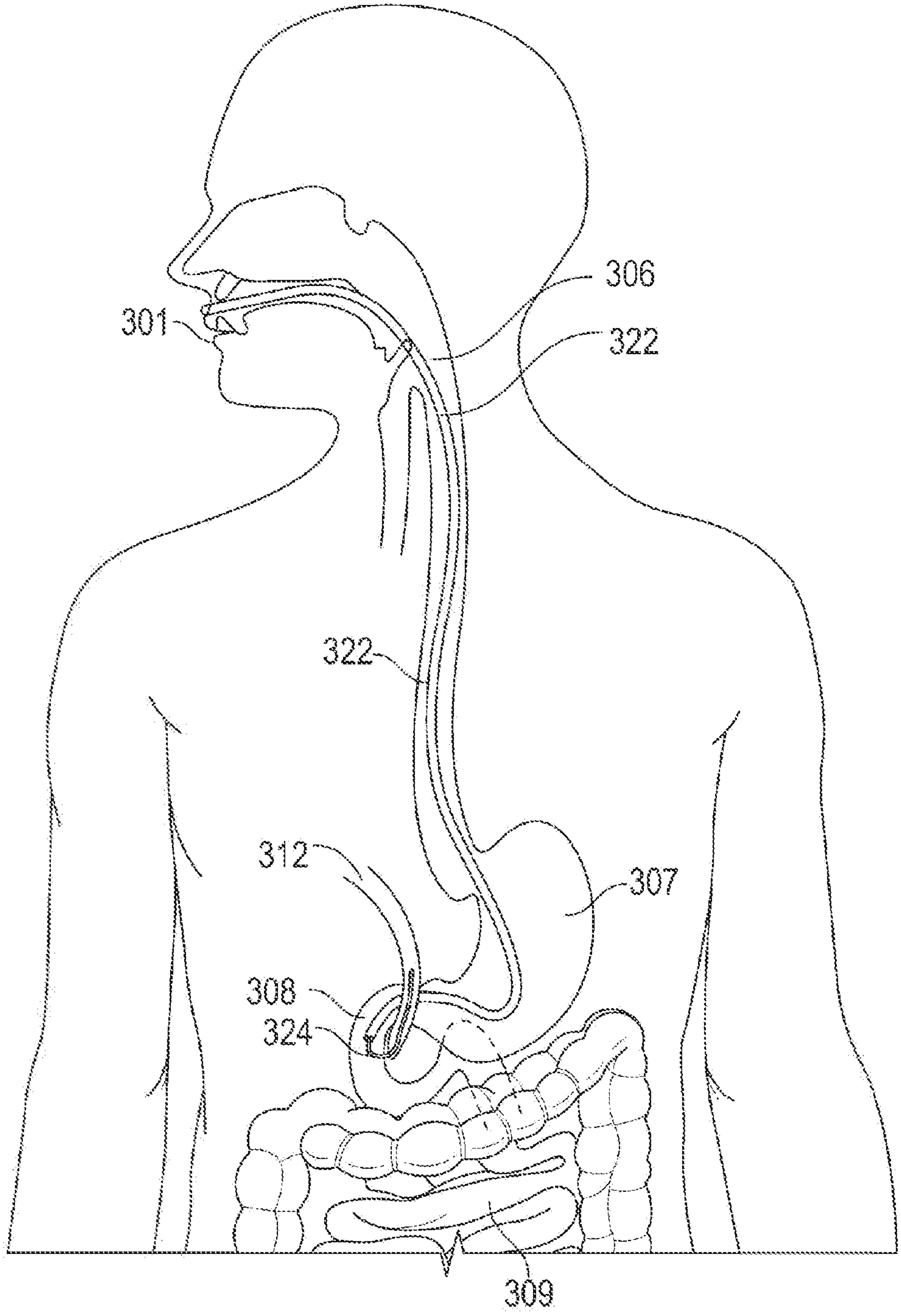
FIGS. 3A-3B are diagrams illustrating an example of peroral cholangioscopy involving direct insertion of a cholangioscope into patient bile duct as in a DPOC procedure, and a portion of patient anatomy where the procedure is performed.
Figure 3B:
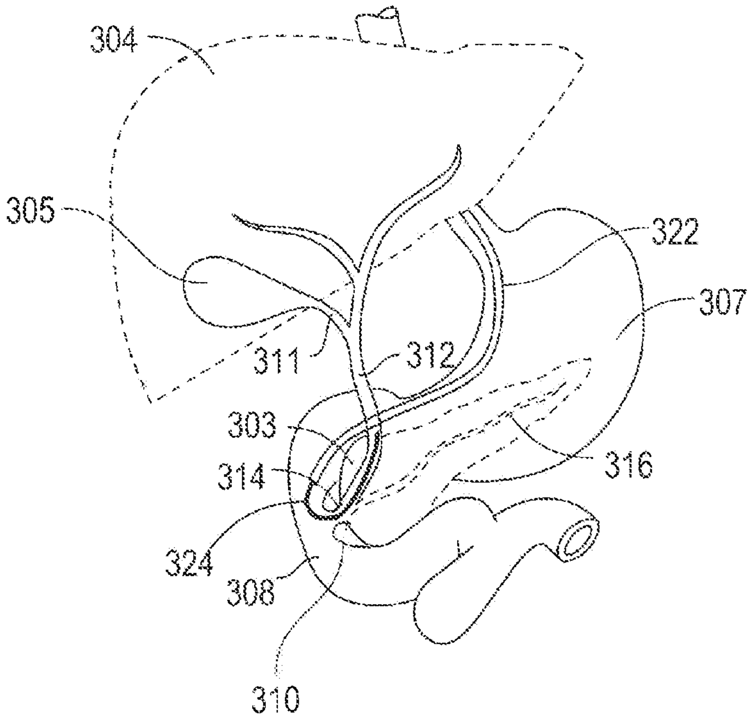

FIGS. 3A-3B are diagrams illustrating an example of peroral cholangioscopy performed via direct insertion of a cholangioscope 324 into the bile duct, as in a DPOC procedure, and a portion of patient anatomy where the procedure is performed. The cholangioscope 324 is nested inside of a guide sheath 322, and inserted perorally into a patient to reach duodenum 308. Duodenum 308 comprises an upper part of the small intestine. The guide sheath 322 can extend into mouth 301, through esophagus 306, through stomach 307 to reach the duodenum 308. Before reaching intestines 309, the guide sheath 322 can position the cholangioscope 324 proximate common bile duct 312. The common bile duct 312 carries bile from the gallbladder 305 and liver 304, and empties the bile into the duodenum 308 through sphincter of Oddi 310 (FIG. 3B). The cholangioscope 324 can extend from guide sheath 322 to extend into common bile duct 312. In some examples, steering features of guide sheath 322 (e.g., pull wire) can be used to facilitate navigating and bending of cholangioscope 324 through stomach 307, in addition to direct steering of cholangioscope 324 via the pull wires. For example, navigation of the Pyloric canal and Pyloric sphincter can be difficult to navigate using only an endoscope. Thus, the guide sheath 322 can be used to turn or bend elongate body of cholangioscope 324, or reduce the amount of steering or bending of the elongate body of the cholangioscope 324 required by pull wires, to facilitate traversing the Pyloric sphincter.

FIG. 3B is a schematic view of duodenum 308 connected to common bile duct 312 via duodenal papilla 314. Common bile duct 312 can branch off into pancreatic duct 316 and gallbladder duct 311. Duodenal papilla 314 can include sphincter of Oddi 310 that controls flow of bile and pancreatic juice into the intestine (duodenum). Pancreatic duct 316 can lead to pancreas 303. Pancreatic duct 316 carries pancreatic juice from pancreas 303 to the common bile duct 312. Gallbladder duct 311 can lead to gallbladder 305. In some patients, it can be difficult to navigate surgical instruments to duodenal papilla 314. It can also be difficult to navigate a surgical instrument into common bile duct 312 via insertion through duodenal papilla 314. Therefore, it is common during medical procedures to cut sphincter of Oddi 310 to enlarge duodenal papilla 314 to allow for easier access of instrument into common bile duct 312.

FIGS. 4A-4C are diagrams illustrating an example of mother-daughter endoscopes used in ERCP and a portion of patient anatomy of the procedure site, and endoscopic calculi treatment through ERCP. As illustrated in FIG. 4A, the mother-daughter endoscopes comprise an auxiliary scope 434 (cholangioscope) attached to and advanced through a lumen 432 of a main scope 400 (duodenoscope). The auxiliary scope 434 can comprise a lumen 436. The distal portion of the main scope 400 positioned in duodenum 308 comprises a functional module 402, an insertion section module 404, and a control module 406. The control module 406 can include, or be coupled to, a controller 408. Similar to the discussion above with respect to FIG. 1, the control module 406 can include other components, such as those described with reference to endoscopy system 10 (FIG. 1) and control unit 16 (FIG. 2). Additionally, the control module 406 can comprise components for controlling an imaging device (e.g., a camera) and a light source connected to the auxiliary scope 434, such as an imaging unit 410, a lighting unit 412 and a power unit 414. The main scope 400 can be configured similarly as endoscope 14 of FIGS. 1 and 2.

The functional module 402 of the main scope 400 can comprise an elevator portion 430. The auxiliary scope 434 can itself include functional components, such as camera lens 437 and a light lens (not illustrated) coupled to control module 406, to facilitate navigation of the auxiliary scope 434 from the main scope 400 through the anatomy and to facilitate viewing of components extending from lumen 432.

In ERCP, the auxiliary scope 434 can be guided into the sphincter of Oddi 310. Therefrom, a surgeon operating the auxiliary scope 434 can navigate the auxiliary scope 434 through the lumen 432 of the main scope toward the gallbladder 305, liver 304, or other locations in the gastrointestinal system to perform various procedures. In some examples, the auxiliary scope 434 can be used to guide an additional device to the anatomy to obtain biological matter (e.g., tissue), such as by passage through or attachment to lumen 436.

The biological sample matter can be removed from the patient, typically by removal of the additional device from the auxiliary device, so that the removed biological matter can be analyzed to diagnose one or more conditions of the patient. According to several examples, the mother-daughter endoscope assembly (including the main scope 400 and the auxiliary scope 434) can include additional device features, such as forceps or an auger, for gathering and removing cancerous or pre-cancerous matter (e.g., carcinoma, sarcoma, myeloma, leukemia, lymphoma and the like), or performing endometriosis evaluation, biliary ductal biopsies, and the like.

The controller 408 can include, or be coupled to, an endoscopic procedure data generator 450, and a treatment plan generator 460. The endoscopic procedure data generator 450 can generate images of an anatomical target, such as calculi or tissue structures in biliary and pancreatic ductal system. In an example, the endoscopic procedure data generator 450 can generate real-time endoscope images of the anatomical target and its surrounding environment using an imaging sensor on the endoscope, such as a camera located at the functional section 30 of the endoscope 14. In some examples, the endoscopic procedure data generator 450 can receive images from external imaging devices, such as X-ray or fluoroscopy images, electrical potential map or an electrical impedance map, CT scans, MRI scans such as obtained in MRCP, or acoustic images such as EUS images, among others. The endoscopic procedure data generator 450 may additionally generate or receive other procedure-related information, including sensor information (e.g., sensors associated with the endoscope or with a treatment device passing through the endoscope), device information, patient medical history etc. In some examples, the endoscopic procedure data generator 450 can retrieve, such as from a database, stored control log data (e.g., time-series data) of past endoscopic procedures performed by a plurality of physicians on a plurality of patients. The control log data can represent preferred cannulation and endoscope navigation approaches and habits of physicians with different experience levels.

The treatment plan generator 460, which is an example of the treatment generator 44 as illustrated in FIG. 2, can automatically generate a treatment plan based on images, among other information produced by the endoscopic procedure data generator 450. The treatment plan can include an identification of an anatomical target and properties thereof (e.g., type, location, size, composition), a tool recommendation and methods of operating the recommended tool in treating the anatomical target (e.g., removing calculi or extracting tissue), and a navigation path for advancing the tool or a retrieving path for extracting the anatomical target, among other treatment or control parameters. According to some examples, the treatment plan can be generated or updated using a trained machine-learning (ML) model. The images of the anatomical target and the treatment plan can be displayed to the operating physician as a procedure guidance. The treatment plan may also be used to robotically facilitate operation of the recommended tool or an endoscope in a robot-assisted procedure.

Various treatments can be performed through ERCP, including, for example, sphincterotomy, fragmentation and extraction of calculi, tissue acquisition or biopsy, and stent placement or balloon dilation for stricture management, among others. FIGS. 4B-4C are diagrams illustrating examples of endoscopic extraction of biliary ductal calculi in ERCP using different extraction tools, such as a balloon (FIG. 4B) or a basket (FIG. 4C). Guidewire may be placed to facilitate dilation (e.g., via a dilation ballonet) of the ampulla or stricture, sphincterotomy, or for use of wire guided instruments in both balloon-assisted or basket-assisted stone extraction. In FIG. 4B, a balloon catheter 481 is inserted into the common bile duct (CBD) via the wire-guided technique. The balloon catheter 481 has a lumen for contrast material, which can be injected via a hole above the balloon to facilitate balloon occlusion cholangiography. As the balloon catheter 481 is advanced into the CBD and passes the most distal stone, a stone retrieval balloon is inflated according to the CBD diameter. Under fluoroscopic guidance, the inflated balloon catheter 481 can then be pulled from the CBD into the lumen of the duodenum to expel the stone in its path. The same process can be repeated until complete stone clearance, which was confirmed by the cholangiography. In FIG. 4C, a basket catheter 482 can be inserted into the common bile duct (CBD) and passes the most distal stone. The basket catheter 482 has a lumen for contrast-material injection, allowing for visualization of stones during extraction. Under fluoroscopic guidance, a lithotripter basket is released and expanded to entrap the stone. The basket catheter 482 can be manipulated in a back-and-forth movement to capture the stone. The basket catheter 482 and the entrapped stone can then be retrieved without basket closure. The same process can be repeated until complete stone clearance.

According to various embodiments discussed in this document, an AI-based system can be used to automatically identify characteristics of the biliary ductal calculi during an ERCP procedure, generate a tool recommendation (e.g., a balloon or a basket) and methods of operating the recommended tool to remove the calculi.

Figure 5:
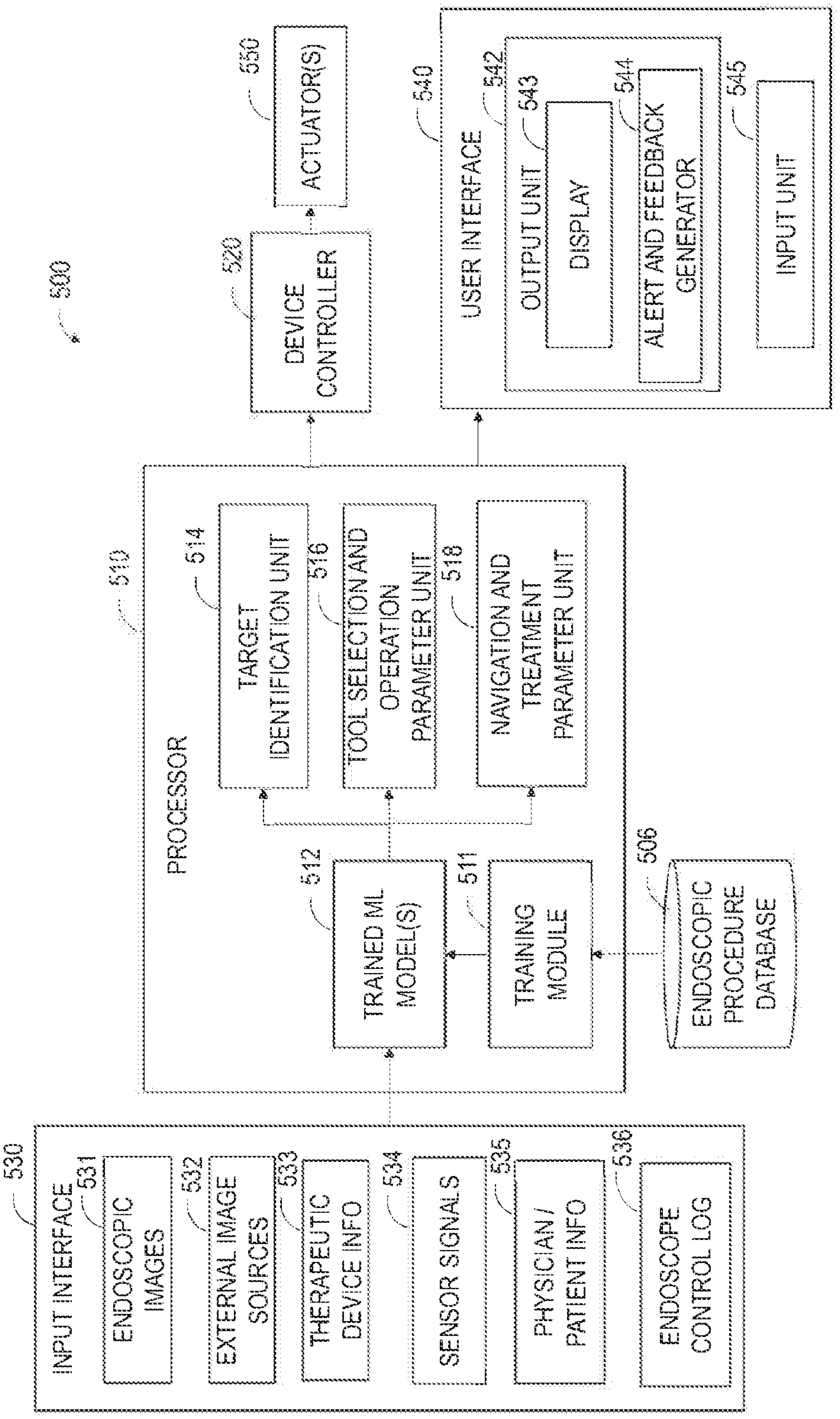
FIG. 5 is a block diagram illustrating an example of an anatomical target identification and endoscopic procedure planning system.

FIG. 5 is a block diagram illustrating an example of an anatomical target identification and endoscopic procedure planning system 500 that can be configured to identify an anatomical target (e.g., soft or hard tissue, or calculi in kidney, gallbladder, ureter, among other stone-forming regions), and generate a treatment plan for treating the identified target. By way of example and not limitation, the system 500 can be used to automatically identify characteristics of calculi in pancreaticobiliary system, and determine suitable tools and methods of operating such tools to remove the identified calculi.

The system 500 can be a part of the control unit 16 in FIG. 1, or the controller 408 in FIG. 4 along with other devices or functional units such as the endoscopic procedure data generator 450 and the treatment plan generator 460. As illustrated in FIG. 5, the system 500 can include a processor 510, a device controller 520, an input interface 530, and a user interface device 540. In some examples, the system 500 can include or be communicatively coupled to an endoscopic procedure database 506.

The processor 510 may include circuit sets comprising one or more other circuits or sub-circuits that may, alone or in combination, perform the functions, methods, or techniques described herein. In an example, the processor 510 and the circuits sets therein may be implemented as a part of a microprocessor circuit, which may be a dedicated processor such as a digital signal processor, application specific integrated circuit (ASIC), microprocessor, or other type of processor for processing information including physical activity information. Alternatively, the microprocessor circuit may be a general-purpose processor that may receive and execute a set of instructions of performing the functions, methods, or techniques described herein. In an example, hardware of the circuit set may be immutably designed to carry out a specific operation (e.g., hardwired). In an example, the hardware of the circuit set may include variably connected physical components (e.g., execution units, transistors, simple circuits, etc.) including a computer readable medium physically modified (e.g., magnetically, electrically, moveable placement of invariant massed particles, etc.) to encode instructions of the specific operation. In connecting the physical components, the underlying electrical properties of a hardware constituent are changed, for example, from an insulator to a conductor or vice versa. The instructions enable embedded hardware (e.g., the execution units or a loading mechanism) to create members of the circuit set in hardware via the variable connections to carry out portions of the specific operation when in operation. Accordingly, the computer readable medium is communicatively coupled to the other components of the circuit set member when the device is operating. In an example, any of the physical components may be used in more than one member of more than one circuit set. For example, under operation, execution units may be used in a first circuit of a first circuit set at one point in time and reused by a second circuit in the first circuit set, or by a third circuit in a second circuit set at a different time.

The processor 510 may identify an anatomical target and generate a treatment plan for treating the anatomical target using various sources of data specific to a patient received from the input interface 530. In some embodiments, the input interface 530 may be a direct data link between the system 500 and one or more medical devices that generate at least some of the input features. For example, the input interface 530 may transmit endoscopic images 531, external image sources 532, or sensor signals 534 directly to the system 500 during a therapeutic and/or diagnostic medical procedure. Additionally or alternatively, the input interface 530 may be a classical user interface that facilitates interaction between a user and the system 500. For example, the input interface 530 may facilitate a user interface through which the user may manually enter some input data to the system 500. Additionally or alternatively, the input interface 530 may provide the system 500 with access to an electronic patient record from which one or more data features may be extracted. In any of these cases, the input interface 530 can collect one or more of the following sources of data in association with a specific patient on or before a time at which the system 500 is used to identify an anatomical target and generate a treatment plan to treat said target.

By way of example and not limitation, data received from the input interface 530 may include one or more of endoscopic images 531 of the anatomical target, external image sources 532, endo-therapeutic device information 533, sensor signals 534, or physician/patient information 535, as illustrated in FIG. 5. The endoscopic images 531 may include real-time endoscope images of the anatomical target and its surrounding environment captured by an imaging sensor associated with the endoscope during an endoscopic procedure, such as DPOC or ERCP as described above. The external image sources 532 may include pre- or peri-procedural images acquired by external imaging devices other than the endoscope, which may include, for example, X-ray or fluoroscopy images, electrical potential map or an electrical impedance map, CT images, MRI images such as images obtained during MRCP, or acoustic images such as EUS images, among others. The endo-therapeutic device information 533 may include specification data, including size, dimension, shape, and structures of the endoscope used in an ERCP procedure or other steerable instruments such as a cannular, a catheter, or a guidewire; size, dimension, shape, and structures of treatment tools or devices for tissue removal (e.g., balloons or baskets for calculi removal). Such device specification information may be used to determine cannulation or navigation parameter values such as the angle and/or the force applied to the device, or for selecting suitable tools and determining methods of operating such tools to treat an anatomical target. The sensor signals 534 may be acquired by sensors coupled to the endoscope or a treatment device passing through the endoscope, or otherwise associated with the patient. In an example, the sensor signals 534 may be acquired by a proximity sensor at a distal portion of the endoscope. Examples of the sensor signals 534 may include position, direction, or proximity of a distal portion of the endoscope relative to an anatomical target. The physician/patient information 535 may include the operating physician's habits or preference of using a steerable elongate instrument, such as a preferred approach for cannulation and endoscope navigation, or past procedures of the similar type to the present procedure performed by the physician and the corresponding procedure outcome (e.g., success/failure assessment, procedure time, prognosis and complications). The physician/patient information 535 may include patient information, including patient demographics (e.g., age, gender, race), patient medical history such as prior endoscopic procedures and images or data associated therewith, etc. The endoscope control log data 536 may include time-series data representing changes in the movement and deflection of the device (e.g., endoscope, catheter, or cannula) on the endoscopic image as being maneuvered during a procedure.

The processor 510 may include one or more of a target identification unit 514, a tool selection and operation parameter unit 516, and a navigation and treatment parameter unit 518. The target identification unit 514 can use an input image (e.g., endoscopic images 531 and/or external image sources 532) to automatically identify the anatomical target of interest as one of a tissue target, a calculi target, an anatomical variance, or an anatomical landmark. The target identification unit 514 can identify one or more characteristics of the anatomical target. Examples of the identified target characteristics can include size, shape, hardness, or composition of a calculi target; and an inflammation state, a stricture level, or a malignancy state of a tissue target. In some examples, the target identification unit 514 can extract image features (e.g., statistical or morphological features) from the input image, and identify the target or target characteristics based on the extracted image features.

In some examples, an electromagnetic radiation can be incident on the anatomical target, a reflected signal is analyzed to produce spectroscopic data, and the target identification unit 514 can identify target or its characteristics (e.g., composition of a calculi target) using the spectroscopic data, examples of which are disclosed in the commonly assigned McLoughlin et al. U.S. patent application Ser. No. 16/947,485 entitled "LASER CONTROL USING A SPECTROMETER," Bukesov et al. U.S. patent application Ser. No. 16/984,447 entitled "TARGET IDENTIFICATION WITH OPTICAL FEEDBACK SIGNAL SPLITTER," which is hereby incorporated by reference in its entirety.

The tool selection and operation parameter unit 516 can automatically determine a tool recommendation for treating the identified anatomical target based on an input image (e.g., endoscopic images 531 and/or external image sources 532). Other data from the input interface 530, such as size and geometry of candidate tools for treating the anatomical target (as a part of the endo-therapeutic device information 533), sensor data indicating spatial restrictions of an environment of the anatomical target (as a part of the sensor signals 534), may additionally or alternatively be used by the tool selection and operation parameter unit 516 to make a tool recommendation. In some examples, the tool selection and operation parameter unit 516 can use the characteristics of the anatomical target, as identified by target identification unit 514, to determine a tool recommendation.

The tool recommendation can vary depending on the nature of the procedure. For example, in endoscopic lithotripsy procedures, the tool selection and operation parameter unit 516 can select an ablation tool as one of a mechanical lithotripsy device, a laser lithotripsy device, or an electrohydraulic lithotripsy device for ablating or fragmenting calculi. In ERCP for stone removal, the tool selection and operation parameter unit 516 can determine a calculi extraction tool as one of a balloon, a basket, or a snare for extracting calculi or fragments thereof. In endoscopic biopsy tissue acquisition procedures, the tool selection and operation parameter unit 516 can recommend a tissue collection tool as one of a brush, a snare, forceps, or a suction device. In some examples, the tool selection and operation parameter unit 516 can recommend a tool size for a particular tool type, such as a size of basket for entrapping the stone.

The tool selection and operation parameter unit 516 can automatically determine tool operation, such as recommended values of one or more operational parameters for navigating and operating the tool during the procedure to safely and effectively treat the anatomical target. Similar to the tool recommendation above, the tool selection and operation parameter unit 516 can determine values of the tool operational parameters using input image such as endoscopic images 531 and/or external image sources 532, optionally with other information from the input interface 530, or characteristics of the anatomical target identified by the target identification unit 514. The tool operational parameters can include a position, a heading direction, or an angle of a distal portion of the tool relative to the anatomical target to be treated. For example, in endoscopic tissue removal procedures involving an endoscopic knife, the tool selection and operation parameter unit 516 can determine one or more of an advance length, a location, or an angle of the endoscopic knife to precisely remove a desired amount of tissue while minimizing complications and preserving functions. In a rendezvous procedure involving an endoscope along with other percutaneous and/or surgical devices, the tool selection and operation parameter unit 516 can determine respective positions and postures of the endoscope and other devices. In ERCP for calculi removal, the tool selection and operation parameter unit 516 can determine one or more of a position, a posture, and an angle of a balloon catheter or a basket catheter for extracting stone (as illustrated in FIGS. 4B and 4C). In an endoscopic lithotripsy procedure involving a lithotripsy probe, the tool selection and operation parameter unit 516 can determine one or more of an angle, a distance between the tip of the laser lithotripsy probe and a calculi target, or a laser system setting (e.g., laser output), among other parameters.

In some examples, the target identification unit 514 can identify a specific geometric location on the anatomical target for receiving a treatment, and the tool selection and operation parameter unit 516 can recommend an aiming angle or a posture of a treatment tool such that the treatment energy is directed at the identified geometric location. For example, in laser lithotripsy procedures, the tool selection and operation parameter unit 516 can recommend an aiming angle or an orientation of a laser lithotripsy device with respect to a calculi target to direct a laser beam at the centroid of a calculi to more effectively fragment the target.

The navigation and treatment parameter unit 518 can automatically estimate navigation or treatment parameters for an instrument or a treatment tool used in an endoscopic procedure. In an example, the navigation and treatment parameter unit 518 can automatically estimate a position of the distal portion (e.g., the functional section 30 of the endoscope 14 as shown in FIG. 1) of an endoscope or other steerable elongate instrument relative to an anatomical target of interest, such as a distance from the endoscope distal portion to duodenal papilla; a heading direction of the distal portion of the steerable elongate instrument relative to the anatomical target; an insertion angle of a cannula or a surgical element used in cannulation; a protrusion amount of a cannula or a surgical element; a speed or a force applied to the endoscope distal portion or a surgical element; a rotational direction or a cutting area of a surgical element; among others. In another example, the navigation and treatment parameter unit 518 can automatically estimate navigation parameters for the tools selected by the tool selection and operation parameter unit 516, including a first path for advancing the tool toward the anatomical target, and a second path for retrieving the tool and the extracted anatomical target (e.g., calculi or fragments thereof). In an example where the anatomical target being treated includes multiple structures or elements (e.g., multiple stones, or fragments produced by a lithotripsy treatment of a large stone), the navigation and treatment parameter unit 518 can determine an order of treatment, such as an order of removing the multiple stones or fragments.

In some examples, the navigation and treatment parameter unit 518 can determine a probability of success or an estimate of procedure time when using the selected treatment tool in accordance with the automatically determined tool operational parameters and the navigation or treatment parameters. For example, if the tool selection and operation parameter unit 516 recommends a basket of a specific size for use in removing an identified stone in ERCP, the navigation and treatment parameter unit 518 can determine a probability of successfully extracting the identified stone and an estimate of extraction time.

One or more of the target identification unit 514, the tool selection and operation parameter unit 516, or the navigation and treatment parameter unit 518 can use one or more trained machine-learning (ML) model(s) 512 to perform respective tasks of automatic target identification, tool selection, and parameter estimation and procedure planning. The ML model(s) can have a neural network structure comprising an input layer, one or more hidden layers, and an output layer. The input interface 530 may deliver one or more sources of input data, or features generated therefrom, into the input layer of the ML model(s) 512 which propagates the input data or data features through one or more hidden layers to the output layer. The ML model(s) 512 can provide the system 500 with the ability to perform tasks, without explicitly being programmed, by making inferences based on patterns found in the analysis of data. The ML model(s) 512 explores the study and construction of algorithms (e.g., ML algorithms) that may learn from existing data and make predictions about new data. Such algorithms operate by building the ML model(s) 512 from training data in order to make data-driven predictions or decisions expressed as outputs or assessments.

The ML model(s) 512 may be trained using supervised learning or unsupervised learning. Supervised learning uses prior knowledge (e.g., examples that correlate inputs to outputs or outcomes) to learn the relationships between the inputs and the outputs. The goal of supervised learning is to learn a function that, given some training data, best approximates the relationship between the training inputs and outputs so that the ML model can implement the same relationships when given inputs to generate the corresponding outputs. Unsupervised learning is the training of an ML algorithm using information that is neither classified nor labeled, and allowing the algorithm to act on that information without guidance. Unsupervised learning is useful in exploratory analysis because it can automatically identify structure in data.

Common tasks for supervised learning are classification problems and regression problems. Classification problems, also referred to as categorization problems, aim at classifying items into one of several category values. Regression algorithms aim at quantifying some items (for example, by providing a score to the value of some input). Some examples of commonly used supervised-ML algorithms are Logistic Regression (LR), Naive-Bayes, Random Forest (RF), neural networks (NN), deep neural networks (DNN), matrix factorization, and Support Vector Machines (SVM). Examples of DNN include a convolutional neural network (CNN), a recurrent neural network (RNN), a deep belief network (DBN), or a hybrid neural network comprising two or more neural network models of different types or different model configurations.

Some common tasks for unsupervised learning include clustering, representation learning, and density estimation. Some examples of commonly used unsupervised learning algorithms are K-means clustering, principal component analysis, and autoencoders.

Another type of ML is federated learning (also known as collaborative learning) that trains an algorithm across multiple decentralized devices holding local data, without exchanging the data. This approach stands in contrast to traditional centralized machine-learning techniques where all the local datasets are uploaded to one server, as well as to more classical decentralized approaches which often assume that local data samples are identically distributed. Federated learning enables multiple actors to build a common, robust machine learning model without sharing data, thus allowing to address critical issues such as data privacy, data security, data access rights and access to heterogeneous data.

As illustrated in FIG. 5, the ML model(s) 512 may be trained using a training module 511, which can be included in the processor 510 as shown in FIG. 5. Alternatively, the training module 511 can be implemented in a separate unit. To train an ML model, a training dataset can be constructed using past endoscopic procedure data such as selected and retrieved from the endoscopic procedure database 506. The training data may include procedure data acquired during respective endoscopic procedures performed on a plurality of patients. The endoscopic procedures can be those of the same type as the endoscopic procedure to be performed on the present patient. The training data can be from various data sources, such as any of those shown in the input interface 530. The training data used for training an ML model can vary depending on the parameters to estimate. In an example of a ML-based determination of canulation and endoscope navigation, the training data can include endoscopic images or videos showing patient anatomy, cannulation and endoscope navigation routes, progress of cannulation or navigation, among other information. In an example of a ML-based tool selection for treating an anatomical target (e.g., calculi removal), the training data can include images of respective anatomical targets of the plurality of patients anatomy targets, and information of tools used in past procedures to treat respective anatomical targets (e.g., lithotripsy devices for fragmenting calculi, calculi removal devices for extracting calculi or fragments). The tool information can include types, sizes, and operational data associated with the use of such tools in past procedures (which can be recorded during the procedure, or obtained offline via analysis of the endoscopic images or videos). The training data may additionally include assessments of the treatments using such tools in the past procedures, such as success/failure assessment, total procedure time, procedure difficulty and skills requirement, etc.

In an example, the training data can be screened such that only data of procedures performed by certain physicians (such as those with substantially similar experience levels to the operating physician), and/or data of procedures on certain patients with special requirement (such as those with substantially similar anatomy or patient medical information to the present patient) are included in the training dataset. In an example, the training data can be screened based on a success rate of the procedure, including times of attempts before a successful cannulation or navigation, such that only data of procedures with a desirable success rate achieved within a specified number of attempts are included in the training dataset. In another example, the training data can be screened based on complication associated with the patients. In some examples, particularly in case of a small training dataset (such as due to data screening), the ML model can be trained to identify anatomical target (including type, location, size, composition, among other characteristics), determine a suitable treatment tool and methods of operating such tool to treat the anatomical target, and determine navigation and treatment parameters by extrapolating, interpolating, or bootstrapping the training data, thereby creating a treatment plan specifically tailored to the specific patient and physician. The training of the ML model may be performed continuously or periodically, or in near real time as additional procedure data are made available. The training involves algorithmically adjusting one or more ML model parameters, until the ML model being trained satisfies a specified training convergence criterion.

In some examples, a plurality of ML models can be separately trained, validated, and used (in an inference phase) in different applications, such as estimating different parameters of the devices used in an endoscopic procedure or planning of such a procedure. For example, a first ML model (or a first set of ML models) may be trained to establish a correspondence between (i) endoscopic images and/or other external images of anatomical targets from past endoscopic procedures (optionally along with other information) and (ii) various anatomical target types (e.g., a tissue target, a calculi target, an anatomical variance, or an anatomical landmark) and target characteristics (e.g., size, shape, hardness, or composition of a calculi target, or inflammation state, stricture or stenosis level, or a malignancy state of a tissue target). The trained first ML model(s) can be used by the target identification unit 514 in an inference phase to identify, from an input image (or a sequence of images or a live video) of an anatomical target (optionally along with other information), the type and characteristics of the anatomical target.

In an example, a second ML model (or a second set of ML models) may be trained to establish a correspondence between (i) endoscopic images and/or other external images of anatomical targets from past endoscopic procedures (optionally along with other information) and (ii) tools used in those past procedures (e.g., various lithotripsy devices for ablating or fragmenting calculi, or calculi removal devices for extracting calculi or fragments thereof) and the tool characteristics including their types, sizes, and operational parameters. The trained second ML model(s) can be used by the tool selection and operation parameter unit 516 in an inference phase to automatically determine, from an input image (or a sequence of images or a live video) of an anatomical target (optionally along with other information), a tool recommendation including particular type, size, and methods of operation of a tool for treating the anatomical target, such as an endoscopic calculi management device for fragmenting and/or extracting the calculi identified by the target identification unit 514.

In an example, a third ML model (or a third set of ML models) may be trained to establish a correspondence between (i) endoscopic images and/or other external images of anatomical targets from past endoscopic procedures (optionally along with other information) and (ii) navigation and treatment parameters in those past procedures, including direction, angle, speed, force, and amount of intrusion for navigating and placing endoscopes, catheters, or treatment tools to the anatomical target, order of treating multiple anatomical targets, or estimated success rate and procedure time, among other parameters. The trained second ML model(s) can be used by the navigation and treatment parameter unit 518 in an inference phase to automatically determine, from an input image of patient anatomy including the anatomical target (optionally along with other information), proper navigation and treatment parameters that may be used as a procedure guidance.

The device controller 520 can generate a control signal to one or more actuators 550, such as a motor actuating a robot arm. The one or more actuators 550 can be coupled to a steerable elongate instrument, which can be a diagnostic or therapeutic endoscope, a cannula, a catheter, a guidewire, or a guide sheath, among others. The steerable elongate instrument may include a treatment tool (e.g., a lithotripsy device or a calculi extraction device) robotically operable via the one or more actuators 550. In response to the control signal, the one or more actuators 550 can robotically adjust position, posture, direction, and navigation path of the steerable elongate instrument and a treatment tool included therein in accordance with the navigation and treatment parameters estimated by the navigation and treatment parameter unit 518, and/or the tool operational parameters estimated by the tool selection and operation parameter unit 516.

As some of the canulation or navigation parameters (e.g., positions, angle, direction, navigation path) associated with a cannula or GW are determined based on images (e.g., endoscopic images or other images) generated an imaging system, such canulation or navigation parameters are with reference to the coordinates of the imaging system. To facilitate robotic control of the cannula or GW in accordance with the canulation or navigation parameters, in some examples the coordinates of the robotic system may be registered with the coordinates of the imaging system, such that an anatomical position in the coordinates of the imaging system can be mapped to a corresponding position in the coordinates of the robotic system. Such registration may be performed, for example, by using distinct landmarks whose positions are known in respective coordinate systems. The registration may be intensity- or feature-based, and can be represented by transformation model (a linear or a non-linear model) that maps the coordinates of imaging system to the coordinates of the robotic system.

The user interface device 540 can include an output unit 542 and an input unit 545, which are examples of the output unit 18 and the input unit 20 respectively as shown in FIG. 2. The input unit 545 can receive input from the user or from other data sources. In an example, the input interface 530 can be included in the input unit 545. The output unit 542 can include a display 543 that can display images of the anatomical target as recognized by the target identification unit 514. Information about the identified target (e.g., type, location, size, composition, among other characteristics) identified by the target identification unit 514, tool recommendations including type and size of the tools and methods of operating such recommended tools such as values of one or more operational parameters generated by the tool selection and operation parameter unit 516, can also be displayed on the display 543. In some examples, the display 543 can present a graphical representation of the navigation of an endoscope or treatment tools based on the navigation parameters produced by the navigation and treatment parameter unit 518. In some examples, a plurality of anatomical targets (e.g., multiple biliary ductal stones) may be identified and their images displayed on the display 543, and responsive to a user selection of a particular target, the display may automatically display information about the selected target and treatment parameters. Examples of a user interface for displaying the anatomical target, target characteristics, and a treatment plan as a endoscopic procedure guide as discussed below, such as with reference to FIG. 6.

In an example, the displayed region of the anatomical target images can be automatically adjusted according to the position or direction of a distal end of the endoscope relative to an anatomical target. For example, the output unit 542 may automatically zoom in an image as the endoscope tip gets closer to the papilla to show more details of the papilla. Alternatively, the zooming function can be activated and adjusted manually by the user (e.g., operating physician) via the input unit 545. In an example, the output unit 542 can display a cross-section view of an anatomy in a direction specified by a user, such as via the input unit 545. In an example, the user may adjust viewing angle (e.g., rotating the view) and have a 360-degree view of the reconstructed or integrated 3D images via the input unit 545. In an example, at least a portion of the input unit 545 can be incorporated into the endoscope, such as the handle section 32 of endoscope 14, to facilitate user operation during the procedure.

In some examples, the display 543 may automatically center the anatomical target in a viewing area, such as based on the distance and viewing angle of the imaging device (e.g., camera) relative to the anatomical target. In an example, the device controller 520 can control the positioning and direction of the endoscope to adjust viewing angle of the imaging device to achieve auto-centering of the anatomical target. Additionally or alternatively, the device controller 520 can control an image processor to post-process the acquired image including repositioning the identified anatomical target at the center of the viewing area.

In some examples, the output unit 542 may display on the image a visual indication of the anatomical target (e.g., duodenal papilla), a projected navigation path toward the anatomical target; or a progression of the endoscope toward the targe anatomy along the projected navigation path. Display settings can be adjusted by the user via the input unit 545. The visual indication may take the format of markers, annotations (icons, texts, or graphs), highlights, or animation, among other visual indicators. For example, markers of different shapes, colors, forms, or sizes can be displayed on the reconstructed or integrated image to distinguish different tissue, anatomical regions, their accessibility or criticality.

The output unit 542 can include an alert and feedback generator 544 that can generate an alert, a notification, or other formats of human-perceptible feedback to the operating physician on the status or progress of the cannulation or navigation in reference to the navigation plan. For example, an alert can be generated to indicate a risk of tissue damage associated with improper cannulation. The feedback can be in one or more forms of audio feedback, visual feedback, or haptic feedback. For example, when the endoscope tip enters or comes closer to a "critical zone" (e.g., proximity sensor detecting a distance to a critical anatomy of interest shorter than a threshold distance), the critical zone can be shown in different colors to represent such distance (e.g., green zone, yellow zone, and read zone as the endoscope gets closer to the critical zone). Additionally or alternatively, haptic feedback such as touch or vibration may be generated and felt by the operating physician. In an example, the alert and feedback generator 544 can automatically adjust the vibration strength according to the distance to the critical zone. For example, a low vibration can be generated when the endoscope tip is in a green zone. If the system predicts, based on present advancing speed and direction of the endoscope, that the endoscope tip will reach the critical zone in a time lower than a predetermined threshold, then alert and feedback generator 544 can apply moderate vibration when the endoscope tip reaches a yellow zone, and apply high vibration when the endoscope tip reaches red zones to indicate a risk of tissue damage. The real-time alert and feedback in an image-guided endoscopic procedure as described herein can improve the efficiency of cannulation and endoscope navigation, especially for inexperienced physicians, and can improve endoscopic procedure success rate and patient outcome.

Figure 6:
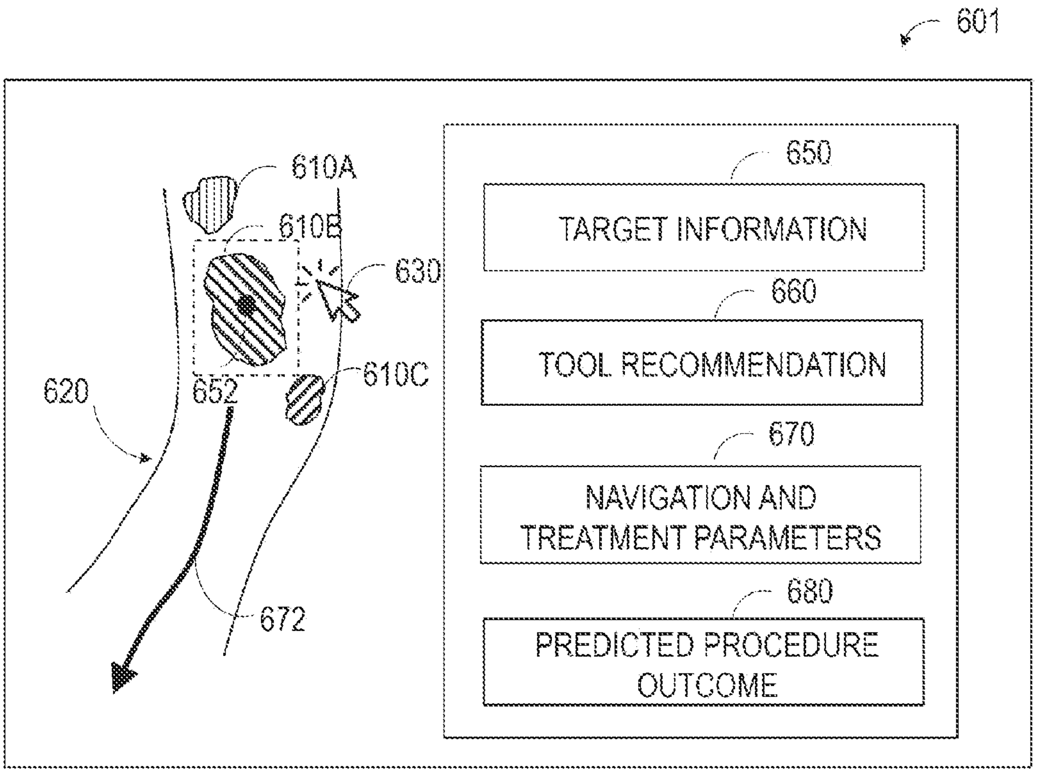
FIG. 6 is a diagram illustrating a portion of a user interface displaying properties of an anatomical target selected by a user from the user interface and an automatically generated treatment plan for treating the target.

FIG. 6 is a diagram illustrating a portion of a user interface 601 that displays information about an anatomical target and a treatment plan automatically generated by the anatomical target identification and endoscopic procedure planning system 500. In this example, the anatomical target includes a plurality of calculi targets 610A, 610B, 610C, . . . , located in a ductal portion 620. A user may hover a mouse cursor 630 over, or click on, the image of a calculi target of interest (e.g., calculi target 610B as shown in FIG. 6), which triggers display of one or more information boxes including, for example, a target information 650, a tool recommendation 660, a navigation and treatment parameter 670, or a predicted procedure outcome 680. In some examples, one or more of the information boxes can be presented in a format of a pop-up menu, with contents in an information box being display upon a user interaction, such as a mouse-click or hovering the cursor 630 on an information box. For example, hovering the cursor 630 on the tool recommendation 660 may trigger the display of type and size of a recommended tool, and values of tool operational parameters such as position, posture, angle of the recommended tool.

The target information 650 may include type, location, size, and composition of the calculi target 610B, as identified by the target identification unit 514. The tool recommendation 660 can include type and size of a tool (e.g., a basket) and values of tool operational parameters (e.g., position, posture, angle of the tip of the scope for delivering the basket with respect to the calculi target 610B) to remove the calculi target 610B, as generated by the tool selection and operation parameter unit 516. The navigation and treatment parameters 670 can include navigation or treatment parameters for an endoscope or the recommended tool, such as a graphical depiction of a recommended path 672 for retrieving the tool along with the entrapped calculi target 610B, an order of removing the calculi targets 610A, 610B, 610C . . . , among others. The predicted procedure outcome 680 may include a probability of success and estimated procedure time associated with the recommended tool being used according to the recommended method, such as a probability of successfully extracting the calculi target 610B. The probability can have a textual or graphical representation, such as different colors or tones representing different probabilities. In some examples, the predicted procedure outcome 680 may include difficulty and skills requirement for performing the procedure.

In an example where the tool recommendation 660 includes a laser lithotripsy device recommended for ablating or fragmenting a calculi target such as calculi target 610B, the target information 650 may include an identified geometric location 652, such as a centroid, on the calculi target 610B at which a laser beam is directed. The geometric location 652 can be automatically determined by the target identification unit 514, and marked on the image of the calculi target 610B. When the user clicks on, or hovers the mouse cursor 630 on, the tool recommendation box 660, an aiming angle or an orientation of the tip of the laser lithotripsy device (such that the laser beam is directed at the centroid) and recommended laser output, among other tool operational parameters determined by the tool selection and operation parameter unit 516, can be displayed on the user interface 601.

Figure 7A:
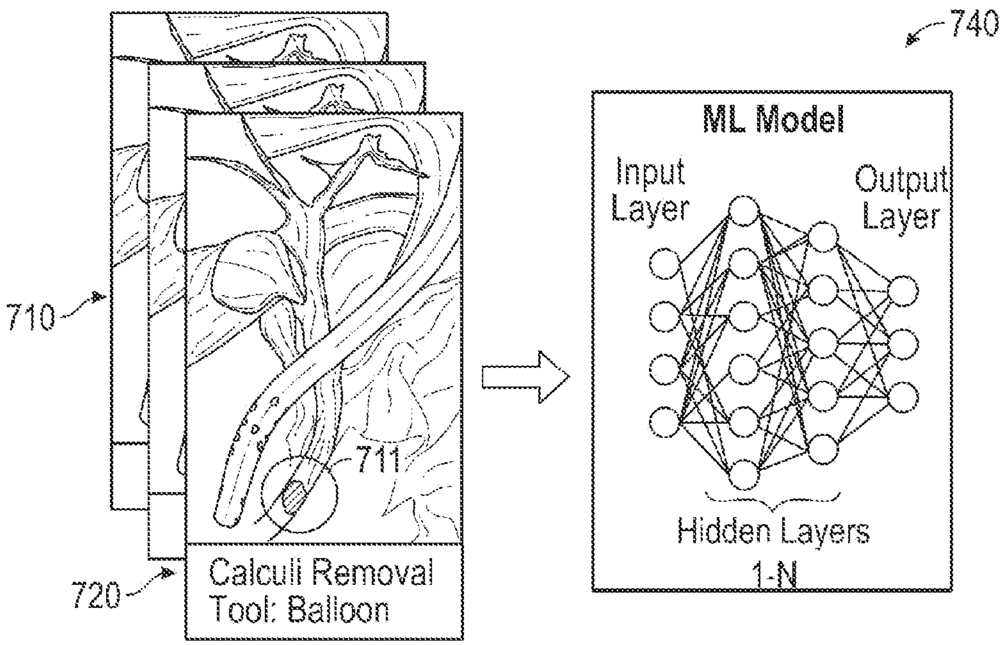
FIGS. 7A-7B are diagrams illustrating an example of training an ML model and using the trained ML model to generate a treatment plan for removing biliary ductal calculi.
Figure 7B:
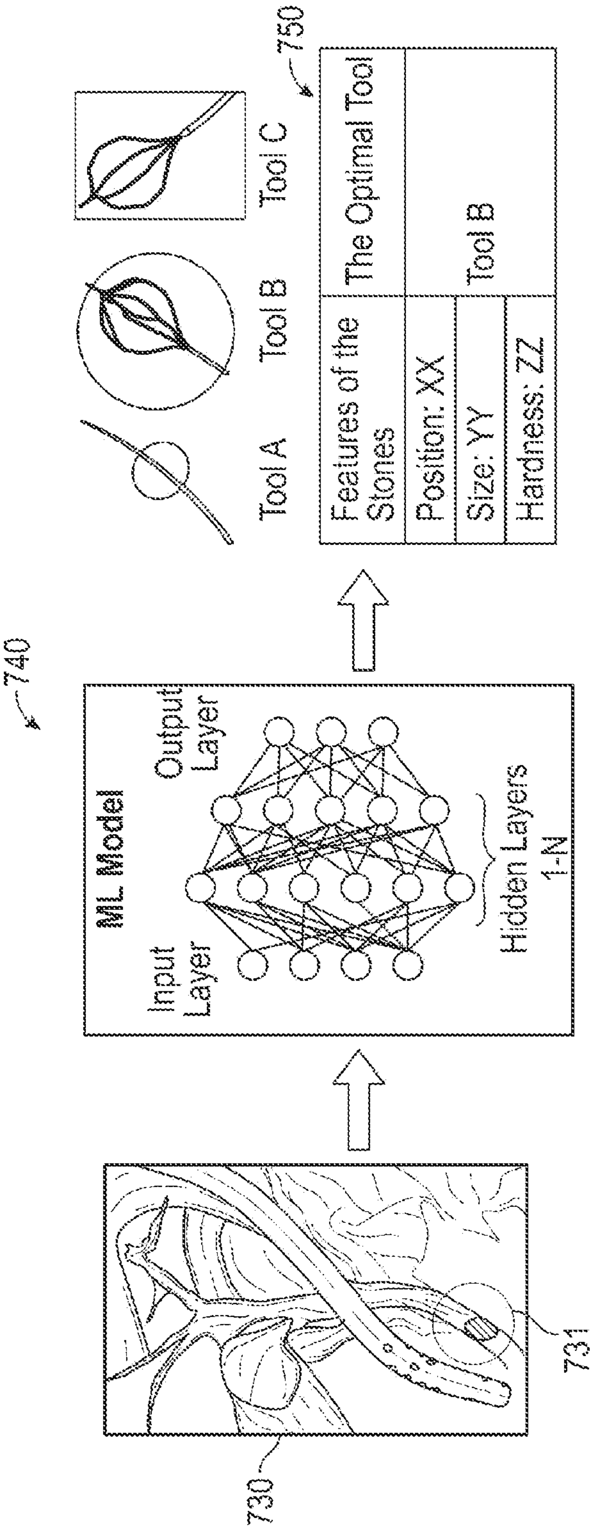

FIGS. 7A-7B are diagrams illustrating an example of training an ML model and using the trained ML model to generate a treatment plan for endoscopically removing biliary ductal calculi. FIG. 7A illustrates an ML model training (or learning) phase during which an ML model 740 may be trained using training data comprising a plurality of images 710 of anatomical targets 711 (e.g., biliary ductal calculi) from past endoscopic procedures performed on a plurality of patients. The training data may also include annotated procedure data 720, including information of the treatment tools used in each procedure corresponding to the plurality of images 710, such as calculi removal device used for extracting calculi or fragments. In some examples, the treatment tool information can additionally or alternatively include lithotripsy devices used in each procedure for ablating or fragmenting calculi. The information of the treatment tools can include type and size of the tools, and operational data associated with the use of such tools in past procedures. The training data may also include procedure outcome, such as success/failure assessment of the procedure, estimated procedure time, procedure difficulty and skills requirement, etc. The ML model 740 can be trained using supervised learning, unsupervised learning, or reinforcement leaning. Examples of ML model architectures and algorithms may include, for example, decision trees, neural networks, support vector machines, or a deep-learning networks, etc. Examples of deep-learning networks include a convolutional neural network (CNN), a recurrent neural network (RNN), a deep belief network (DBN), or a hybrid neural network comprising two or more neural network models of different types or different model configurations.

The training of the ML model may be performed continuously or periodically, or in near real time as additional procedure data are made available. The training involves algorithmically adjusting one or more ML model parameters, until the ML model being trained satisfies a specified training convergence criterion. The trained ML model 740 can establish a correspondence between the images of anatomical targets from past endoscopic procedures and the tools and the tool operational parameters used in the treatment of anatomical targets.

FIG. 7B illustrates an inference phase during which a live image 730 of a calculi target 731 is applied to the trained ML model 740 to automatically determine a tool recommendation, including type, size, and methods of operating the recommended tool to extract the calculi target 731. The tool recommendation can be communicated to a user (e.g., a physician) to assist in procedure planning. FIG. 7B illustrates a calculi removal tool "B" (a basket of a particular size) is recommended by the trained ML model 740 for the given image 730 of the calculi target 731. A report 750 including various characteristics of the calculi target 731 (which can be generated by the trained ML model 740 as well, as discussed below) and the recommended tool "B" can be presented to the user. Additionally or alternatively, the tool recommendation may be provided to a robotic system to facilitate a robot-assisted treatment (e.g., calculi removal procedure).

In some examples, the ML model 740 (or a different ML model) may be trained to recognize anatomical target (e.g., as a tissue target or a calculi target) and identify one or more target characteristics (e.g., size, location, shape, hardness, or composition of a calculi target) using the training data comprising the images 710 of anatomical targets from past endoscopic procedures and known types and characteristics of those targets as shown in the images 710. In the inference phase as shown in FIG. 7B, a live image 730 can be applied to the trained ML model 740 to determine various characteristics of the anatomical target, and an optical tool can be determined based on the characteristics of the anatomical target automatically identified by the trained ML model 740 from the live image 730.

Figure 8:
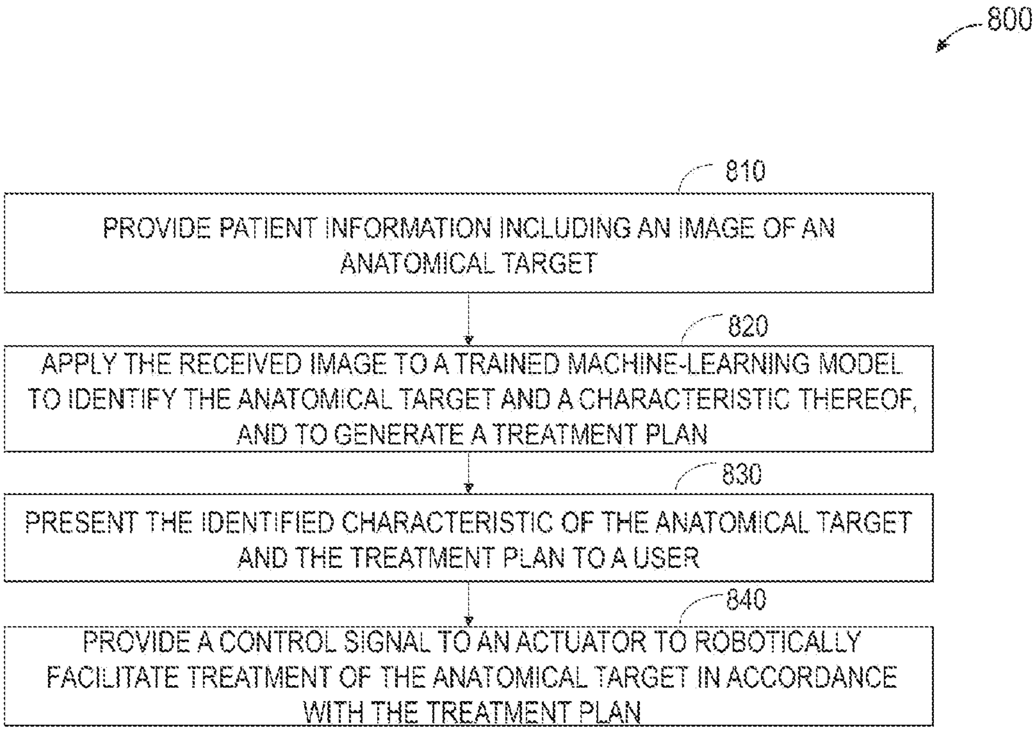
FIG. 8 is a flow chart illustrating an example method for identifying an anatomical target and planning an endoscopic procedure via an endoscopic system.

FIG. 8 is a flow chart illustrating an example method 800 for identifying an anatomical target and planning an endoscopic procedure via a endoscopic system, such as the anatomical target identification and endoscopic procedure planning system 500 as illustrated in FIG. 5. The anatomical target can include soft or hard tissue, or calculi in kidney, gallbladder, ureter, among other stone-forming regions. Although the processes of the method 800 are drawn in one flow chart, they are not required to be performed in a particular order. In various examples, some of the processes can be performed in a different order than that illustrated herein.

At 810, patient information including an image of an anatomical target can be provided for use in automatic planning of an endoscopic procedure to treat the anatomical target. The image of the anatomical target may include real-time endoscope images of the anatomical target and its surrounding environment captured by an imaging sensor associated with the endoscope during an endoscopic procedure, such as DPOC or ERCP, or images from other sources including, for example, X-ray or fluoroscopy images, electrical potential map or an electrical impedance map, CT images, MRI images such as images obtained from Magnetic resonance cholangiopancreatography (MRCP) procedures, or acoustic images such as endoscopic ultrasonography (EUS) images, among others. In addition to the images of the anatomical target, other information may be used in the procedure planning process, including, for example, endo-therapeutic device information, sensor signals, physician information (e.g., the operating physician's habits or preference of using the steerable elongate instrument), and endoscope control log data, as described above with reference to FIG. 5.

At 820, the images of the anatomical target, and optionally other information received at step 810, may be provided to a trained machine-learning (ML) model to identify the anatomical target and a characteristic thereof, and to generate a treatment plan for treating the anatomical target. The ML model may be trained using procedure data from past endoscopic procedures on a plurality of patients. The past procedure data can include images of anatomical targets of the plurality of patient and identified characteristics of the anatomical targets and assessments of treatment plans for treating respective anatomical targets. The trained ML model may be used to automatically identify the anatomical target of interest as one of a tissue target, a calculi target, an anatomical variance, or an anatomical landmark, such as using the target identification unit 514. Additionally, one or more characteristics of the anatomical target, such as size, shape, hardness, or composition of a calculi target, or an inflammation state, a stricture level, or a malignancy state of a tissue target, can be identified. In some examples, statistical or morphological features extracted from the input image can be used to identify the anatomical target or target characteristics. In some examples, spectroscopic data obtained from the light reflected from the anatomical target in response to electromagnetic radiation can be used to identify the anatomical target or target characteristics.

The same trained ML model, or a separately trained ML model may automatically determine a recommended tool of specific type and size for use in treating the identified anatomical target based at least on the input image. Other data may additionally or alternatively be used to make such tool recommendation, including, for example, position of the anatomical target, spatial restrictions of an environment of the anatomical target, or sizes or geometries of candidate tools for treating the anatomical target. The tool recommendation can vary depending on the nature of the procedure. For example, in endoscopic lithotripsy (stone fragment) procedures, the recommended tool can include a mechanical lithotripsy device, a laser lithotripsy device, or an electrohydraulic lithotripsy device for ablating or fragmenting calculi. In ERCP for stone removal, the recommended tool can include a balloon, a basket, or a snare for extracting calculi or fragments thereof. In endoscopic biopsy tissue acquisition procedures, the recommended tool can include a brush, a snare, forceps, or a suction device.

The same trained ML model, or a separately trained ML model may automatically determine proper tool operations, such as recommended values of one or more operational parameters for navigating and operating the tool during the procedure to safely and more effectively treat the anatomical target, based at least on the input image. The tool operational parameters can include a position, a heading direction, or an angle of a distal portion of the tool relative to the anatomical target to be treated. In an example, the tool operational parameters can include an energy output of a lithotripsy device for ablating or fragmenting a calculi target. In an example, the trained ML model can be used to determine a geometric location on a calculi target, and to determine an aiming angle or orientation of a laser lithotripsy device to direct the laser beam at a particular geometric location (e.g., the centroid) on the calculi target to more effectively fragment such structure.

The same trained ML model, or a separately trained ML model may automatically estimate navigation or treatment parameters for an instrument or a treatment tool used in an endoscopic procedure, such as navigation path for navigating the steerable elongate instrument or maneuvering the recommended tool with respect to the anatomical target. In some examples, the anatomical target includes a plurality of anatomical structures to be treated. The trained ML model can be used to determine the treatment plan including an order of treating the plurality of structures. In some examples, the trained ML model may be used to determine a probability of success, or an estimate of treatment time in accordance with the treatment plan (including the recommended treatment tool, the automatically determined tool operational parameters, and the navigation or treatment parameters).

At 830, the identified characteristic of the anatomical target and the treatment plan generated at 820 may be presented to a user, such as being displayed on a display of a user interface. In an example, images of the plurality of targets can be displayed on a user interface. A user can make a selection of one of the plurality of targets using a UI control element, which triggers display of the characteristics of the selected target, which may include, for example, type, location, size, and composition of the selected target. The user selection of a target may additionally or alternatively trigger display of a treatment plan for treating the selected target, which may include, for example, type and size of a recommended tool, recommended values of tool operational parameters, navigation or treatment parameters for an endoscope or the recommended tool (e.g., graphical depiction of a recommended path), predicted procedure outcome such as a probability of success and estimated time of treatment, as illustrated in FIG. 6. The operating physician may use the recommended tool and the automatically generated treatment plan as a guidance to perform the procedure.

At 840, a control signal may be provided to one or more actuators to robotically facilitate operation of a steerable elongate instrument or a treatment tool associated therewith (such as the recommended treatment tool) to treat the anatomical target in accordance with the generated treatment plan determined at step 820. The steerable elongate instrument can include be a diagnostic or therapeutic endoscope, a cannula, a catheter, a guidewire, or a guide sheath, among others. The actuator can be a motor actuating a robot arm operably coupled to the steerable elongate instrument. The steerable elongate instrument may include a treatment tool (e.g., a lithotripsy device or a calculi extraction device) robotically operable via the actuator. In response to the control signal, the actuator can robotically adjust position, posture, direction, and navigation path of the steerable elongate instrument and the treatment tool included therein, and perform treatment at the anatomical target in accordance with the navigation and treatment parameters and/or the tool operational parameters generated at 820.

Figure 9:
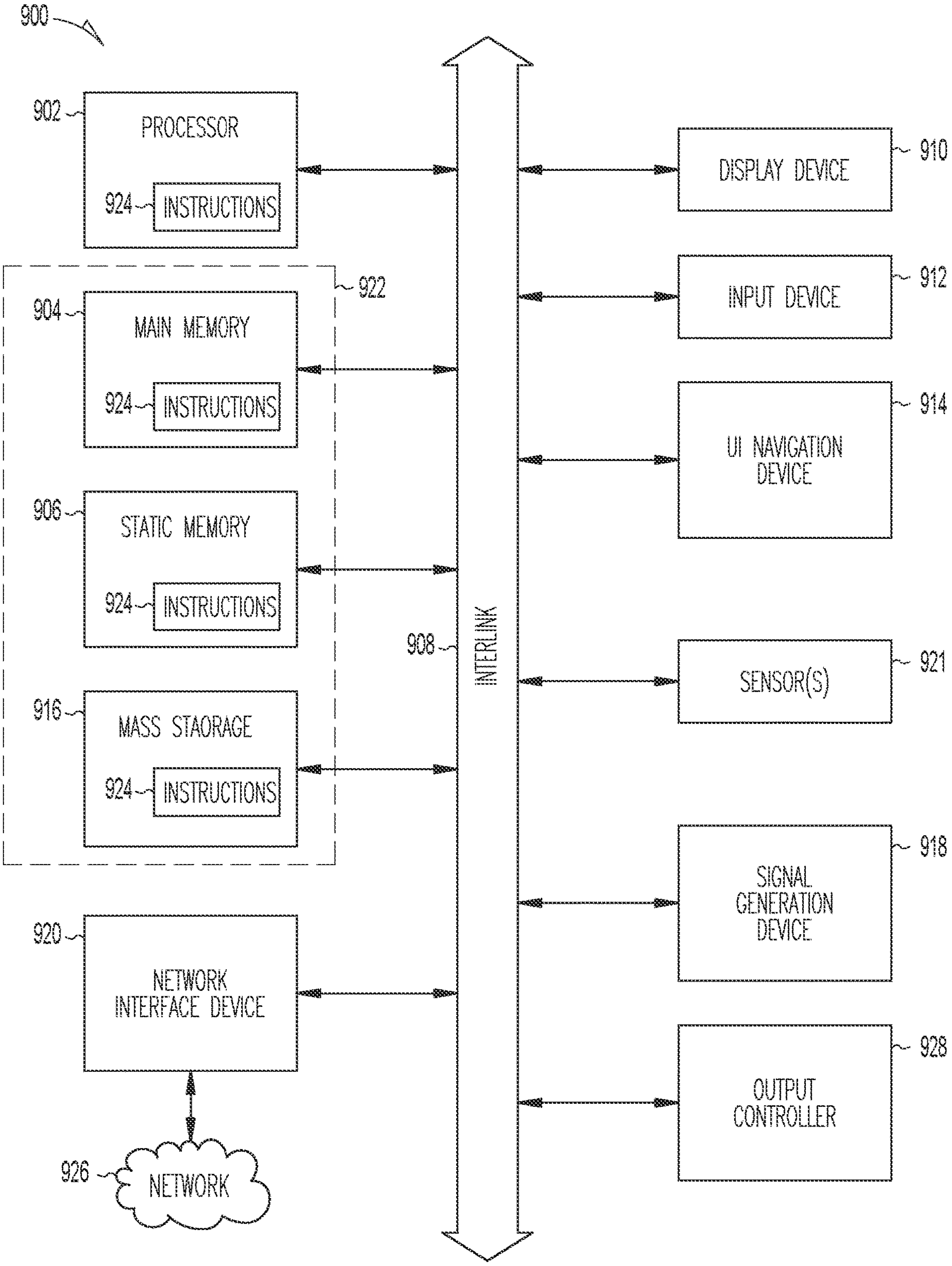
FIG. 9 is a block diagram illustrating an example machine upon which any one or more of the techniques (e.g., methodologies) discussed herein may perform.

FIG. 9 illustrates generally a block diagram of an example machine 900 upon which any one or more of the techniques (e.g., methodologies) discussed herein may perform. Portions of this description may apply to the computing framework of various portions of the anatomical target identification and endoscopic procedure planning system 500, such as the processor 510 and the device controller 520.

In alternative embodiments, the machine 900 may operate as a standalone device or may be connected (e.g., networked) to other machines. In a networked deployment, the machine 900 may operate in the capacity of a server machine, a client machine, or both in server-client network environments. In an example, the machine 900 may act as a peer machine in peer-to-peer (P2P) (or other distributed) network environment. The machine 900 may be a personal computer (PC), a tablet PC, a set-top box (STB), a personal digital assistant (PDA), a mobile telephone, a web appliance, a network router, switch or bridge, or any machine capable of executing instructions (sequential or otherwise) that specify actions to be taken by that machine. Further, while only a single machine is illustrated, the term "machine" shall also be taken to include any collection of machines that individually or jointly execute a set (or multiple sets) of instructions to perform any one or more of the methodologies discussed herein, such as cloud computing, software as a service (SaaS), other computer cluster configurations.

Examples, as described herein, may include, or may operate by, logic or a number of components, or mechanisms. Circuit sets are a collection of circuits implemented in tangible entities that include hardware (e.g., simple circuits, gates, logic, etc.). Circuit set membership may be flexible over time and underlying hardware variability. Circuit sets include members that may, alone or in combination, perform specified operations when operating. In an example, hardware of the circuit set may be immutably designed to carry out a specific operation (e.g., hardwired). In an example, the hardware of the circuit set may include variably connected physical components (e.g., execution units, transistors, simple circuits, etc.) including a computer readable medium physically modified (e.g., magnetically, electrically, moveable placement of invariant massed particles, etc.) to encode instructions of the specific operation. In connecting the physical components, the underlying electrical properties of a hardware constituent are changed, for example, from an insulator to a conductor or vice versa. The instructions enable embedded hardware (e.g., the execution units or a loading mechanism) to create members of the circuit set in hardware via the variable connections to carry out portions of the specific operation when in operation. Accordingly, the computer readable medium is communicatively coupled to the other components of the circuit set member when the device is operating. In an example, any of the physical components may be used in more than one member of more than one circuit set. For example, under operation, execution units may be used in a first circuit of a first circuit set at one point in time and reused by a second circuit in the first circuit set, or by a third circuit in a second circuit set at a different time.

Machine (e.g., computer system) 900 may include a hardware processor 902 (e.g., a central processing unit (CPU), a graphics processing unit (GPU), a hardware processor core, or any combination thereof), a main memory 904 and a static memory 906, some or all of which may communicate with each other via an interlink (e.g., bus) 908. The machine 900 may further include a display unit 910 (e.g., a raster display, vector display, holographic display, etc.), an alphanumeric input device 912 (e.g., a keyboard), and a user interface (UI) navigation device 914 (e.g., a mouse). In an example, the display unit 910, input device 912 and UI navigation device 914 may be a touch screen display. The machine 900 may additionally include a storage device (e.g., drive unit) 916, a signal generation device 918 (e.g., a speaker), a network interface device 920, and one or more sensors 921, such as a global positioning system (GPS) sensor, compass, accelerometer, or other sensors. The machine 900 may include an output controller 928, such as a serial (e.g., universal serial bus (USB), parallel, or other wired or wireless (e.g., infrared (IR), near field communication (NFC), etc.) connection to communicate or control one or more peripheral devices (e.g., a printer, card reader, etc.).

The storage device 916 may include a machine readable medium 922 on which is stored one or more sets of data structures or instructions 924 (e.g., software) embodying or utilized by any one or more of the techniques or functions described herein. The instructions 924 may also reside, completely or at least partially, within the main memory 904, within static memory 906, or within the hardware processor 902 during execution thereof by the machine 900. In an example, one or any combination of the hardware processor 902, the main memory 904, the static memory 906, or the storage device 916 may constitute machine readable media.

While the machine-readable medium 922 is illustrated as a single medium, the term "machine readable medium" may include a single medium or multiple media (e.g., a centralized or distributed database, and/or associated caches and servers) configured to store the one or more instructions 924.

The term "machine readable medium" may include any medium that is capable of storing, encoding, or carrying instructions for execution by the machine 900 and that cause the machine 900 to perform any one or more of the techniques of the present disclosure, or that is capable of storing, encoding or carrying data structures used by or associated with such instructions. Non-limiting machine-readable medium examples may include solid-state memories, and optical and magnetic media. In an example, a massed machine-readable medium comprises a machine readable medium with a plurality of particles having invariant (e.g., rest) mass. Accordingly, massed machine-readable media are not transitory propagating signals. Specific examples of massed machine-readable media may include: non-volatile memory, such as semiconductor memory devices (e.g., Electrically Programmable Read-Only Memory (EPROM), Electrically Erasable Programmable Read-Only Memory (EPSOM)) and flash memory devices; magnetic disks, such as internal hard disks and removable disks; magneto-optical disks; and CD-ROM and DVD-ROM disks.

The instructions 924 may further be transmitted or received over a communication network 926 using a transmission medium via the network interface device 920 utilizing any one of a number of transfer protocols (e.g., frame relay, internet protocol (IP), transmission control protocol (TCP), user datagram protocol (UDP), hypertext transfer protocol (HTTP), etc.). Example communication networks may include a local area network (LAN), a wide area network (WAN), a packet data network (e.g., the Internet), mobile telephone networks (e.g., cellular networks), Plain Old Telephone (POTS) networks, and wireless data networks (e.g., Institute of Electrical and Electronics Engineers (IEEE) 802.11 family of standards known as WiFi®, IEEE 802.16 family of standards known as WiMax®), IEEE 802.15.4 family of standards, peer-to-peer (P2P) networks, among others. In an example, the network interface device 920 may include one or more physical jacks (e.g., Ethernet, coaxial, or phone jacks) or one or more antennas to connect to the communication network 926. In an example, the network interface device 920 may include a plurality of antennas to wirelessly communicate using at least one of single-input multiple-output (SIMO), multiple-input multiple-output (MIMO), or multiple-input single-output (MISO) techniques. The term "transmission medium" shall be taken to include any intangible medium that is capable of storing, encoding or carrying instructions for execution by the machine 900, and includes digital or analog communications signals or other intangible medium to facilitate communication of such software.

ADDITIONAL NOTES

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In this document, the terms “a” or “an” are used, as is common in patent documents, to include one or more than one, independent of any other instances or usages of “at least one” or “one or more.” In this document, the term “or” is used to refer to a nonexclusive or, such that “A or B” includes “A but not B,” “B but not A,” and “A and B,” unless otherwise indicated. In this document, the terms “including” and “in which” are used as the plain-English equivalents of the respective terms “comprising” and “wherein.” Also, in the following claims, the terms “including” and “comprising” are open-ended, that is, a system, device, article, composition, formulation, or process that includes elements in addition to those listed after such a term in a claim are still deemed to fall within the scope of that claim. Moreover, in the following claims, the terms “first,” “second,” and “third,” etc. are used merely as labels, and are not intended to impose numerical requirements on their objects.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

1. An endoscopic system, comprising:
   - a steerable elongate instrument configured to be positioned and navigated in a patient anatomy;
   - a processor configured to:
     - receive patient information including an image of an anatomical target; and
     - apply the received image of the anatomical target to at least one trained machine-learning (ML) model to (i) identify the anatomical target and a characteristic thereof, and (ii) generate a treatment plan for treating the anatomical target; and
   - a user interface configured to present the identified characteristic of the anatomical target and the generated treatment plan to a user.

2. The endoscopic system of example 1, further comprising a controller circuit configured to generate a control signal to an actuator to robotically facilitate operation of the steerable elongate instrument or a treatment tool associated therewith to treat the anatomical target in accordance with the generated treatment plan.

3. The endoscopic system of example 1, wherein the processor is configured to use the at least one trained ML model to identify the anatomical target as a calculi target, and to determine a characteristic including one or more of size, shape, hardness, or composition of the calculi target.

4. The endoscopic system of example 1, wherein the processor is configured to use the at least one trained ML model to identify the anatomical target as a tissue target, and to determine a characteristic including one or more of inflammation status, level of stricture, or malignancy state of the tissue target.

5. The endoscopic system of example 1, wherein the processor is configured to use the at least one trained ML model to generate the treatment plan including a recommended tool of a specific type or size for use in treating the anatomical target.

6. The endoscopic system of example 5, wherein the anatomical target includes a calculi target, and wherein the recommended tool includes one of a mechanical lithotripsy device, a laser lithotripsy device, or an electrohydraulic lithotripsy device for ablating or fragmenting the calculi target.

7. The endoscopic system of example 5, wherein the recommended tool includes one of a balloon, a basket, or a snare for extracting the anatomical target or a portion thereof.

8. The endoscopic system of example 5, wherein the processor is configured to determine the recommended tool further based on one or more of:
   - a position of the anatomical target;
   - spatial restrictions of an environment of the anatomical target, or
   - sizes or geometries of candidate tools for treating the anatomical target.

9. The endoscopic system of example 5, wherein the generated treatment plan further includes one or more operational parameters for using the recommended tool to treat the anatomical target.

10. The endoscopic system of example 9, wherein the anatomical target includes a calculi target, and wherein the one or more operational parameters include an energy output of a lithotripsy device for ablating or fragmenting the calculi target.

11. The endoscopic system of example 9, wherein the one or more operational parameters include a position, a heading direction, or an angle of at least a portion of the recommended tool with respect to the anatomical target.

12. The endoscopic system of example 9, wherein the one or more operational parameters include a navigation path for navigating the steerable elongate instrument or maneuvering the recommended tool with respect to the anatomical target.

13. The endoscopic system of example 1, wherein the anatomical target includes a calculi target, and wherein the processor is configured to use the at least one trained ML model to generate the treatment plan including a geometric location on the calculi target and an aiming angle or orientation of a laser lithotripsy device to direct laser energy at the geometric location to ablate or fragment the calculi target.

14. The endoscopic system of example 1, wherein the anatomical target includes a plurality of anatomical structures to be treated, and wherein the processor is configured to use the at least one trained ML model to generate the treatment plan including to determine an order of treating the plurality of structures.

15. The endoscopic system of example 1, wherein the processor is configured to use the at least one trained ML model to determine a probability of success or an estimate of treatment time in accordance with the generated treatment plan.

16. The endoscopic system of example 1, wherein the processor includes a training module configured to train an ML model using a training dataset comprising procedure data from past endoscopic procedures on a plurality of patients, the procedure data including (i) images of anatomical targets of the plurality of patients and (ii) identified characteristics of the anatomical targets and assessments of treatment plans for treating respective anatomical targets.

17. The endoscopic system of example 16, wherein the training module is configured to train the ML model using supervised learning or unsupervised learning.

18. The endoscopic system of example 1, wherein the anatomical target includes a plurality of targets, and wherein the user interface is configured to:
display images of the plurality of targets; and
responsive to a user selection of one of the plurality of targets, display the identified characteristic of the selected target and the generated treatment plan for treating the selected target.

19. A method of identifying an anatomical target and planning an endoscopic procedure via an endoscopic system, the method comprising:
providing patient information including an image of the anatomical target;
applying the image of the anatomical target to at least one trained machine-learning (ML) model to (i) identify the anatomical target and a characteristic thereof, and (ii) generate a treatment plan for treating the anatomical target; and
presenting the identified characteristic of the anatomical target and the generated treatment plan on a user interface.

20. The method of example 19, further comprising providing a control signal to an actuator to robotically facilitate operation of a steerable elongate instrument or a treatment tool associated therewith to treat the anatomical target in accordance with the generated treatment plan.

21. The method of example 19, wherein the identified target includes a calculi target, and the identified characteristic includes one or more of size, shape, hardness, or composition of the calculi target.

22. The method of example 19, wherein the identified anatomical target includes a tissue target, and the identified characteristic includes one or more of inflammation status, level of stricture, or malignancy state of the tissue target.

23. The method of example 19, wherein the generated treatment plan includes a recommended tool of a specific type or size for use in treating the anatomical target.

24. The method of example 23, wherein the recommended tool is determined further using one or more of:
a position of the anatomical target;
spatial restrictions of an environment of the anatomical target; or
sizes or geometries of candidate tools for treating the anatomical target.

25. The method of example 23, wherein the generated treatment plan further includes one or more operational parameters for using the recommended tool to treat the anatomical target.

26. The method of example 25, wherein the one or more operational parameters for using the recommended tool include:
an energy output of a lithotripsy device for ablating or fragmenting a calculi target;
a position, a heading direction, or an angle of at least a portion of the recommended tool with respect to the anatomical target; or
a navigation path for navigating a steerable elongate instrument or maneuvering the recommended tool with respect to the anatomical target.

27. The method of example 19, further comprising applying the image of the anatomical target to the at least one trained ML model to determine one or more of a probability of success or an estimate of treatment time in accordance with the generated treatment plan.

28. The method of example 19, further comprising, via a training module, training an ML model using a training dataset comprising procedure data from past endoscopic procedures on a plurality of patients, the procedure data including (i) images of anatomical targets of the plurality of patient and (ii) identified characteristics of the anatomical targets and assessments of treatment plans for treating respective anatomical targets.

29. The method of example 19, wherein the anatomical target includes a plurality of targets, the method further comprising:
displaying images of the plurality of targets on the user interface; and
responsive to a user selection of one of the plurality of targets, displaying the identified characteristic of the selected target and the generated treatment plan for treating the selected target.

FIELD OF THE DISCLOSURE

The present document relates generally to endoscopic systems, and more particularly to systems and methods for providing inter-facility content sharing and endoscopic procedure planning.

BACKGROUND

Endoscopes have been used in a variety of clinical procedures, including, for example, illuminating, imaging, detecting and diagnosing one or more disease states, providing fluid delivery (e.g., saline or other preparations via a fluid channel) toward an anatomical region, providing passage (e.g., via a working channel) of one or more therapeutic devices or biological matter collection devices for sampling or treating an anatomical region, and providing suction passageways for collecting fluids (e.g., saline or other preparations), among other procedures. Examples of such anatomical region can include gastrointestinal tract (e.g., esophagus, stomach, duodenum, pancreaticobiliary duct, intestines, colon, and the like), renal area (e.g., kidney(s), ureter, bladder, urethra) and other internal organs (e.g., reproductive systems, sinus cavities, submucosal regions, respiratory tract), and the like.

Some endoscopes include a working channel through which an operator can perform suction, placement of diagnostic or therapeutic devices (e.g., a brush, a biopsy needle or forceps, a stent, a basket, or a balloon), or minimally invasive surgeries such as tissue sampling or removal of unwanted tissue (e.g., benign or malignant strictures) or foreign objects (e.g., calculi). Some endoscopes can be used with a laser or plasma system to deliver energy to an anatomical target (e.g., soft or hard tissue or calculi) to achieve desired treatment. For example, laser has been used in applications of tissue ablation, coagulation, vaporization, fragmentation, and lithotripsy to break down calculi in kidney, gallbladder, ureter, among other stone-forming regions, or to ablate large calculi into smaller fragments.

In conventional endoscopy, the distal portion of the endoscope can be configured for supporting and orienting a therapeutic device, such as with the use of an elevator. In some systems, two endoscopes can work together with a first endoscope guiding a second endoscope inserted therein with the aid of the elevator. Such systems can be helpful in guiding endoscopes to anatomic locations within the body that are difficult to reach. For example, some anatomic locations can only be accessed with an endoscope after insertion through a circuitous path.

Peroral cholangioscopy is a technique that permits direct endoscopic visualization, diagnosis, and treatment of various disorders of patient biliary and pancreatic ductal system using miniature endoscopes and catheters inserted through the accessory port of a duodenoscope. Peroral cholangioscopy can be performed by using a dedicated cholangioscope that is advanced through the accessory channel of a duodenoscope, as used in Endoscopic Retrograde Cholangio-Pancreatography (ERCP) procedures. ERCP is a technique that combines the use of endoscopy and fluoroscopy to diagnose and treat certain problems of the biliary or pancreatic ductal systems, including the liver, gallbladder, bile ducts, pancreas, or pancreatic duct. In ERCP, a cholangioscope (also referred to as an auxiliary scope, or a "daughter" scope) can be attached to and advanced through a working channel of a duodenoscope (also referred to as a main scope, or a "mother" scope). Typically, two separate endoscopists operate each of the "mother-daughter" scopes. Although biliary cannulation can be achieved directly with the tip of the cholangioscope, most endoscopists prefer cannulation over a guidewire. A tissue retrieval device can be inserted through the cholangioscope to retrieve biological matter (e.g., gallstones, bill duct stones, cancerous tissue) or to manage stricture or blockage in bile duct.

Peroral cholangioscopy can also be performed by inserting a small-diameter dedicated endoscope directly into the bile duct, such as in a Direct PerOral Cholangioscopy (DPOC) procedure. In DPOC, a slim endoscope (cholangioscope) can be inserted into patient mouth, pass through the upper GI tract, and enter into the common bile duct for visualization, diagnosis, and treatment of disorders of the biliary and pancreatic ductal systems.

SUMMARY

For complex endoscopic procedures like ERCP, success rate and patient outcome can be affected by several factors including availability of advanced diagnostic and surgical devices or tools, and experiences and skills of operating physicians and other healthcare professionals. For example, in ERCP procedures, as the duodenoscope, the cholangioscope, and the tissue retrieval device become progressively smaller due to being inserted sequentially in progressively smaller lumens, it has become more difficult to maneuver and navigate the endoscope through the patient anatomy, maintain endoscope stabilization, and maintain correct cannulation position in a narrow space (e.g., the bile duct). Cannulation and endoscope navigation in patients with surgically altered or otherwise difficult anatomies generally require more advanced surgical skills and manual dexterity, which can be particularly challenging for less-experienced operating physicians.

Medical facilities vary in their medical resources and levels of experiences and skills with complex procedures like ERCP, especially for treating patients with difficult or surgically altered anatomies. Compared to large "center" hospitals, smaller "peripheral" or regional hospitals generally lack adequate medical resources and required expertise in ERCP, along with other constraints. Some patients initially treated (or scheduled to be treated) at a peripheral hospital may be referred to a large center hospital for further evaluation or treatment. The inter-facility variations in handling complex endoscopic procedures may affect overall success rate and patient outcome across patient population.

This document describes an improved solution to address the challenges particularly faced by medical facilities with insufficient medical resources, experiences, knowledge base, and skillset to perform complex endoscopic procedures like ERCP. One aspect of the improved solution described herein includes an inter-facility procedure planning platform that provides content sharing and cooperative procedure planning and scheduling between a center hospital and one or more peripheral hospitals. According to one embodiment, an endoscopic procedure planning system comprises a plurality of networked devices, including at least one first computing and storage device accessible by respective at least one first facility, and a second computing and storage device accessible by a second facility having more advanced medical resources than the at least one first facility. The at least one first computing and storage device can collect and store therein procedure data associated with endoscopic procedures scheduled or performed at the at least one first facility. The at least one first computing and storage device can transmit at least a portion of the procedure data to the second computing and storage device via a communication network. The second computing and storage device can generate an endoscopic procedure recommendation using the procedure data received from the at least one first facility and the more advanced medical resources available to the second facility, and send the endoscopic procedure recommendation to the at least one first computing and storage device to facilitate an endoscopic procedure therein.

Example 1 is a system for providing inter-facility content sharing and endoscopic procedure planning, the system comprising: a plurality of networked devices, including (i) at least one first computing and storage device accessible by respective at least one first facility and (ii) a second computing and storage device accessible by a second facility having more advanced medical resources than the at least one first facility; wherein the at least one first computing and storage device is configured to collect and store therein procedure data associated with endoscopic procedures scheduled or performed at the at least one first facility, and to transmit at least a portion of the procedure data to the second computing and storage device via a communication network; wherein the second computing and storage device is configured to: generate an endoscopic procedure recommendation using (i) the at least a portion of the procedure data received from the at least one first facility and (ii) the more advanced medical resources of the second facility; and send, via the communication network, the generated endoscopic procedure recommendation to the at least one first computing and storage device to facilitate an endoscopic procedure therein.

In Example 2, the subject matter of Example 1 optionally includes the procedure data collected at the at least one first facility that can include data collected from an endoscopic cholangiopancreatography (ERCP) procedure, and the generated endoscopic procedure recommendation includes a recommended ERCP procedure plan for the at least one first facility.

In Example 3, the subject matter of any one or more of Examples 1-2 optionally includes the at least a portion of the procedure data that can include preoperative or perioperative images of patient anatomy collected from the endoscopic procedures scheduled or performed at the at least one first facility.

In Example 4, the subject matter of Example 3 optionally includes the second computing and storage device that can be configured to reconstruct a three-dimensional (3D) patient anatomy image using the preoperative or perioperative images of patient anatomy received from the at least one first facility, and to generate the endoscopic procedure recommendation further using the reconstructed 3D patient anatomy image.

In Example 5, the subject matter of any one or more of Examples 1-4 optionally includes the at least a portion of the procedure data that can include endoscopic surgical device information associated with the endoscopic procedures performed at the at least one first facility.

In Example 6, the subject matter of any one or more of Examples 1-5 optionally includes the at least a portion of the procedure data that can include data collected from one or more failed endoscopic procedures performed at the at least one first facility.

In Example 7, the subject matter of any one or more of Examples 1-6 optionally includes the at least a portion of the procedure data that can include pre- or perioperative data collected from one or more patients identified based on their respective anatomies and medical record.

In Example 8, the subject matter of any one or more of Examples 1-7 optionally includes the endoscopic procedure recommendation that can include a device recommendation to be used in an endoscopic procedure.

In Example 9, the subject matter of any one or more of Examples 1-8 optionally includes the endoscopic procedure recommendation that can include respective values of one or more cannulation or navigation parameters for maneuvering an endoscopic device.

In Example 10, the subject matter of any one or more of Examples 1-9 optionally includes the endoscopic procedure recommendation that can include a follow-up procedure plan.

In Example 11, the subject matter of Example 10 optionally includes the follow-up procedure plan that can include a recommended facility and schedule for a follow-up procedure.

In Example 12, the subject matter of any one or more of Examples 10-11 optionally includes the follow-up procedure plan that can include a follow-up endoscopic procedure at the second facility, wherein the second computing and storage device is further configured to collect follow-up procedure data, and to communicate the follow-up procedure data to the at least one first computing and storage device.

In Example 13, the subject matter of any one or more of Examples 1-12 optionally includes the second computing and storage device that can be further configured to generate educational information about anatomies and endoscopic procedures, and to send the educational information to the at least one first computing and storage device via the communication network.

In Example 14, the subject matter of any one or more of Examples 1-13 optionally includes the second computing and storage device that can be further configured to: generate patient diagnostics or post-operative risk assessment; and send, via the communication network, the generated patient diagnostics or post-operative risk assessment to the at least one first computing and storage device to facilitate the endoscopic procedure therein.

In Example 15, the subject matter of any one or more of Examples 1-14 optionally includes the plurality of networked devices that can include two or more first computing and storage devices each communicatively connected to the second computing and storage devices and configured to transmit respective portions of procedure data to the second computing and storage device, wherein the second computing and storage device is configured to: generate the endoscopic procedure recommendation further using the procedure data received respectively from the two or more first computing and storage devices; and send the generated endoscopic procedure recommendation to at least one of the two or more first computing and storage devices to facilitate the endoscopic procedure therein.

Example 16 is a method for providing inter-facility content sharing and planning an endoscopic procedure between (i) at least one first computing and storage device accessible by respective at least one first facility and (ii) a second computing and storage device accessible by a second facility having more advanced medical resources than the at least one first facility, the method comprising: establishing a communication between the at least one first computing and storage device and the second computing and storage device; transmitting at least a portion of procedure data collected by and stored in the at least one first computing and storage device to the second computing and storage device, the procedure data associated with endoscopic procedures scheduled or performed at the at least one first facility; generating, via the second computing and storage device, an endoscopic procedure recommendation using (i) the at least a portion of the procedure data received from the at least first facility and (ii) the more advanced medical resources of the second facility; and sending the generated endoscopic procedure recommendation to the at least one first computing and storage device to facilitate an endoscopic procedure therein.

In Example 17, the subject matter of Example 16 optionally includes the at least a portion of the procedure data that can include preoperative or perioperative images of patient anatomy collected from the endoscopic procedures scheduled or performed at the at least one first facility.

In Example 18, the subject matter of Example 17 optionally includes reconstructing, via the second computing and storage device, a three-dimensional (3D) patient anatomy image using the preoperative or perioperative images of patient anatomy received from the at least one first facility, wherein generating the endoscopic procedure recommendation includes further using the reconstructed 3D patient anatomy image.

In Example 19, the subject matter of any one or more of Examples 16-18 optionally includes the at least a portion of the procedure data that can include endoscopic surgical device information associated with the endoscopic procedures performed at the at least one first facility.

In Example 20, the subject matter of any one or more of Examples 16-19 optionally includes the at least a portion of the procedure data that can include data collected from one or more failed endoscopic procedures performed at the at least one first facility.

In Example 21, the subject matter of any one or more of Examples 16-20 optionally includes the at least a portion of the procedure data that can include pre- or peri-operative data collected from one or more patients identified based on their respective anatomies and medical record.

In Example 22, the subject matter of any one or more of Examples 16-21 optionally includes the endoscopic procedure recommendation that can include one or more of: a device recommendation to be used in an endoscopic procedure; respective values of one or more cannulation or navigation parameters for maneuvering an endoscopic device; or a follow-up procedure plan.

In Example 23, the subject matter of any one or more of Examples 16-22 optionally includes, via the second computing and storage device: generating educational information about anatomies and endoscopic procedures; and sending the educational information to the at least one first computing and storage device.

In Example 24, the subject matter of any one or more of Examples 16-23 optionally includes, via the second computing and storage device: generating patient diagnostics or post-operative risk assessment; and sending the generated patient diagnostics or post-operative risk assessment to the at least one first computing and storage device to facilitate the endoscopic procedure therein.

The systems and methods of inter-facility endoscopic procedure planning as discussed herein can help ensure more effective and timely treatment of patients in regional hospitals lacking adequate resources and expertise in ERCP. This can be particularly helpful for those patients with surgically altered anatomies that require more sophisticated equipment and tools and more advanced surgical skills. The endoscopic procedure planning can be used by physicians of different experience levels, and help reduce the burden for manual surgical planning, and improve the prognostic predictability of the endoscopic procedures. Using the inter-facility endoscopic procedure planning platform discussed herein can help improve the treatment quality, patient safety, and overall success rate of endoscopic procedures across medical facilities.

The presented techniques are described in terms of health-related procedures, but are not so limited. This summary is an overview of some of the teachings of the present application and not intended to be an exclusive or exhaustive treatment of the present subject matter. Further details about the present subject matter are found in the detailed description and appended claims. Other aspects of the disclosure will be apparent to persons skilled in the art upon reading and understanding the following detailed description and viewing the drawings that form a part thereof, each of which are not to be taken in a limiting sense. The scope of the present disclosure is defined by the appended claims and their legal equivalents.

BRIEF DESCRIPTION OF THE DRAWING

Figure 10:
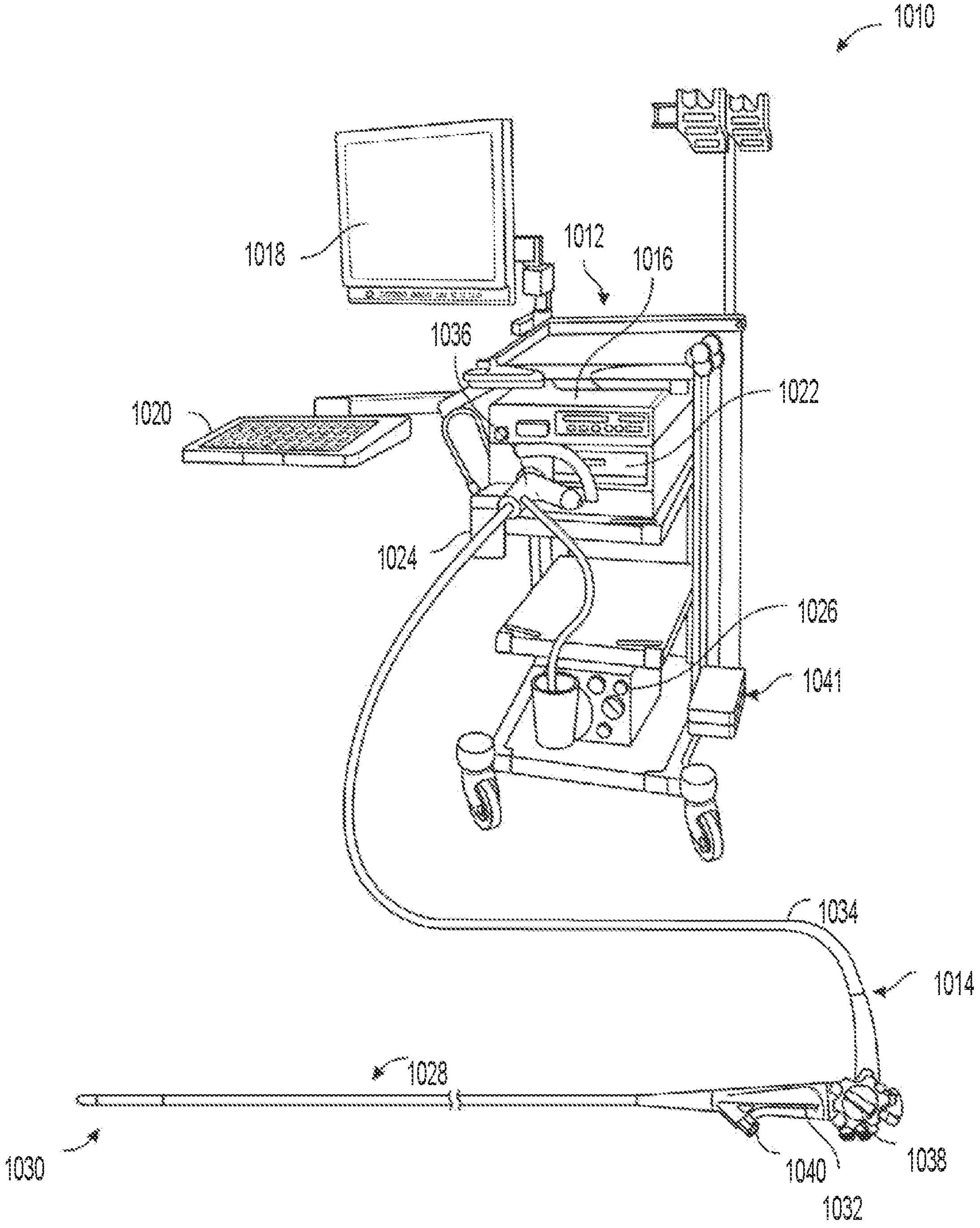
Figure 11:
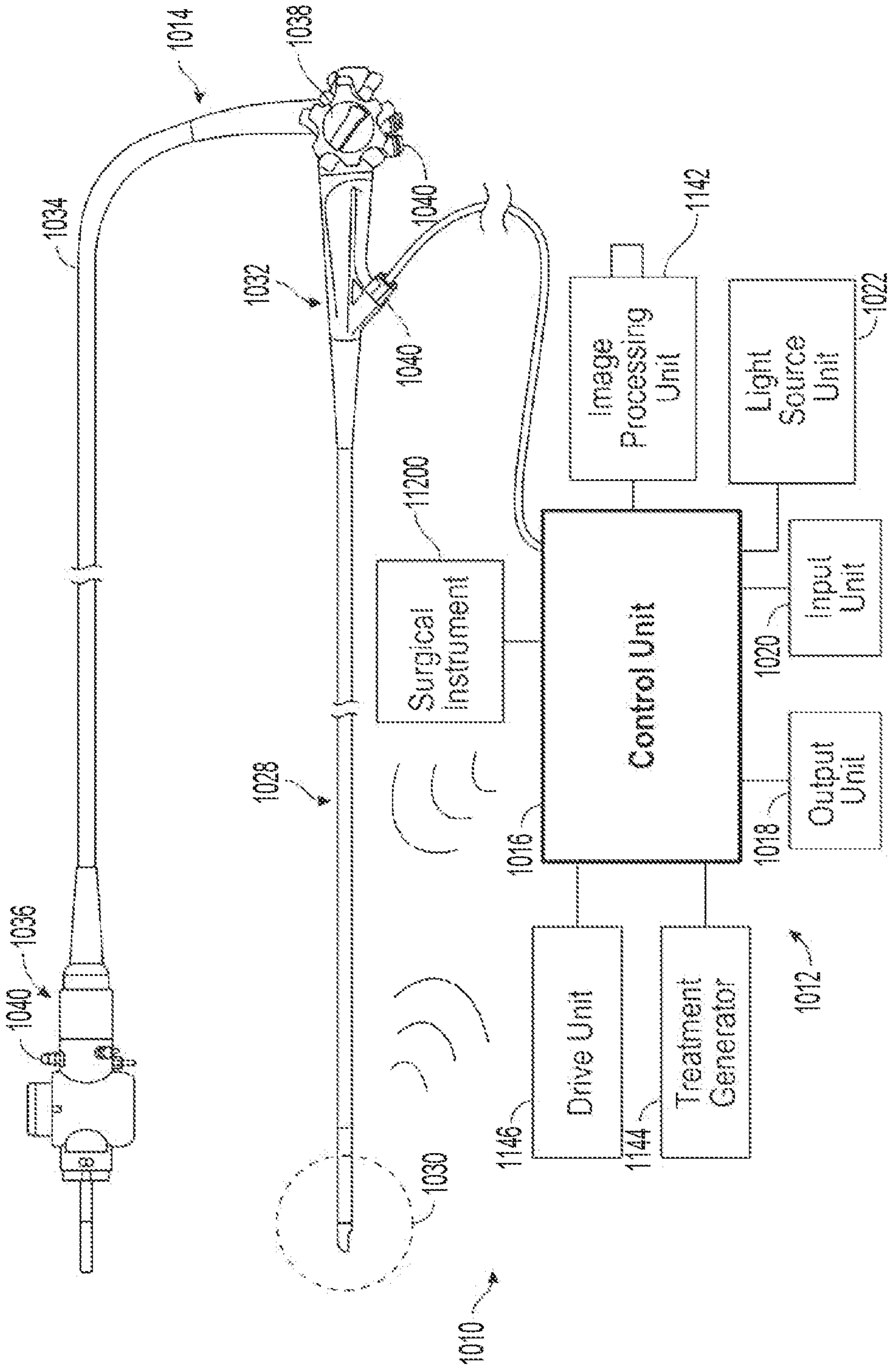

FIGS. 10-11 are schematic diagrams illustrating an example of an endoscopy system for use in endoscopic procedures such as an ERCP procedure.

Figure 12A:
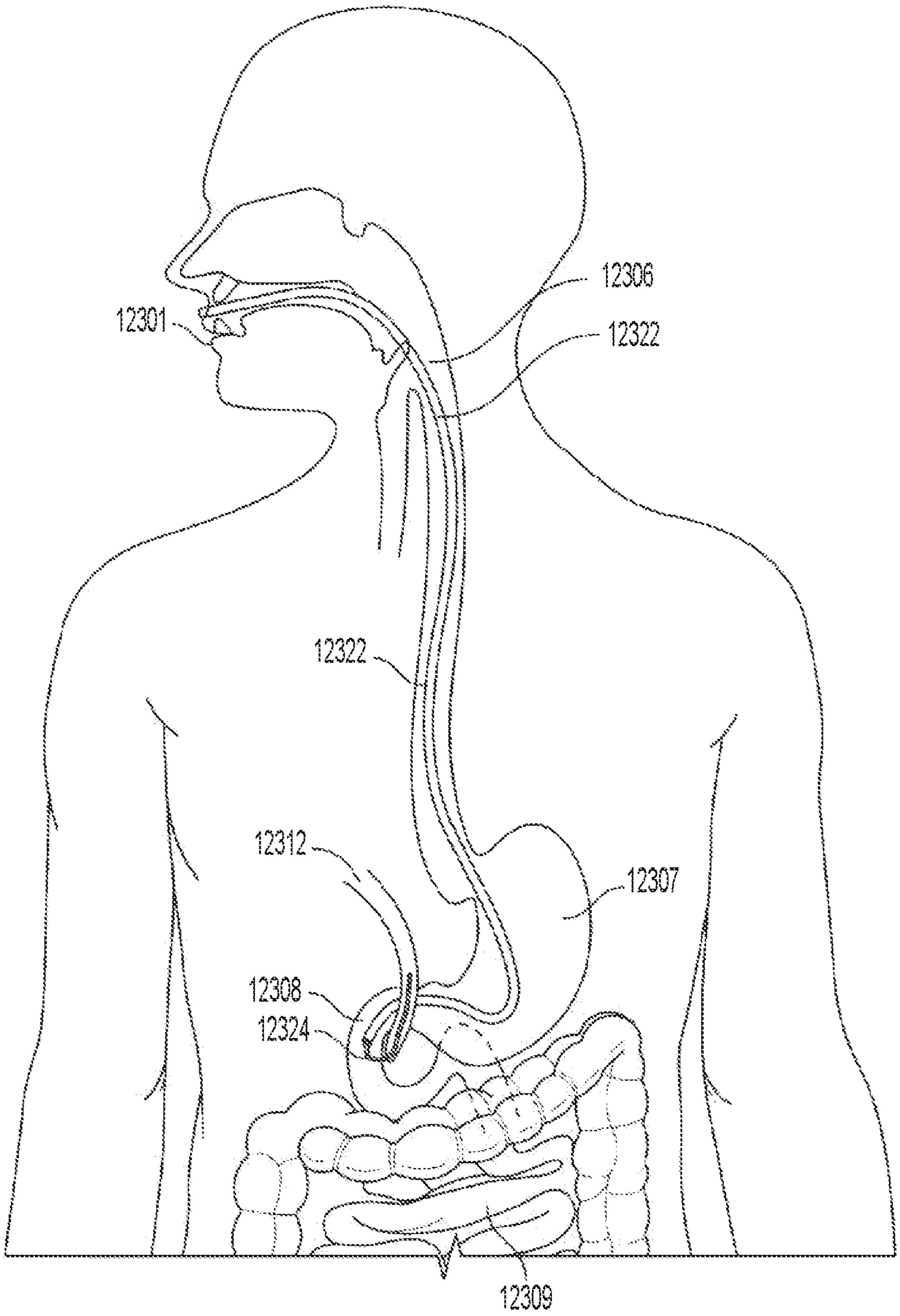
Figure 12B:
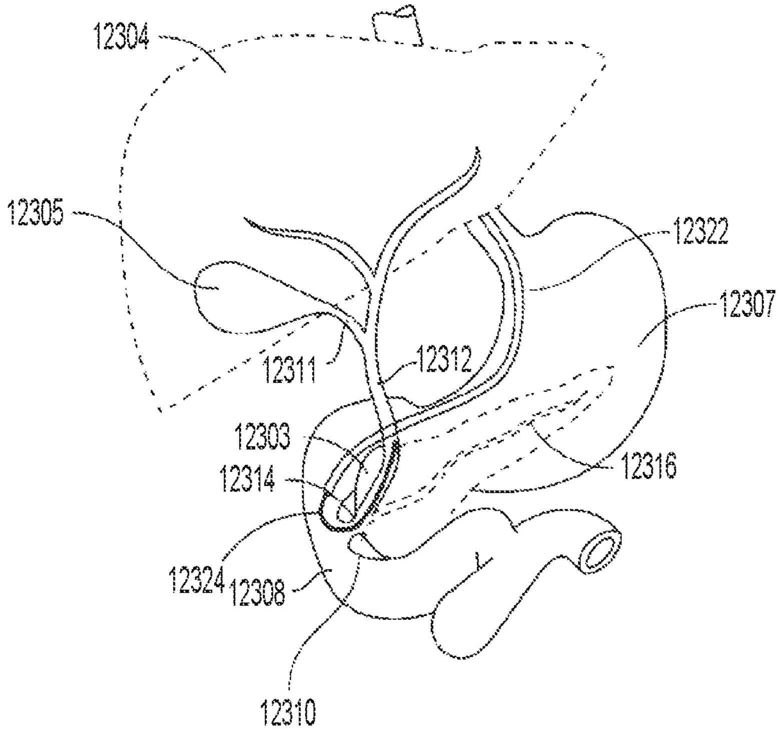

FIGS. 12A-12B are diagrams illustrating an example of peroral cholangioscopy involving direct insertion of a cholangioscope into patient bile duct as in a DPOC procedure, and a portion of patient anatomy where the procedure is performed.

Figure 13:
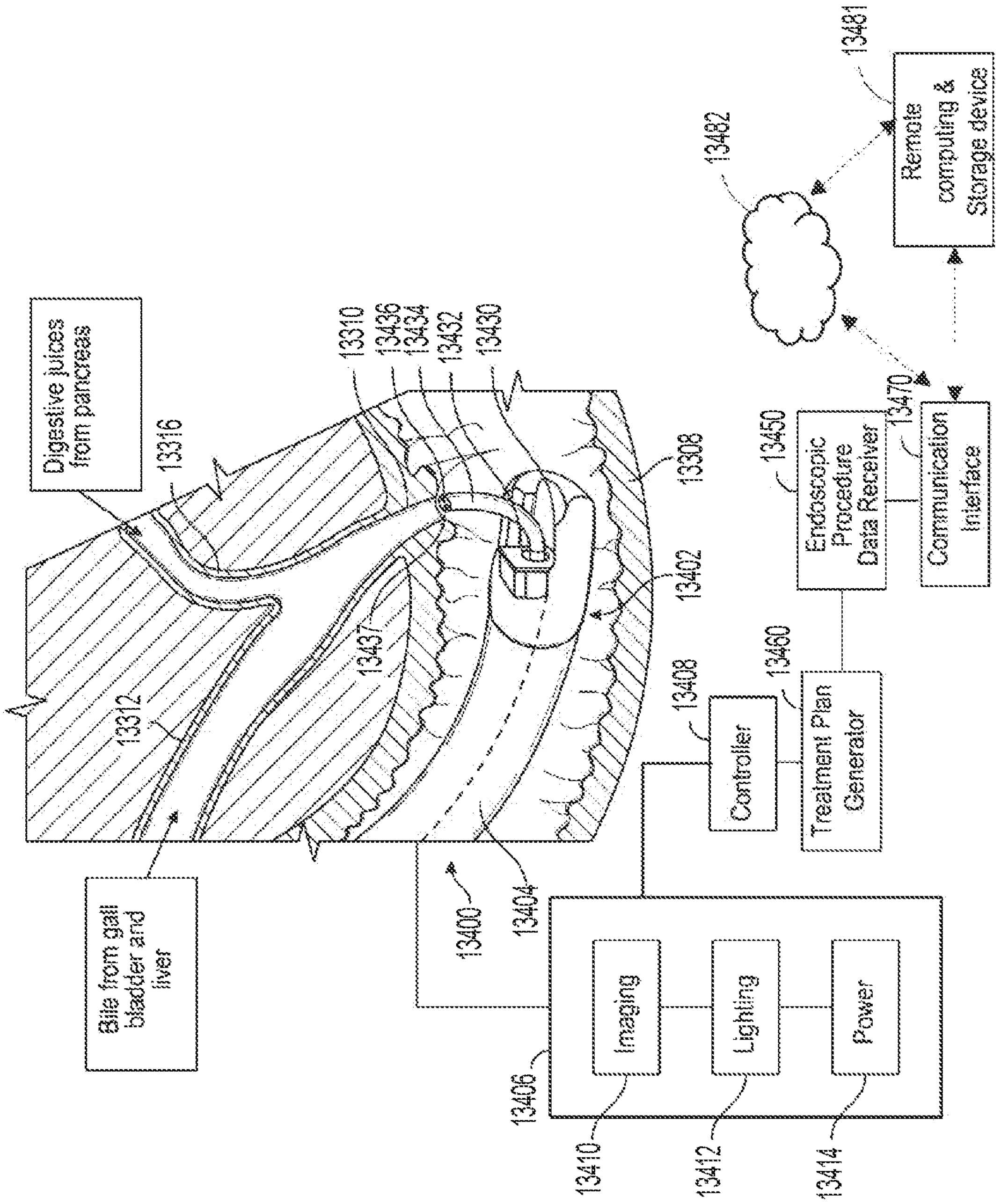

FIG. 13 is a diagram illustrating an example of mother-daughter endoscopes used in ERCP and a portion of patient anatomy of the procedure site.

Figure 14:
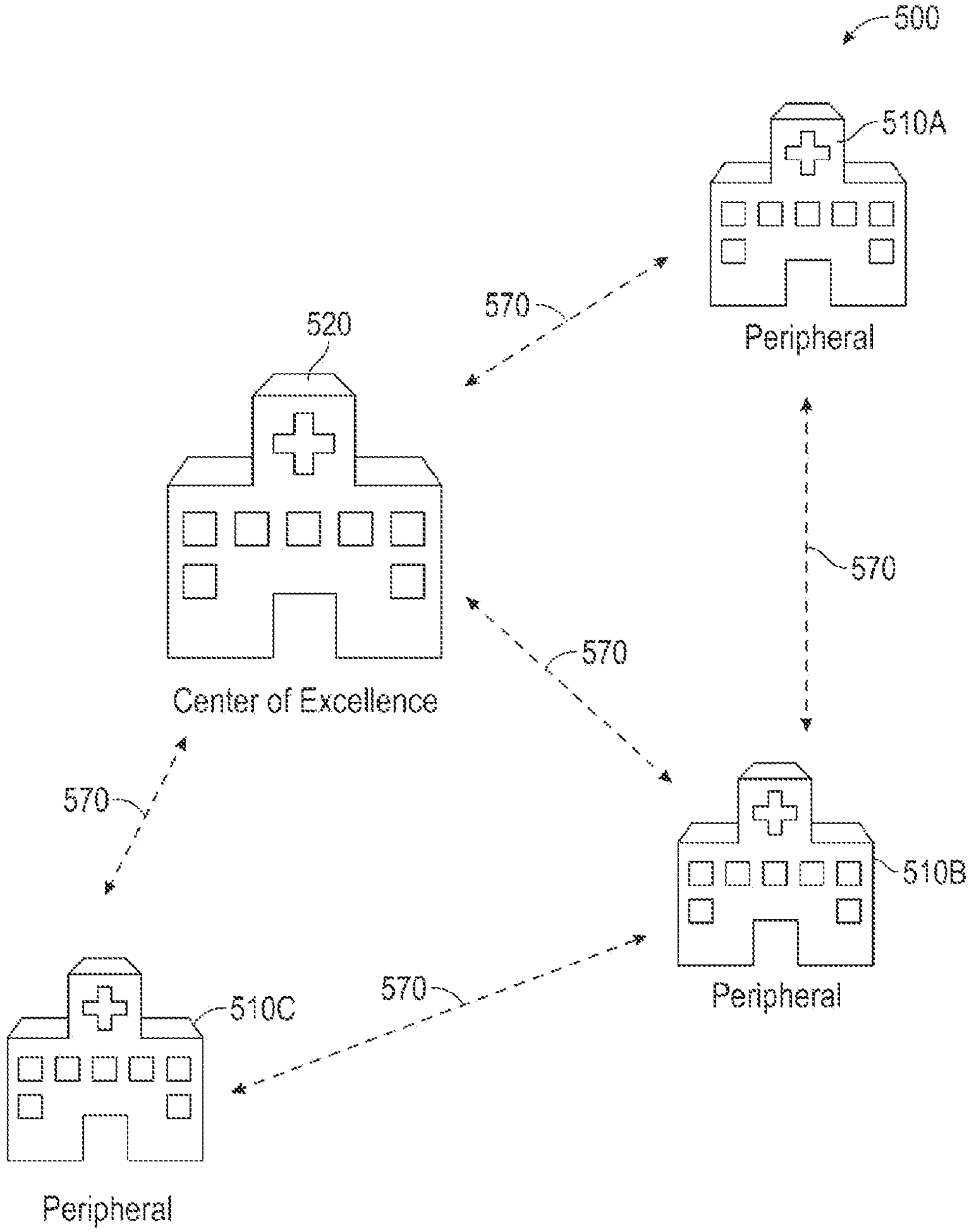

FIG. 14 is a diagram illustrating an example of an inter-facility content sharing and endoscopic procedure planning system.

Figure 15:
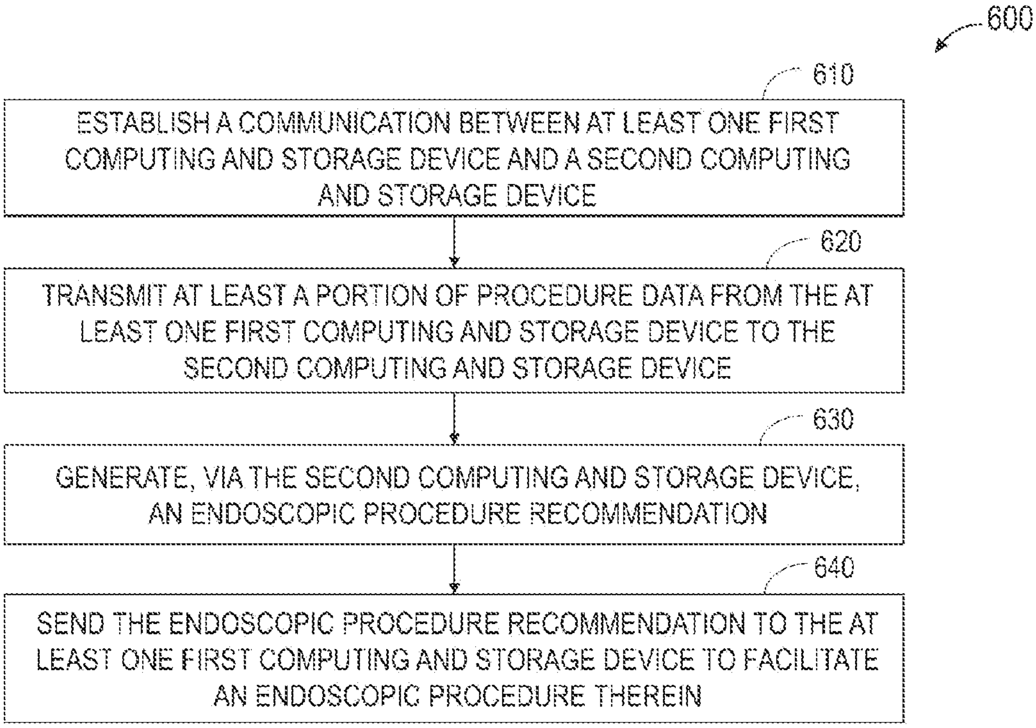

FIG. 15 is a flow chart illustrating an example method for providing inter-facility content sharing and planning an endoscopic procedure.

Figure 16:
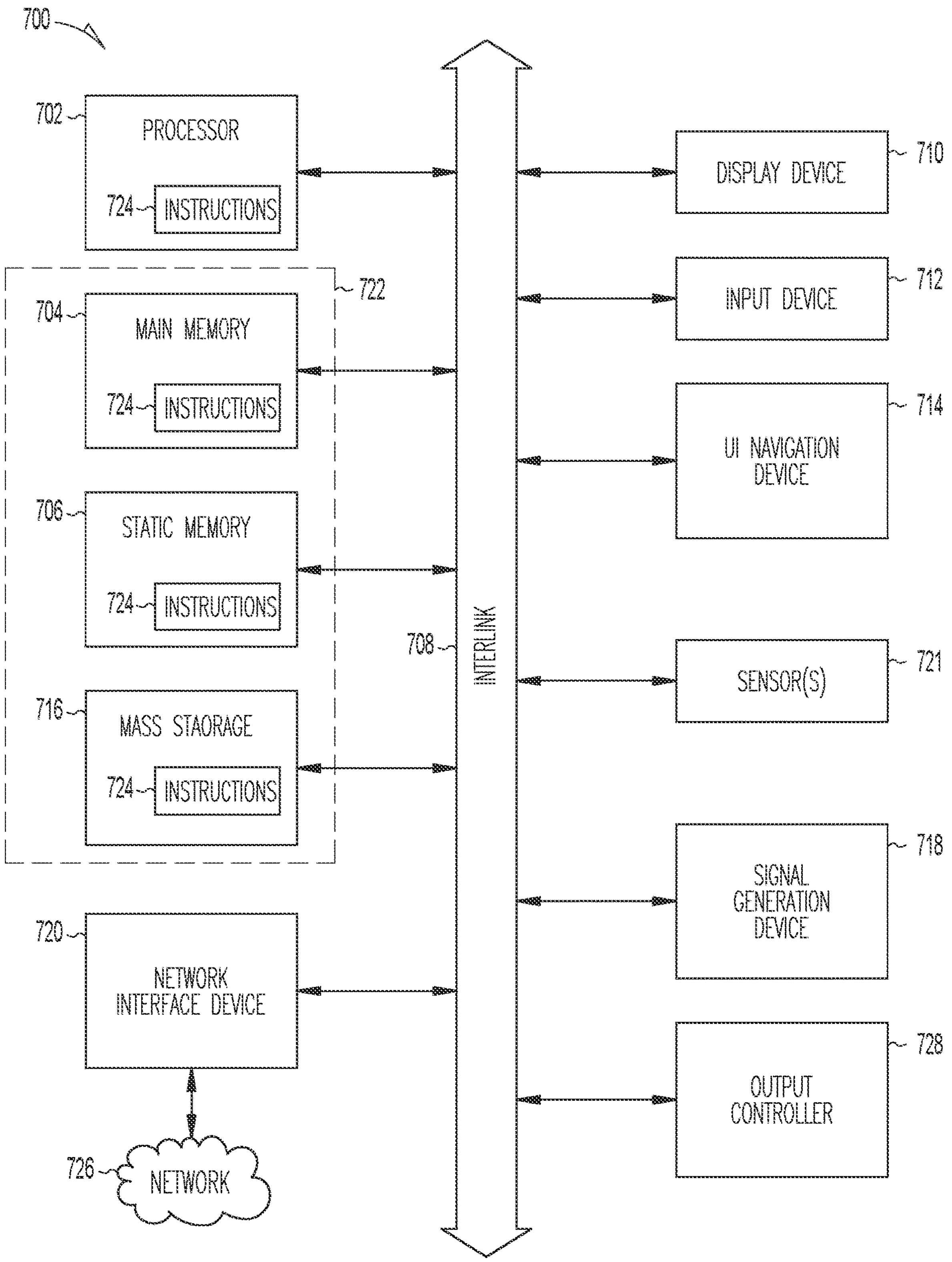

FIG. 16 is a block diagram illustrating an example machine upon which any one or more of the techniques (e.g., methodologies) discussed herein may perform.

DETAILED DESCRIPTION

This document describes systems, devices, and methods for providing inter-facility content sharing and efficiency of endoscopic procedure planning. According to one embodiment, an endoscopic procedure planning system comprises a plurality of networked devices, including at least one first computing and storage device accessible by respective at least one first facility, and a second computing and storage device accessible by a second facility having more advanced medical resources than the at least one first facility. The at least one first computing and storage device can collect and store therein procedure data associated with endoscopic procedures scheduled or performed at the at least one first facility. The at least one first computing and storage device can transmit at least a portion of the procedure data to the second computing and storage device. The second computing and storage device can generate an endoscopic procedure recommendation using the received procedure data and the more advanced medical resources, and send the endoscopic procedure recommendation to the at least one first computing and storage device to facilitate an endoscopic procedure therein.

FIG. 10 is a schematic diagram illustrating an example of an endoscopy system 10 for use in endoscopic procedures, such as an ERCP procedure. The system 1010 comprises an imaging and control system 1012 and an endoscope 1014. The endoscopy system 1010 is an illustrative example of an endoscopy system suitable for patient diagnosis and/or treatment using the systems, devices and methods described herein, such as tethered and optically enhanced biological matter and tissue collection, retrieval and storage devices and biopsy instruments that can be used for obtaining samples of tissue or other biological matter to be removed from a patient for analysis or treatment of the patient. According to some examples, the endoscope 1014 can be insertable into an anatomical region for imaging and/or to provide passage of or attachment to (e.g., via tethering) one or more sampling devices for biopsies, or one or more therapeutic devices for treatment of a disease state associated with the anatomical region.

The imaging and control system 1012 can comprise a control unit 1016, an output unit 1018, an input unit 1020, a light source 1022, a fluid source 1024, and a suction pump 1026. The imaging and control system 1012 can include various ports for coupling with endoscopy system 1010. For example, the control unit 1016 can include a data input/output port for receiving data from and communicating data to the endoscope 1014. The light source 1022 can include an output port for transmitting light to the endoscope 1014, such as via a fiber optic link. The fluid source 1024 can comprise one or more sources of air, saline or other fluids, as well as associated fluid pathways (e.g., air channels, irrigation channels, suction channels) and connectors (barb fittings, fluid seals, valves and the like). The fluid source 1024 can be in communication with the control unit 1016, and can transmit one or more sources of air or fluids to the endoscope 1014 via a port. The fluid source 1024 can comprise a pump and a tank of fluid or can be connected to an external tank, vessel or storage unit. The suction pump 1026 can comprise a port used to draw a vacuum from the endoscope 1014 to generate suction, such as for withdrawing fluid from the anatomical region into which the endoscope 1014 is inserted.

The output unit 1018 and the input unit 1020 can be used by a human operator and/or a robotic operator of endoscopy system 1010 to control functions of endoscopy system 1010 and view output of the endoscope 1014. In some examples, the control unit 1016 can additionally be used to generate signals or other outputs for treating the anatomical region into which the endoscope 1014 is inserted. Examples of such signals or outputs can include electrical output, acoustic output, a radio-frequency energy output, a fluid output and the like for treating the anatomical region with, for example, cauterizing, cutting, freezing and the like.

The endoscope 1014 can interface with and connect to the imaging and control system 1012 via a coupler section 1036. In the illustrated example, the endoscope 1014 comprises a duodenoscope that may be use in a ERCP procedure, though other types of endoscopes can be used with the features and teachings of the present disclosure. The endoscope 1014 can comprise an insertion section 1028, a functional section 1030, and a handle section 1032, which can be coupled to a cable section 1034 and the coupler section 1036.

The insertion section 1028 can extend distally from the handle section 1032, and the cable section 1034 can extend proximally from the handle section 1032. The insertion section 1028 can be elongate and include a bending section, and a distal end to which functional section 1030 can be attached. The bending section can be controllable (e.g., by control knob 1038 on the handle section 1032) to maneuver the distal end through tortuous anatomical passageways (e.g., stomach, duodenum, kidney, ureter, etc.). Insertion section 1028 can also include one or more working channels (e.g., an internal lumen) that can be elongate and support insertion of one or more therapeutic tools of functional section 1030, such as a cholangioscope as shown in FIG. 13. The working channel can extend between handle section 1032 and functional section 1030. Additional functionalities, such as fluid passages, guide wires, and pull wires can also be provided by insertion section 1028 (e.g., via suction or irrigation passageways, and the like).

The handle section 32 can comprise a control knob 1038 and ports 1040. The ports 1040 can be configured to couple various electrical cables, guide wires, auxiliary scopes, tissue collection devices of the present disclosure, fluid tubes and the like to handle section 1032 for coupling with insertion section 1028. The control knob 1038 can be coupled to a pull wire, or other actuation mechanisms, extending through insertion section 1028. The control knob 1038 can be used by a user to manually advance or retreat the insertion section 1028 of the endoscope 1014, and to adjust bending of a bending section at the distal end of the insertion section 1028. In some examples, an optional drive unit 1146 (FIG. 11) can be used to provide motorized drive for advancing a distal section of endoscope 1014 under the control of the control unit 1016.

The imaging and control system 1012, according to examples, can be provided on a mobile platform (e.g., cart 1041) with shelves for housing light source 1022, suction pump 1026, image processing unit 1142 (FIG. 11), etc. Alternatively, several components of the imaging and control system 1012 shown in FIGS. 10 and 11 can be provided directly on the endoscope 1014 such that the endoscope is "self-contained."

The functional section 1030 can comprise components for treating and diagnosing anatomy of a patient. The functional section 1030 can comprise an imaging device, an illumination device, and an elevator. The functional section 1030 can further comprise optically enhanced biological matter and tissue collection and retrieval devices. For example, the functional section 1030 can comprise one or more electrodes conductively connected to handle section 32 and functionally connected to the imaging and control system 1012 to analyze biological matter in contact with the electrodes based on comparative biological data stored in the imaging and control system 1012. In other examples, the functional section 1030 can directly incorporate tissue collectors.

In some examples, the endoscope 1014 can be robotically controlled, such as by a robot arm attached thereto. The robot arm can automatically, or semi-automatically (e.g., with certain user manual control or commands), via an actuator, position and navigate instrument such as the endoscope 1014 (e.g., the functional section 1030 and/or the insertion section 1028) of in the target anatomy, or position a device at a desired location with desired posture to facilitate an operation of an anatomical target, such as a basket, a balloon, or a snare for removing biliary ductal calculi. In accordance with various examples discussed in this document, a controller can use artificial intelligence (AI) to determine cannulation and navigation parameters and/or tool operational parameters (e.g., position, angle, posture, force, and navigation path), and generate a control signal to the actuator of the robot arm to facilitate operation of such instrument or tools in accordance with the determined navigation and operational parameters in a robotically assisted procedure.

FIG. 11 is a schematic diagram of the endoscopy system 1010 shown in FIG. 10, which comprises the imaging and control system 1012 and the endoscope 1014. FIG. 11 schematically illustrates components of the imaging and control system 12 coupled to the endoscope 1014, which in the illustrated example comprises a duodenoscope. The imaging and control system 1012 can comprise a control unit 1016, which can include or be coupled to an image processing unit 1142, a treatment generator 1144, and a drive unit 1146, as well as the light source 1022, the input unit 1020, and the output unit 1018 as discussed above with reference to FIG. 10. The control unit 1016 can comprise, or can be in communication with, a surgical instrument 11200 comprising a device configured to engage tissue and collect and store a portion of that tissue and through which an imaging device (e.g., a camera) can view target tissue via inclusion of optically enhanced materials and components. The control unit 1016 can be configured to activate an imaging device (e.g., a camera) at the functional section of the endoscope 1014 to view target tissue distal of surgical instrument 200 and endoscopy system 1010, which can be fabricated of a translucent material to minimize the impacts of the camera being obstructed or partially obstructed by the tissue retrieval device. Likewise, the control unit 1016 can be configured to activate the light source 1022 to shine light on the surgical instrument 11200, which can include select components that are configured to reflect light in a particular manner, such as tissue cutters being enhanced with reflective particles.

The image processing unit 1142 and the light source 1022 can each interface with the endoscope 1014 (e.g., at the functional section 1030) by wired or wireless electrical connections. The imaging and control system 1012 can accordingly illuminate an anatomical region using the light source 1022, collect signals representing the anatomical region, process signals representing the anatomical region using the image processing unit 1142, and display images representing the anatomical region on the output unit 1018. The imaging and control system 1012 can include the light source 1022 to illuminate the anatomical region using light of desired spectrum (e.g., broadband white light, narrow-band imaging using preferred electromagnetic wavelengths, and the like). The imaging and control system 1012 can connect (e.g., via an endoscope connector) to the endoscope 1014 for signal transmission (e.g., light output from light source, video signals from the imaging device such as positioned at the distal portion of the endoscope 1014, diagnostic and sensor signals from a diagnostic device, and the like).

The treatment generator 1144 can generate a treatment plan, which can be used by the control unit 1016 to control the operation of the endoscope 1014, or to provide with the operating physician a guidance for maneuvering the endoscope 1014, during an endoscopic procedure. In an example, the treatment generator 1144 can generate an endoscope navigation plan, including estimated values for one or more cannulation or navigation parameters (e.g., an angle, a force, etc.) for maneuvering the steerable elongate instrument, using patient information including an image of the target anatomy. The endoscope navigation plan can help guide the operating physician to cannulate and navigate the endoscope in the patient anatomy. The endoscope navigation plan may additionally or alternatively be used to robotically adjust the position, angle, force, and/or navigation of the endoscope or other instrument.

FIGS. 12A-12B are diagrams illustrating an example of peroral cholangioscopy performed via direct insertion of a cholangioscope 12324 into the bile duct, as in a DPOC procedure, and a portion of patient anatomy where the procedure is performed. The cholangioscope 12324 is nested inside of a guide sheath 12322, and inserted perorally into a patient to reach duodenum 12308. Duodenum 12308 comprises an upper part of the small intestine. The guide sheath 12322 can extend into mouth 12301, through esophagus 12306, through stomach 12307 to reach the duodenum 12308. Before reaching intestines 12309, the guide sheath 12322 can position the cholangioscope 12324 proximate common bile duct 12312. The common bile duct 12312 carries bile from the gallbladder 12305 and liver 12304, and empties the bile into the duodenum 12308 through sphincter of Oddi 12310 (FIG. 12B). The cholangioscope 12324 can extend from guide sheath 12322 to extend into common bile duct 12312. In some examples, steering features of guide sheath 12322 (e.g., pull wire) can be used to facilitate navigating and bending of cholangioscope 12324 through stomach 12307, in addition to direct steering of cholangioscope 12324 via the pull wires. For example, navigation of the Pyloric canal and Pyloric sphincter can be difficult to navigate using only an endoscope. Thus, the guide sheath 12322 can be used to turn or bend elongate body of cholangioscope 12324, or reduce the amount of steering or bending of the elongate body of the cholangioscope 12324 required by pull wires, to facilitate traversing the Pyloric sphincter.

FIG. 12B is a schematic view of duodenum 12308 connected to common bile duct 12312 via duodenal papilla 12314. Common bile duct 12312 can branch off into pancreatic duct 12316 and gallbladder duct 12311. Duodenal papilla 12314 can include sphincter of Oddi 12310 that controls flow of bile and pancreatic juice into the intestine (duodenum). Pancreatic duct 12316 can lead to pancreas 12303. Pancreatic duct 12316 carries pancreatic juice from pancreas 12303 to the common bile duct 12312. Gallbladder duct 12311 can lead to gallbladder 12305. In some patients, it can be difficult to navigate surgical instruments to duodenal papilla 12314. It can also be difficult to navigate a surgical instrument into common bile duct 312 via insertion through duodenal papilla 12314. Therefore, it is common during medical procedures to cut sphincter of Oddi 310 to enlarge duodenal papilla 12314 to allow for easier access of instrument into common bile duct 12312.

FIG. 13 is a diagram illustrating an example of mother-daughter endoscopes used in an ERCP procedure, and a portion of patient anatomy where the procedure is performed, near hepatic duct 13312 and pancreatic duct 13316. The mother-daughter endoscopes comprise an auxiliary scope 434 (cholangioscope) attached to and advanced through a lumen 432 of a main scope 400 (duodenoscope). The auxiliary scope 434 can comprise a lumen 436. The distal portion of the main scope 400 positioned in duodenum 308 comprises a functional module 402, an insertion section module 404, and a control module 406. The control module 406 can include, or be coupled to, a controller 408. Similar to the discussion above with respect to FIG. 10, the control module 406 can include other components, such as those described with reference to endoscopy system 10 (FIG. 10) and control unit 16 (FIG. 11). Additionally, the control module 406 can comprise components for controlling an imaging device (e.g., a camera) and a light source connected to the auxiliary scope 434, such as an imaging unit 410, a lighting unit 412 and a power unit 414. The main scope 400 can be configured similarly as endoscope 14 of FIGS. 10 and 11.

The functional module 13402 of the main scope 13400 can comprise an elevator portion 13430. The auxiliary scope 13434 can itself include functional components, such as camera lens 13437 and a light lens (not illustrated) coupled to control module 13406, to facilitate navigation of the auxiliary scope 13434 from the main scope 13400 through the anatomy and to facilitate viewing of components extending from lumen 13432.

In ERCP, the auxiliary scope 13434 can be guided into the sphincter of Oddi 13310. Therefrom, a surgeon operating the auxiliary scope 13434 can navigate the auxiliary scope 13434 through the lumen 13432 of the main scope toward the gallbladder 13305, liver 13304, or other locations in the gastrointestinal system to perform various procedures. In some examples, the auxiliary scope 13434 can be used to guide an additional device to the anatomy to obtain biological matter (e.g., tissue), such as by passage through or attachment to lumen 13436.

The biological sample matter can be removed from the patient, typically by removal of the additional device from the auxiliary device, so that the removed biological matter can be analyzed to diagnose one or more conditions of the patient. According to several examples, the mother-daughter endoscope assembly (including the main scope 13400 and the auxiliary scope 13434) can include additional device features, such as forceps or an auger, for gathering and removing cancerous or pre-cancerous matter (e.g., carcinoma, sarcoma, myeloma, leukemia, lymphoma and the like), or performing endometriosis evaluation, biliary ductal biopsies, and the like.

The controller 13408 can include, or be coupled to, an endoscopic procedure data receiver 13450, and a treatment plan generator 13460. The endoscopic procedure data receiver 13450 can generate images of target anatomy, such as duodenal papilla or a portion of the biliary and pancreatic ductal system. In an example, the endoscopic procedure data receiver 13450 can generate real-time endoscope images of duodenal papilla and its surrounding environment using an imaging sensor on the endoscope, such as a camera located at the functional section 1330 of the endoscope 1314. In some examples, the endoscopic procedure data receiver 13450 can acquire other procedure-related information, including sensor information (e.g., sensors associated with the endoscope), device information, patient medical history etc. In some examples, the endoscopic procedure data receiver 13450 can retrieve, such as from a database, endoscopic procedure data performed by a plurality of physicians on a plurality of patients.

In an example, the endoscopic surgical system, including the endoscope 13400 and the associated components (e.g., the control module 13406, the controller 13408, the treatment plan generator 13460 and the endoscopies procedure data receiver 13450) as shown in FIG. 13 can reside in a large "center" hospital. The endoscope surgical system as shown can be a part of an inter-facility content sharing and endoscopic procedure planning platform that facilitates patient information exchange and cooperative planning of endoscopic procedures between the center hospital and one or more smaller "peripheral" or regional hospitals. The center hospital generally has more advanced medical resources for ERCP procedures (e.g., surgical equipment, devices, or tools, and physician experiences and skills) than a peripheral hospital. The endoscopic procedure data receiver 450 can include a computing and storages device residing in or otherwise accessible by the center hospital. The endoscopic procedure data receiver 13450 can include or be coupled to a communication interface 13470 configured to receive information from a remote computing and storage device 481 residing in or accessible by a peripheral hospital. The received information can include procedure data collected from a patient being treated or scheduled to be treated in the peripheral hospital which has inferior medical resources and/or physician experiences or skills. Alternatively, the remote computing and storage device 13481 can upload patient procedure data to a cloud storage of a cloud 13482. The cloud 13482 can be one or more computing devices (e.g., servers) configured to provide cloud-based services including, for example, data storage, computing services, and provisioning of customer services, among others. The endoscopic procedure data receiver 13450 can remotely and securely access the cloud 13482 and retrieve the patient procedure data. In some examples, the endoscopic procedure data receiver 13450 (e.g., the computing and storages device included therein) can process the procedure data received from the peripheral hospital to generate new data, such as a reconstructed or integrated three-dimensional (3D) image of an anatomical target from images received from the peripheral hospital. Examples of inter-facility content sharing and endoscopic procedure planning are discussed below, such as with reference to FIG. 14.

The treatment plan generator 13460, which is an example of the treatment generator 1144 as illustrated in FIG. 11, can generate a treatment plan, such as an endoscope navigation plan using the information received or generated by the endoscopic procedure data receiver 13450, such as endoscopic images. The endoscope navigation plan can include one or more cannulation or navigation parameters including, for example: a position of the endoscope distal portion (e.g., the functional section 1030 of the endoscope 1014 as shown in FIG. 10) relative to an anatomical target of interest, such as a distance from the endoscope distal portion to duodenal papilla, a heading direction of the endoscope distal portion relative to the anatomical target, an angle of a cannula or a surgical element used in cannulation, a protrusion amount of a cannula or a surgical element, a speed or force applied to the endoscope distal portion or a surgical element, a rotational direction or a cutting area of a surgical element, or a projected navigation path toward the anatomical target, among others. In some examples, the endoscope navigation plan (e.g., one or more navigation parameters) can be generated or updated using a trained machine-learning (ML) model. The endoscope navigation plan, including the reference endoscopic images and parameters, may be provided to the operating physician as a procedure guide during cannulation and navigation.

In an example, the treatment plan generator 13460 can generate a treatment plan, optionally other procedure recommendations (e.g., patient monitoring, facility and schedules for a follow-up procedure), using patient procedure data received from the remote computing and storage device 13481 or from the cloud 13482. With more advanced medical resources available to the center hospital, more effective individualized treatment plan can be generated and executed at the center hospital. Additionally or alternatively, the treatment plan or other procedure recommendations can be provided to the remote computing and storage device 13481 via the communication interface 13470, which can be utilized by the peripheral to facilitate additional procedures or other treatment options.

FIG. 14 is a diagram illustrating an example of an inter-facility content sharing and endoscopic procedure planning system 500 that facilitate patient information exchange and cooperative planning of endoscopic procedures between (i) a large "center" hospital 520 and (ii) one or more smaller "peripheral" or regional hospitals including, by way of example and not limitation, three peripheral hospitals 510A, 510B, and 510C. The center hospital 520 has more advanced medical resources required for performing complex endoscopic procedures (e.g., ERCP) than each of the "peripheral" or regional hospitals 510A-510C. Such advanced medical resources at the center hospital 520 can include, for example, sufficient quantity and/or superior quality of surgical equipment, devices, or tools for use in endoscopic procedures of particular type(s); more qualified and experienced physicians, endoscopists, and other healthcare professionals; extensive trainings, experiences, knowledge, and skillsets of the healthcare professionals, etc.

The inter-facility content sharing and endoscopic procedure planning system 500 can comprise computing and storages devices residing in or otherwise accessible by respective hospitals. For example, each of the peripheral hospitals 510A-510C can access a respective first computing and storage device. The center hospital 520 can access a second computing and storage device. The second computing and storage device can be communicatively connected to each of the first computing and storage devices via a communication network 570. The communication network 570 can utilize any one of a number of transfer protocols (e.g., frame relay, internet protocol (IP), transmission control protocol (TCP), user datagram protocol (UDP), hypertext transfer protocol (HTTP), etc.). Example communication networks may include a local area network (LAN), a wide area network (WAN), a packet data network (e.g., the Internet), mobile telephone networks (e.g., cellular networks), Plain Old Telephone (POTS) networks, and wireless data networks (e.g., Institute of Electrical and Electronics Engineers (IEEE) 802.11 family of standards known as WiFi®, IEEE 802.16 family of standards known as WiMax®), IEEE 802.15.4 family of standards, peer-to-peer (P2P) networks, among others. In an example, the second computing and storage device can be configured to communicate with each of the first computing and storage devices directly via a cloud computing device, such as the cloud 482, which can provide services including cloud storage of patient procedure data. In some examples (as illustrated in FIG. 14), at least some of the peripheral hospitals can be communicatively connected to each other to exchange information therebetween via the communication network.

When an endoscopic procedure is performed on or scheduled for a patient at a peripheral hospital (e.g., hospital 510A), patient record and procedure data can be collected and stored in a computing and storage device (e.g., the remote computing and storage device 481) residing in or otherwise accessible by peripheral hospital 510A. The patient procedure data collected at the peripheral hospital 510A can include preoperative and perioperative images of patient anatomy associated with the endoscopic procedures scheduled or performed at the at least one first facility. For example, for an ERCP, the images can include images of papilla. The images can include endoscopic images and/or images acquired by an external imaging device, such as X-ray or fluoroscopy images, electrical potential map or an electrical impedance map, CT images, MRI images such as images obtained during MRCP, or acoustic images such as EUS images, among others. In some examples, the patient procedure data collected at the peripheral hospital 510A can include endoscopic surgical device information associated with prior endoscopic procedures performed on the patient, specification data, including size, dimension, shape, and structures of the endoscope used in an ERCP procedure or other steerable instruments such as a cannular, a catheter, or a guidewire; size, dimension, shape, and structures of treatment tools or devices for tissue removal (e.g., balloons or baskets for calculi removal). In some examples, the patient procedure data collected at the peripheral hospital 510A can include outcome of prior procedures performed on the patient at the peripheral hospital 510A, such as success/failure assessment, failure rate, procedure time, prognosis, complications, etc.

The patient procedure data can be stored in the computing and storage device accessible by peripheral hospital 510A, or alternatively uploaded to a cloud storage of the cloud 482. At least a portion of the patient procedure data can be selectively transmitted to the center hospital 520. Alternatively, the center hospital 520 can securely get access to certain type of patient procedure data provided by the peripheral hospital 510A. In an example, the patient procedure data received at the center hospital 520 can include data from past failure ERCP procedures, procedures taking substantially long time, or procedures leading to post-operative complications. In an examples, the patient procedure data received at the center hospital 520 can include past procedure data acquired from a patient with surgically altered or otherwise difficult anatomy. In an examples, the patient procedure data received at the center hospital 520 can include data acquired from patients deemed by the peripheral hospital 510A as having a high risk of adverse events, such as post-ERCP risks for pancreatitis, bleeding, etc.

The center hospital 520 can process the received patient procedure data, generate diagnostics, devising treatment plans for the patient, using the more advanced medical resources available to the center hospital 520. In an example, based on the patient data such as anatomy (e.g., papilla anatomy for ERCP), level of complexity of procedure, or resources and experiences available to the peripheral hospital 510A (e.g., procedure failure rate at the peripheral hospital 510A), the computing and storage device at the center hospital 520 can generate a recommendation not to proceed with the procedure at the peripheral hospital 510A, and send the patient to the center hospital 520 or other identified facility with adequate resources and experiences for subsequent treatment or evaluation.

In an example, the computing and storage device at the center hospital 520 can reconstruct patient anatomy images using the preoperative and perioperative images of patient anatomy received from the peripheral hospital 510A. The reconstructed image can include a three-dimensional (3D) image reconstructed from two or more two-dimensional (2D) images of patient anatomy captured prior to or during the procedure at the peripheral hospital 510A. The 2D images can include endoscopic images or endoscopic video frames captured by an imaging device, X-ray or fluoroscopy images of an anatomical target and nearby environment acquired before or during the endoscopic procedure, or electrical potential map or an electrical impedance map of the patient anatomy. In some examples, the reconstructed 3D image can be further integrated with other secondary image sources, such as a CT image, an MRI image such as obtained from a Magnetic resonance cholangiopancreatography (MRCP) procedure, or an endoscopic ultrasonography (EUS) image. A cannulation or endoscope navigation plan can be generated based at least one the reconstructed and/or integrated images. The reconstructed or integrated image, and/or the cannulation or endoscope navigation plan can be transmitted to the peripheral hospital 510A via the communication network 570. Commonly assigned U.S. Patent Application No. 63/263,711 entitled "IMAGE GUIDANCE DURING CANNULATION," describes various examples of multi-modality 3D image reconstruction and integration, and endoscopic procedure guidance using the reconstructed and integrated 3D image, the disclosure of which is hereby incorporated by reference in its entirety.

In an example, the computing and storage device at the center hospital 520 can generate a device recommendation for use in an endoscopic procedure, such as type and size of guide wires, catheters, stents, tissue acquisition tools for use in an ERCP procedure. The recommendation may include recommended values of one or more cannulation or navigation parameters for maneuvering and endoscopic device or other surgical tools. Commonly assigned U.S. Patent Application No. 63/263,732 entitled "AUTOMATIC POSI- TIONING AND FORCE ADJUSTMENT IN ENDOSCOPY," describes various examples of estimating cannulation or navigation parameters for use in an endoscopic procedure, the disclosure of which is hereby incorporated by reference in its entirety.

In an example, the computing and storage device at the center hospital 520 can generate patient diagnostics and post-procedural risk assessment, subsequent treatment recommendations for complications such as pancreatitis, bleeding, etc. In an example, the center hospital 520 can provide additional recommendations on patient monitoring, treatment facility, and schedules for a follow-up procedures. The follow-up procedures may by scheduled to be carried out at the center hospital 520. Alternatively, the follow-up procedures may by scheduled to be carried out at a peripheral hospital. For example, in ERCP for calculi removal, some of small fragment of calculi during the procedure at the center hospital 520 may remain and the information can be provided to peripheral hospital 510A for follow-up procedures. In another example, based on the preoperative and perioperative data for ERCP, a closest medical facility with adequate recourses can be recommended along with schedules for follow-up procedures.

The computing and storage device at the center hospital 520 can send, via the communication network, the generated treatment plan, additional diagnostics, and endoscopic procedure recommendation to peripheral hospital 510A to facilitate patient care or follow-up endoscopic procedures therein. For example, the center hospital 520 may send educational information about specific types of anatomies and procedures (e.g., for ERCP) to one or more peripheral hospitals. In some examples, an audio or video conference session can be established between the respective computing and storage devices at the center hospital 520 and the peripheral hospital 510A, during which a physician of the center hospital 520 can provide consultation to healthcare professionals at the peripheral hospital 510A. Proper consultants can be chosen from respective hospitals based on the information about patient and the procedure.

FIG. 15 is a flow chart illustrating an example method 600 for providing inter-facility content sharing and planning an endoscopic procedure, such as between at least one first computing and storage device accessible by respective at least one first facility (such as one or more of the peripheral hospitals 510A, 510B, and 510C as illustrated in FIG. 14) and a second computing and storage device accessible by a second facility (such as the large "center" hospital 520 as illustrated in FIG. 14). The second facility has more advanced medical resources required for performing complex endoscopic procedures (e.g., ERCP) than each of the at least one first facility. The first facility is also referred to as a peripheral facility or hospital, and the second facility is also referred to as a center facility or hospital. Examples of the more advanced medical resources available to the second facility can include sufficient quantity and/or superior quality of surgical equipment, devices, or tools for use in endoscopic procedures of particular type(s); more qualified and experienced physicians, endoscopists, and other healthcare professionals; extensive trainings, experiences, knowledge, and skillsets of the healthcare professionals, etc. The method 600 may be implemented in and executed by the inter-facility content sharing and endoscopic procedure planning system 500.

Although the processes of the method 600 are drawn in one flow chart, they are not required to be performed in a particular order. In various examples, some of the processes can be performed in a different order than that illustrated herein.

At 610, a communication between the at least one first computing and storage device and the second computing and storage device can be established, such as via the communication network 570 as shown in FIG. 14. In some examples, the second computing and storage device can communicate with each of the first computing and storage device directly via a cloud computing device, such as the cloud 482. When two or more peripheral hospitals are involved, at least some of the peripheral hospitals can be communicatively connected to each other to exchange information therebetween via the communication network.

At 620, at least a portion of procedure data collected by and stored in the at least one first computing and storage device can be transmitted to the second computing and storage device. The procedure data can be associated with endoscopic procedures scheduled or performed at the at least one first facility. In an example, the procedure data can include data collected from endoscopic cholangiopancreatography (ERCP) procedures scheduled or performed at the at least one first facility. The procedure data collected at the at least one first facility can include preoperative and perioperative images of patient anatomy from the endoscopic procedures scheduled or performed therein. Examples of the images can include endoscopic images and/or images acquired by an external imaging device, such as X-ray or fluoroscopy images, electrical potential map or an electrical impedance map, CT images, MRI images such as images obtained during MRCP, or acoustic images such as EUS images, among others. The procedure data can include endoscopic surgical device information associated with prior endoscopic procedures performed at the at least one first facility. The procedure data can include patient record. In some examples, the procedure can include outcome of prior procedures performed on the patient at the at least one first facility, such as success/failure assessment, failure rate, procedure time, prognosis, complications, etc.

In an example, the procedure data transmitted to the second facility can include data from past failure ERCP procedures, procedures taking substantially long time, or procedures leading to post-operative complications. In an examples, the procedure data transmitted to the second facility can include past procedure data acquired from a patient with surgically altered or otherwise difficult anatomy. In an examples, the procedure data transmitted to the second facility can include data acquired from patients deemed by the at least one first facility as having a high risk of adverse events, such as post-ERCP risks for pancreatitis, bleeding, etc.

At 630, an endoscopic procedure recommendation can be generated at the second computing and storage device, and made accessible by the second facility, or the "center" hospital. The endoscopic procedure recommendation can be generated using at least the transmitted portion of the procedure data from the at least one first facility, and the more advanced medical resources available to the second facility. The endoscopic procedure recommendation can include device recommendation for use in an endoscopic procedure, recommended values of one or more cannulation or navigation parameters for maneuvering and endoscopic device or other surgical tools, patient diagnostics and post-procedural risk assessment, subsequent treatment recommendations for complications such as pancreatitis, bleeding, etc., patient monitoring, treatment facility, and schedules for a follow-up procedures, among others.

In some examples, the computing and storage device at the second facility can reconstruct patient anatomy images using the preoperative and perioperative images of patient anatomy received from the at least one first facility. The reconstructed image can include a three-dimensional (3D) image reconstructed from two or more two-dimensional (2D) images of patient anatomy. In some examples, the reconstructed 3D image can be further integrated with other secondary image sources, such as a CT image, an MRI image such as obtained from a Magnetic resonance cholangiopancreatography (MRCP) procedure, or an endoscopic ultrasonography (EUS) image. The reconstructed or integrated image can be used to generate the endoscopic procedure recommendation. Additionally or alternatively, the reconstructed or integrated image can be sent to the at least one first facility.

At 640, the endoscopic procedure recommendation generated at 630 can be transmitted to the at least one first computing and storage device to facilitate an endoscopic procedure at the at least one first facility. Additional patient diagnostics generated by the second facility can also be sent to the at least one first computing and storage device to assist in patient care or a follow-up procedure at the at least one first facility. In some examples, educational information about specific types of anatomies and procedures (e.g., for ERCP), which is generated at the second facility (e.g., the center hospital 520 in FIG. 14), may be sent to at least one first facility (e.g., one or more peripheral hospitals 510A, 510B, or 510C). In some examples, an audio or video conference session can be established between the at least first facility and the second facility to facilitate subsequent procedure planning or other treatment options.

FIG. 16 illustrates generally a block diagram of an example machine 700 upon which any one or more of the techniques (e.g., methodologies) discussed herein may perform. Portions of this description may apply to the computing framework of various portions of the treatment plan generator 460 and the inter-facility content sharing and endoscopic procedure planning system 500.

In alternative embodiments, the machine 700 may operate as a standalone device or may be connected (e.g., networked) to other machines. In a networked deployment, the machine 700 may operate in the capacity of a server machine, a client machine, or both in server-client network environments. In an example, the machine 700 may act as a peer machine in peer-to-peer (P2P) (or other distributed) network environment. The machine 700 may be a personal computer (PC), a tablet PC, a set-top box (SM), a personal digital assistant (PDA), a mobile telephone, a web appliance, a network router, switch or bridge, or any machine capable of executing instructions (sequential or otherwise) that specify actions to be taken by that machine. Further, while only a single machine is illustrated, the term “machine” shall also be taken to include any collection of machines that individually or jointly execute a set (or multiple sets) of instructions to perform any one or more of the methodologies discussed herein, such as cloud computing, software as a service (SaaS), other computer cluster configurations.

Examples, as described herein, may include, or may operate by, logic or a number of components, or mechanisms. Circuit sets are a collection of circuits implemented in tangible entities that include hardware (e.g., simple circuits, gates, logic, etc.). Circuit set membership may be flexible over time and underlying hardware variability. Circuit sets include members that may, alone or in combination, perform specified operations when operating. In an example, hardware of the circuit set may be immutably designed to carry out a specific operation (e.g., hardwired). In an example, the hardware of the circuit set may include variably connected physical components (e.g., execution units, transistors, simple circuits, etc.) including a computer readable medium physically modified (e.g., magnetically, electrically, moveable placement of invariant massed particles, etc.) to encode instructions of the specific operation. In connecting the physical components, the underlying electrical properties of a hardware constituent are changed, for example, from an insulator to a conductor or vice versa. The instructions enable embedded hardware (e.g., the execution units or a loading mechanism) to create members of the circuit set in hardware via the variable connections to carry out portions of the specific operation when in operation. Accordingly, the computer readable medium is communicatively connected to the other components of the circuit set member when the device is operating. In an example, any of the physical components may be used in more than one member of more than one circuit set. For example, under operation, execution units may be used in a first circuit of a first circuit set at one point in time and reused by a second circuit in the first circuit set, or by a third circuit in a second circuit set at a different time.

Machine (e.g., computer system) 700 may include a hardware processor 702 (e.g., a central processing unit (CPU), a graphics processing unit (GPU), a hardware processor core, or any combination thereof), a main memory 704 and a static memory 706, some or all of which may communicate with each other via an interlink (e.g., bus) 708. The machine 700 may further include a display unit 710 (e.g., a raster display, vector display, holographic display, etc.), an alphanumeric input device 712 (e.g., a keyboard), and a user interface (UI) navigation device 714 (e.g., a mouse). In an example, the display unit 710, input device 712 and UI navigation device 714 may be a touch screen display. The machine 700 may additionally include a storage device (e.g., drive unit) 716, a signal generation device 718 (e.g., a speaker), a network interface device 720, and one or more sensors 721, such as a global positioning system (GPS) sensor, compass, accelerometer, or other sensors. The machine 700 may include an output controller 728, such as a serial (e.g., universal serial bus (USB), parallel, or other wired or wireless (e.g., infrared (IR), near field communication (NFC), etc.) connection to communicate or control one or more peripheral devices (e.g., a printer, card reader, etc.).

The storage device 716 may include a machine readable medium 722 on which is stored one or more sets of data structures or instructions 724 (e.g., software) embodying or utilized by any one or more of the techniques or functions described herein. The instructions 724 may also reside, completely or at least partially, within the main memory 704, within static memory 706, or within the hardware processor 702 during execution thereof by the machine 700. In an example, one or any combination of the hardware processor 702, the main memory 704, the static memory 706, or the storage device 716 may constitute machine readable media.

While the machine-readable medium 722 is illustrated as a single medium, the term “machine readable medium” may include a single medium or multiple media (e.g., a centralized or distributed database, and/or associated caches and servers) configured to store the one or more instructions 724.

The term “machine readable medium” may include any medium that is capable of storing, encoding, or carrying instructions for execution by the machine 700 and that cause the machine 700 to perform any one or more of the techniques of the present disclosure, or that is capable of storing, encoding or carrying data structures used by or associated with such instructions. Non-limiting machine-readable medium examples may include solid-state memories, and optical and magnetic media. In an example, a massed machine-readable medium comprises a machine readable medium with a plurality of particles having invariant (e.g., rest) mass. Accordingly, massed machine-readable media are not transitory propagating signals. Specific examples of massed machine-readable media may include: non-volatile memory, such as semiconductor memory devices (e.g., Electrically Programmable Read-Only Memory (EPROM), Electrically Erasable Programmable Read-Only Memory (EPSOM)) and flash memory devices; magnetic disks, such as internal hard disks and removable disks; magneto-optical disks; and CD-ROM and DVD-ROM disks.

The instructions 724 may further be transmitted or received over a communication network 726 using a transmission medium via the network interface device 720 utilizing any one of a number of transfer protocols (e.g., frame relay, internet protocol (IP), transmission control protocol (TCP), user datagram protocol (UDP), hypertext transfer protocol (HTTP), etc.). Example communication networks may include a local area network (LAN), a wide area network (WAN), a packet data network (e.g., the Internet), mobile telephone networks (e.g., cellular networks), Plain Old Telephone (POTS) networks, and wireless data networks (e.g., Institute of Electrical and Electronics Engineers (IEEE) 802.11 family of standards known as WiFi®, IEEE 802.16 family of standards known as WiMax®), IEEE 802.15.4 family of standards, peer-to-peer (P2P) networks, among others. In an example, the network interface device 720 may include one or more physical jacks (e.g., Ethernet, coaxial, or phone jacks) or one or more antennas to connect to the communication network 726. In an example, the network interface device 720 may include a plurality of antennas to wirelessly communicate using at least one of single-input multiple-output (SIMO), multiple-input multiple-output (MIMO), or multiple-input single-output (MISO) techniques. The term "transmission medium" shall be taken to include any intangible medium that is capable of storing, encoding or carrying instructions for execution by the machine 700, and includes digital or analog communications signals or other intangible medium to facilitate communication of such software.

ADDITIONAL NOTES

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

30. A system for providing inter-facility content sharing and endoscopic procedure planning, the system comprising:
 - a plurality of networked devices, including (i) at least one first computing and storage device accessible by respective at least one first facility and (ii) a second computing and storage device accessible by a second facility having more advanced medical resources than the at least one first facility;
 - wherein the at least one first computing and storage device is configured to collect and store therein procedure data associated with endoscopic procedures scheduled or performed at the at least one first facility, and to transmit at least a portion of the procedure data to the second computing and storage device via a communication network;
 - wherein the second computing and storage device is configured to:
   - generate an endoscopic procedure recommendation using (i) the at least a portion of the procedure data received from the at least one first facility and (ii) the more advanced medical resources of the second facility; and
   - send, via the communication network, the generated endoscopic procedure recommendation to the at least one first computing and storage device to facilitate an endoscopic procedure therein.

31. The system of example 30, wherein the procedure data collected at the at least one first facility include data collected from an endoscopic cholangiopancreatography (ERCP) procedure, and the generated endoscopic procedure recommendation includes a recommended ERCP procedure plan for the at least one first facility.

32. The system of example 30, wherein the at least a portion of the procedure data include preoperative or perioperative images of patient anatomy collected from the endoscopic procedures scheduled or performed at the at least one first facility.

33. The system of example 32, wherein the second computing and storage device is configured to reconstruct a three-dimensional (3D) patient anatomy image using the preoperative or perioperative images of patient anatomy received from the at least one first facility, and to generate the endoscopic procedure recommendation further using the reconstructed 3D patient anatomy image.

34. The system of example 30, wherein the at least a portion of the procedure data include endoscopic surgical device information associated with the endoscopic procedures performed at the at least one first facility.

35. The system of example 30, wherein the at least a portion of the procedure data include data collected from one or more failed endoscopic procedures performed at the at least one first facility.

36. The system of example 30, wherein the at least a portion of the procedure data include pre- or perioperative data collected from one or more patients identified based on their respective anatomies and medical record.

37. The system of example 30, wherein the endoscopic procedure recommendation includes a device recommendation to be used in an endoscopic procedure.

38. The system of example 30, wherein the endoscopic procedure recommendation includes respective values of one or more cannulation or navigation parameters for maneuvering an endoscopic device.

39. The system of example 30, wherein the endoscopic procedure recommendation includes a follow-up procedure plan.

40. The system of example 39, wherein the follow-up procedure plan includes a recommended facility and schedule for a follow-up procedure.

41. The system of example 39, wherein the follow-up procedure plan includes a follow-up endoscopic procedure at the second facility, wherein the second computing and storage device is further configured to collect follow-up procedure data, and to communicate the follow-up procedure data to the at least one first computing and storage device.

42. The system of example 30, wherein the second computing and storage device is further configured to generate educational information about anatomies and endoscopic procedures, and to send the educational information to the at least one first computing and storage device via the communication network.

43. The system of example 42, wherein the second computing and storage device is further configured to:

generate patient diagnostics or post-operative risk assessment; and send, via the communication network, the generated patient diagnostics or post-operative risk assessment to the at least one first computing and storage device to facilitate the endoscopic procedure therein.

44. The system of example 30, wherein the plurality of networked devices includes two or more first computing and storage devices each communicatively connected to the second computing and storage devices and configured to transmit respective portions of procedure data to the second computing and storage device, wherein the second computing and storage device is configured to:

generate the endoscopic procedure recommendation further using the procedure data received respectively from the two or more first computing and storage devices; and send the generated endoscopic procedure recommendation to at least one of the two or more first computing and storage devices to facilitate the endoscopic procedure therein.

45. A method for providing inter-facility content sharing and planning an endoscopic procedure between (i) at least one first computing and storage device accessible by respective at least one first facility and (ii) a second computing and storage device accessible by a second facility having more advanced medical resources than the at least one first facility, the method comprising:

establishing a communication between the at least one first computing and storage device and the second computing and storage device;

transmitting at least a portion of procedure data collected by and stored in the at least one first computing and storage device to the second computing and storage device, the procedure data associated with endoscopic procedures scheduled or performed at the at least one first facility;

generating, via the second computing and storage device, an endoscopic procedure recommendation using (i) the at least a portion of the procedure data received from the at least first facility and (ii) the more advanced medical resources of the second facility; and sending the generated endoscopic procedure recommendation to the at least one first computing and storage device to facilitate an endoscopic procedure therein.

46. The method of example 45, wherein the at least a portion of the procedure data include preoperative or perioperative images of patient anatomy collected from the endoscopic procedures scheduled or performed at the at least one first facility.

47. The method of example 46, further comprising reconstructing, via the second computing and storage device, a three-dimensional (3D) patient anatomy image using the preoperative or perioperative images of patient anatomy received from the at least one first facility, wherein generating the endoscopic procedure recommendation includes further using the reconstructed 3D patient anatomy image.

48. The method of example 45, wherein the at least a portion of the procedure data include endoscopic surgical device information associated with the endoscopic procedures performed at the at least one first facility.

49. The method of example 45, wherein the at least a portion of the procedure data include data collected from one or more failed endoscopic procedures performed at the at least one first facility.

50. The method of example 45, wherein the at least a portion of the procedure data include pre- or perioperative data collected from one or more patients identified based on their respective anatomies and medical record.

51. The method of example 45, wherein the endoscopic procedure recommendation includes one or more of;
    a device recommendation to be used in an endoscopic procedure;
    respective values of one or more cannulation or navigation parameters for maneuvering an endoscopic device; or
    a follow-up procedure plan.
52. The method of example 45, further comprising, via the second computing and storage device;
    generating educational information about anatomies and endoscopic procedures; and
    sending the educational information to the at least one first computing and storage device.
53. The method of example 45, further comprising, via the second computing and storage device:
    generating patient diagnostics or post-operative risk assessment; and
    sending the generated patient diagnostics or post-operative risk assessment to the at least one first computing and storage device to facilitate the endoscopic procedure therein.

CROSS REFERENCE TO RELATED APPLICATIONS

This application is related to commonly assigned U.S. Provisional Patent Application Ser. No. 63/263,711, entitled "IMAGE GUIDANCE DURING CANNULATION", filed on Nov. 8, 2021, U.S. Provisional Patent Application Ser. No. 63/263,715, entitled "PROCEDURE GUIDANCE FOR SAFETY", filed on Nov. 8, 2021, U.S. Provisional Patent Application Ser. No. 63/263,720, entitled "ENDOLUMINAL TRANSHEPATIC ACCESS PROCEDURE", filed on Nov. 8, 2021, U.S. Provisional Patent Application Ser. No. 63/263,732, entitled "AUTOMATIC POSITIONING AND FORCE ADJUSTMENT IN ENDOSCOPY", filed on Nov. 8, 2021, U.S. Provisional Patent Application Ser. No. 63/363,446, entitled "AUTOMATIC POSITIONING AND FORCE ADJUSTMENT IN ENDOSCOPY", filed on Apr. 22, 2022, U.S. Provisional Patent Application Ser. No. 63/364,453, entitled "AI-BASED ENDOSCOPIC TARGET IDENTIFICATION AND PROCEDURE PLANNING", filed on May 10, 2022, U.S. Provisional patent application Ser. No. 63/364,566, entitled "AI-BASED ENDOSCOPIC TISSUE ACQUISITION PLANNING", filed on May 12, 2022, which are incorporated by reference in their entirety.

FIELD OF THE DISCLOSURE

The present document relates generally to endoscopic systems, and more particularly to risk management of adverse events associated with stricture management devices used in endoscopic procedures.

BACKGROUND

Endoscopes have been used in a variety of clinical procedures, including, for example, illuminating, imaging, detecting and diagnosing one or more disease states, providing fluid delivery (e.g., saline or other preparations via a fluid channel) toward an anatomical region, providing passage (e.g., via a working channel) of one or more therapeutic devices or biological matter collection devices for sampling or treating an anatomical region, and providing suction passageways for collecting fluids (e.g., saline or other preparations), among other procedures. Examples of such anatomical region can include gastrointestinal tract (e.g., esophagus, stomach, duodenum, pancreaticobiliary duct, intestines, colon, and the like), renal area (e.g., kidney(s), ureter, bladder, urethra) and other internal organs (e.g., reproductive systems, sinus cavities, submucosal regions, respiratory tract), and the like.

Some endoscopes include a working channel through which an operator can perform suction, placement of diagnostic or therapeutic devices (e.g., a brush, a biopsy needle or forceps, a stent, a basket, or a balloon), or minimally invasive surgeries such as tissue sampling or removal of unwanted tissue (e.g., benign or malignant strictures) or foreign objects (e.g., calculi). Some endoscopes can be used with a laser or plasma system to deliver energy to an anatomical target (e.g., soft or hard tissue or calculi) to achieve desired treatment. For example, laser has been used in applications of tissue ablation, coagulation, vaporization, fragmentation, and lithotripsy to break down calculi in kidney, gallbladder, ureter, among other stone-forming regions, or to ablate large calculi into smaller fragments.

In conventional endoscopy, the distal portion of the endoscope can be configured for supporting and orienting a therapeutic device, such as with the use of an elevator. In some systems, two endoscopes can work together with a first endoscope guiding a second endoscope inserted therein with the aid of the elevator. Such systems can be helpful in guiding endoscopes to anatomic locations within the body that are difficult to reach. For example, some anatomic locations can only be accessed with an endoscope after insertion through a circuitous path.

Peroral cholangioscopy is a technique that permits direct endoscopic visualization, diagnosis, and treatment of various disorders of patient biliary and pancreatic ductal system using miniature endoscopes and catheters inserted through the accessory port of a duodenoscope. Peroral cholangioscopy can be performed by using a dedicated cholangioscope that is advanced through the accessory channel of a duodenoscope, as used in Endoscopic Retrograde Cholangio-Pancreatography (ERCP) procedures. ERCP is a technique that combines the use of endoscopy and fluoroscopy to diagnose and treat certain problems of the biliary or pancreatic ductal systems, including the liver, gallbladder, bile ducts, pancreas, or pancreatic duct. In ERCP, a cholangioscope (also referred to as an auxiliary scope, or a "daughter" scope) can be attached to and advanced through a working channel of a duodenoscope (also referred to as a main scope, or a "mother" scope). Typically, two separate endoscopists operate each of the "mother-daughter" scopes. Although biliary cannulation can be achieved directly with the tip of the cholangioscope, most endoscopists prefer cannulation over a guidewire. A tissue retrieval device can be inserted through the cholangioscope to retrieve biological matter (e.g., gallstones, bill duct stones, cancerous tissue) or to manage stricture or blockage in bile duct.

Peroral cholangioscopy can also be performed by inserting a small-diameter dedicated endoscope directly into the bile duct, such as in a Direct PerOral Cholangioscopy (DPOC) procedure. In DPOC, a slim endoscope (cholangioscope) can be inserted into patient mouth, pass through the upper GI tract, and enter into the common bile duct for visualization, diagnosis, and treatment of disorders of the biliary and pancreatic ductal systems.

Endoscopic procedures for stricture management involves placing a stricture management device to open or dilate an obstructed or narrowed portion of the ductal system. For examples, endoscopic placement of pancreaticobiliary stents plays an important role in the treatment of biliary stricture secondary to benight or malignant etiologies, such as damage to the bile duct (e.g., as a surgical complication), passage of gallstones to the bile duct, infections of the bile duct, pancreatitis, or cancer in the bile duct or pancreas. During ERCP, a duodenoscope can be passed through the mouth and esophagus and down to the duodenum, and a self-expandable stent can be passed through a working channel of the endoscope and inserted into the obstructed bile duct to prop open the stricture.

SUMMARY

Proximal and distal stent migration is one of the most common complications after endoscopic placement of pancreaticobiliary stents. Dilated common bile duct (CBD), wide sphincterotomy, and biliary balloon dilation can cause stent migration. The migrated stents can migrate intraluminal in the CBD, duodenum or the colon. Sequelae of stent migration can include symptoms of cholangitis, painless jaundice, bowel perforation, among others. Early assessment of risk of adverse events associated with pancreaticobiliary stent migration can help prevent or reduce complications, or facilitate early preventive actions (e.g., stent reposition or removal).

The present disclosure describes systems and methods for managing risks of adverse events or complications associated with deployment or use of stricture management devices (SMDs), such as pancreaticobiliary stent migration or dislodgment. Risk of complications or adverse events can be estimated based on analysis of an image of an SMD. Artificial intelligence (AI) or machine learning (ML) techniques may be used in the image analysis. According to one embodiment disclosed herein, an endoscopic system comprises an endoscope configured to deploy an SMD at an anatomical target in a patient, and a processor to receive an image of the SMD. The image can be an endoscopic image or an image produced by an external imaging device. The processor can derive from the received image information correlated to a risk of complication associated with deployment or use of the SMD at the anatomical target. In an example, the processor can apply the SMD image, or image features derived therefrom, to a trained machine-learning (ML) model to derive information correlated to a risk of complication, such as an estimate of SMD migration risk. The migration risk can be based on a degree of deformation of the SMD. The migration risk assessment may be triggered by an endoscopic procedure interacting with the SMD, such as repositioning or replacement of the SMD, endoscopic tissue acquisition, or calculi removal. The processor can output the derived information correlated to the risk of complication to a user interface or a control circuit to provide a control signal to an actuator to perform robotic surgery. In some examples, the processor can identify and register an SMD deployment site based at least on images of patient anatomy, determine tissue characteristics such as malignancy at the deployment site, and generate a navigation path for navigating the endoscope and placing the SMD at the identified deployment site.

The AI-based risk management of adverse events such as pancreaticobiliary stent migration and computer-assisted navigation and device placement as described in this disclosure can improve risk assessment of adverse events associated with SMD, prevent or reduce complications, and facilitate early preventive actions against further adverse events. Automated identification and registration of desired device deployment site and navigation planning can improve the endoscope navigation accuracy and efficiency (e.g., such as navigating into duodenal papilla or through tight strictures). Enhanced automation in endoscopic procedure can help ease physicians' burden of manual surgical planning, reduce variability of procedure outcome due to variations in experience and dexterity across operating physicians (e.g., surgeons or endoscopists), and improve the endoscopic procedure prognostic predictability. As a result, overall procedure efficiency, accuracy, patient safety, and endoscopic procedure success rate can be improved.

Example 1 is an endoscopic system, comprising: an endoscope configured to deploy a stricture management device (SMD) at an anatomical target in a patient; and a processor configured to: receive an image of the SMD deployed at the anatomical target; derive, from the received image, information correlated to a risk of complication associated with deployment or use of the SMD at the anatomical target; and output the derived information correlated to the risk of complication.

In Example 2, the subject matter of Example 1 optionally includes the derived information correlated to the risk of complication that can include an estimate of a migration risk of the SMD migrating away from the anatomical target.

In Example 3, the subject matter of Example 2 optionally includes the SMD that can include a stent deployed at a portion of patient pancreaticobiliary system, wherein the processor is configured to estimate the migration risk of the stent in response to a procedure interacting with the SMD.

In Example 4, the subject matter of any one or more of Examples 2-3 optionally includes the processor that can be configured to categorize the estimate of the migration risk into one of a plurality of risk levels.

In Example 5, the subject matter of any one or more of Examples 1-4 optionally includes the derived information correlated to the risk of complication that can include a recommended action to avoid or mitigate complication caused by deployment of the SMD at the anatomical target.

In Example 6, the subject matter of any one or more of Examples 1-5 optionally includes the derived information correlated to the risk of complication that can include a recommended schedule of a follow-up visit for the patient.

In Example 7, the subject matter of any one or more of Examples 1-6 optionally includes the received image of the SMD that can include one or more of an endoscopic image, an X-ray or fluoroscopy image, a computer tomography (CT) image, a magnetic resonance imaging (MRI) image, or an acoustic image.

In Example 8, the subject matter of any one or more of Examples 1-7 optionally includes the processor that can be configured to: extract a morphological feature from the received image of the SMD; and derive the information correlated to the risk of complication further using the extracted morphological feature.

In Example 9, the subject matter of Example 8 optionally includes the morphological feature that can include a curvature of a curved portion of the received image of the SMD.

In Example 10, the subject matter of any one or more of Examples 8-9 optionally includes the morphological feature that can include a count of curved sections of the image of the SMD.

In Example 11, the subject matter of any one or more of Examples 1-10 optionally includes the processor that can be configured to derive the information correlated to the risk of complication further using sensor data acquired by a sensor included in the SMD, the sensor data indicative of a shape or a change in shape of the SMD.

In Example 12, the subject matter of any one or more of Examples 1-11 optionally includes the processor that can be configured to derive the information correlated to the risk of complication further using a characteristic of the anatomical target at which the SMD is deployed.

In Example 13, the subject matter of Example 12 optionally includes the characteristic of the anatomical target that can include a tissue inflammation state of the anatomical target.

In Example 14, the subject matter of any one or more of Examples 12-13 optionally includes the SMD that can include a stent deployed at a portion of patient pancreaticobiliary system, and the characteristic of the anatomical target includes size and shape of a tissue target or a calculi target to be extracted and passed through the stent.

In Example 15, the subject matter of any one or more of Examples 1-14 optionally includes the processor that can be configured to derive the information correlated to the risk of complication further using information about a pre-deployment shape or geometry of the SMD.

In Example 16, the subject matter of any one or more of Examples 1-15 optionally includes the processor that can be configured to derive the information correlated to the risk of complication further using patient demographic information.

In Example 17, the subject matter of any one or more of Examples 1-16 optionally includes the processor that can be configured to apply the received image of the SMD to a trained machine-learning (ML) model to estimate the information correlated to the risk of complication.

In Example 18, the subject matter of Example 17 optionally includes the processor that can include a training module configured to train an ML model using a training dataset comprising (i) images of SMDs deployed at respective anatomical targets from past procedures on a plurality of patients and (ii) assessments of migration risks of the SMDs at respective anatomical targets.

In Example 19, the subject matter of Example 18 optionally include the training module that can be configured to train the ML model using supervised learning or unsupervised learning.

In Example 20, the subject matter of any one or more of Examples 17-19 optionally includes the processor that can be configured to apply the received image of the SMD to the trained ML model to generate a recommended action for correcting SMD migration.

In Example 21, the subject matter of any one or more of Examples 1-20 optionally includes a user interface configured to receive a user input designating a deployment site at the anatomical target for deploying the SMD via a steerable elongate instrument, wherein the processor is further configured to register the designated deployment site, and generate a deployment plan for navigating the steerable elongate instrument and deploying the SMD at the designated deployment site.

In Example 22, the subject matter of any one or more of Examples 1-21 optionally includes the anatomical target that can include an anatomical stricture in a vicinity of the deployed SMD, wherein the processor is further configured to receive an image of the anatomical stricture, and to estimate malignancy of the anatomical stricture using the received endoscopic image of the anatomical stricture.

In Example 23, the subject matter of any one or more of Examples 1-22 optionally includes a user interface configured to present the derived information correlated to the risk of complication to the user.

In Example 24, the subject matter of any one or more of Examples 1-23 optionally includes a controller configured to provide a control signal to an actuator to robotically facilitate a procedure with respect to the SMD based at least on the derived information correlated to the risk of complication.

Example 25 is a method of managing migration of a stricture management device (SMD) deployed at an anatomical target in a patient, the method comprising: receiving patient information including an image of the deployed SMD; deriving, from the received image, information correlated to a risk of complication associated with deployment or use of the SMD at the anatomical target; and outputting the derived information correlated to the risk of complication.

In Example 26, the subject matter of Example 25 optionally includes deriving the information correlated to a risk of complication that can include estimating a migration risk of the SMD migrating away from the anatomical target.

In Example 27, the subject matter of any one or more of Examples 25-26 optionally includes the image of the SMD that can include one or more of an endoscopic image, an X-ray or fluoroscopy image, a computer tomography (CT) image, a magnetic resonance imaging (MRI) image, or an acoustic image.

In Example 28, the subject matter of any one or more of Examples 25-27 optionally includes extracting a morphological feature from the image of the SMD, the morphological feature including one or more of a curvature of a curved portion or a count of curved sections on the image of the deployed SMD, wherein deriving the information correlated to the risk of complication further includes using the extracted morphological feature.

In Example 29, the subject matter of any one or more of Examples 25-28 optionally includes deriving the information correlated to the risk of complication further includes using one or more of: a tissue inflammation state of the anatomical target at which the SMD is deployed; a pre-deployment shape or geometry of the SMD; or patient demographic information.

In Example 30, the subject matter of any one or more of Examples 25-29 optionally includes the SMD that can include a stent deployed at a portion of patient pancreaticobiliary system, wherein deriving the information correlated to the risk of complication further includes using size and shape of a tissue target or a calculi target to be extracted and passed through the stent.

In Example 31, the subject matter of any one or more of Examples 25-30 optionally includes applying the image of the SMD to a trained machine-learning (ML) model to estimate the information correlated to the risk of complication.

In Example 32, the subject matter of Example 31 optionally include, via a training module, training an ML model using a training dataset comprising (i) images of SMDs deployed at respective anatomical targets from past procedures on a plurality of patients and (ii) assessments of migration risks of the SMDs at respective anatomical targets.

In Example 33, the subject matter of any one or more of Examples 25-32 optionally includes: receiving a user input designating a deployment site at the anatomical target for deploying the SMD via a steerable elongate instrument; and registering the designated deployment site and generating a deployment plan for navigating the steerable elongate instrument and deploying the SMD at the designated deployment site.

In Example 34, the subject matter of any one or more of Examples 25-33 optionally includes outputting the derived information correlated to the risk of complication includes presenting the derived information to a user interface, or providing a control signal to an actuator to robotically facilitate a procedure with respect to the SMD based at least on the derived information.

Example 35 is a non-transitory machine-readable storage medium that includes instructions that, when executed by one or more processors of a machine, cause the machine to perform operations comprising: receiving an image of a stricture management device (SMD) deployed at an anatomical target of a patient; deriving, from the received image, information correlated to a risk of complication associated with deployment or use of the SMD at the anatomical target; and outputting the derived information correlated to the risk of complication.

In Example 36, the subject matter of Example 35 optionally includes the operation of deriving the information correlated to the risk of complication that can include estimating a migration risk of the SMD migrating away from the anatomical target.

In Example 37, the subject matter of any one or more of Examples 35-36 optionally includes the instructions cause the machine to perform operations that can include extracting a morphological feature from the image of the SMD, the morphological feature including one or more of a curvature of a curved portion or a count of curved sections on the image of the deployed SMD, wherein deriving the information correlated to the risk of complication further includes using the extracted morphological feature.

In Example 38, the subject matter of any one or more of Examples 35-37 optionally includes the instructions cause the machine to perform operations that can include applying the image of the SMD to a trained machine-learning (ML) model to estimate the information correlated to the risk of complication.

In Example 39, the subject matter of any one or more of Examples 35-38 optionally includes the instructions cause the machine to perform operations that can include: receiving a user input designating a deployment site at the anatomical target for deploying the SMD via a steerable elongate instrument; and registering the designated deployment site and generating a deployment plan for navigating the steerable elongate instrument and deploying the SMD at the designated deployment site.

The presented techniques are described in terms of health-related procedures, but are not so limited. This summary is an overview of some of the teachings of the present application and not intended to be an exclusive or exhaustive treatment of the present subject matter. Further details about the present subject matter are found in the detailed description and appended claims. Other aspects of the disclosure will be apparent to persons skilled in the art upon reading and understanding the following detailed description and viewing the drawings that form a part thereof, each of which are not to be taken in a limiting sense. The scope of the present disclosure is defined by the appended claims and their legal equivalents.

BRIEF DESCRIPTION OF THE DRAWING

Figure 17:
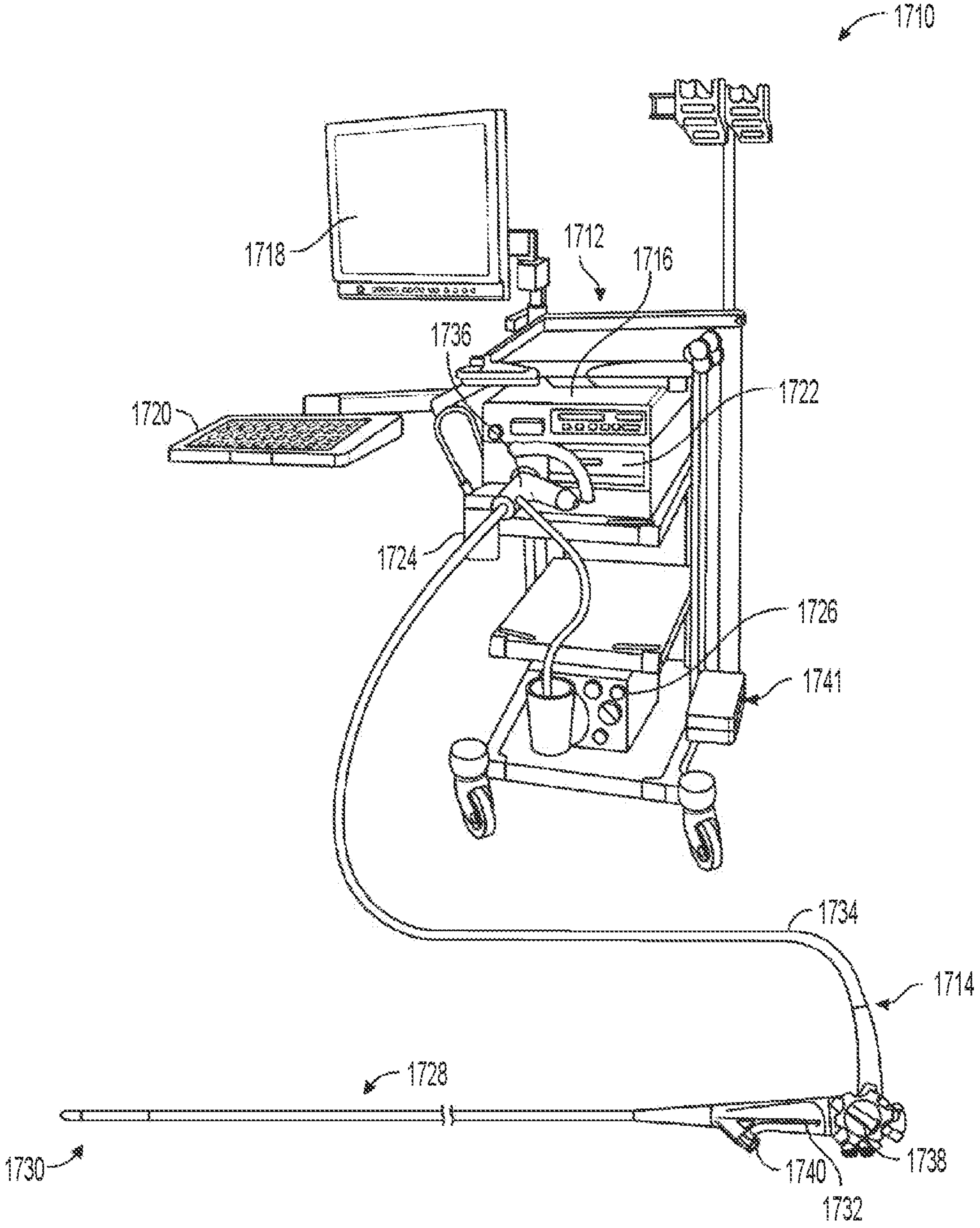
Figure 18:
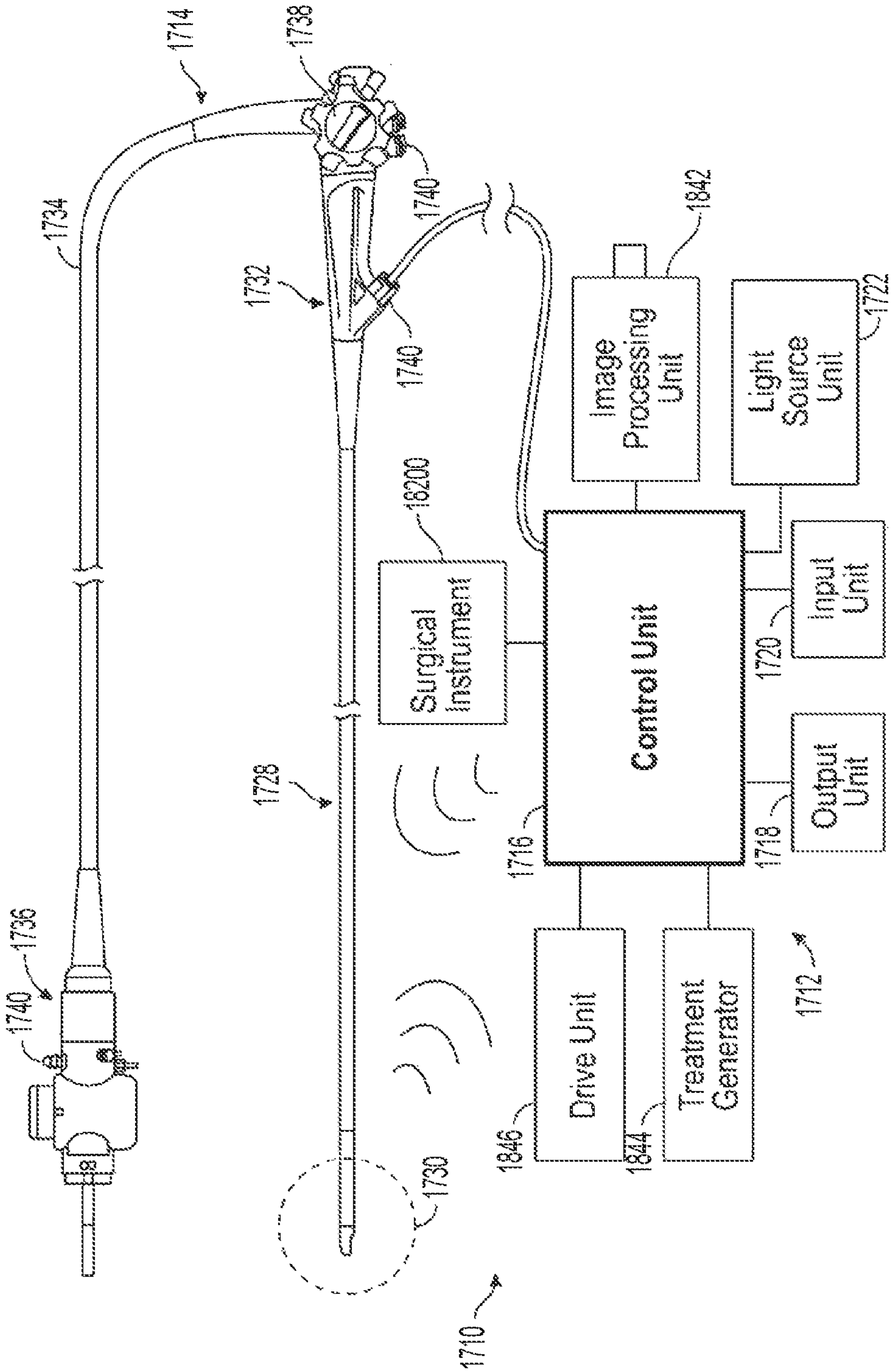

FIGS. 17-18 are schematic diagrams illustrating an example of an endoscopy system for use in endoscopic procedures such as an ERCP procedure.

Figure 19A:
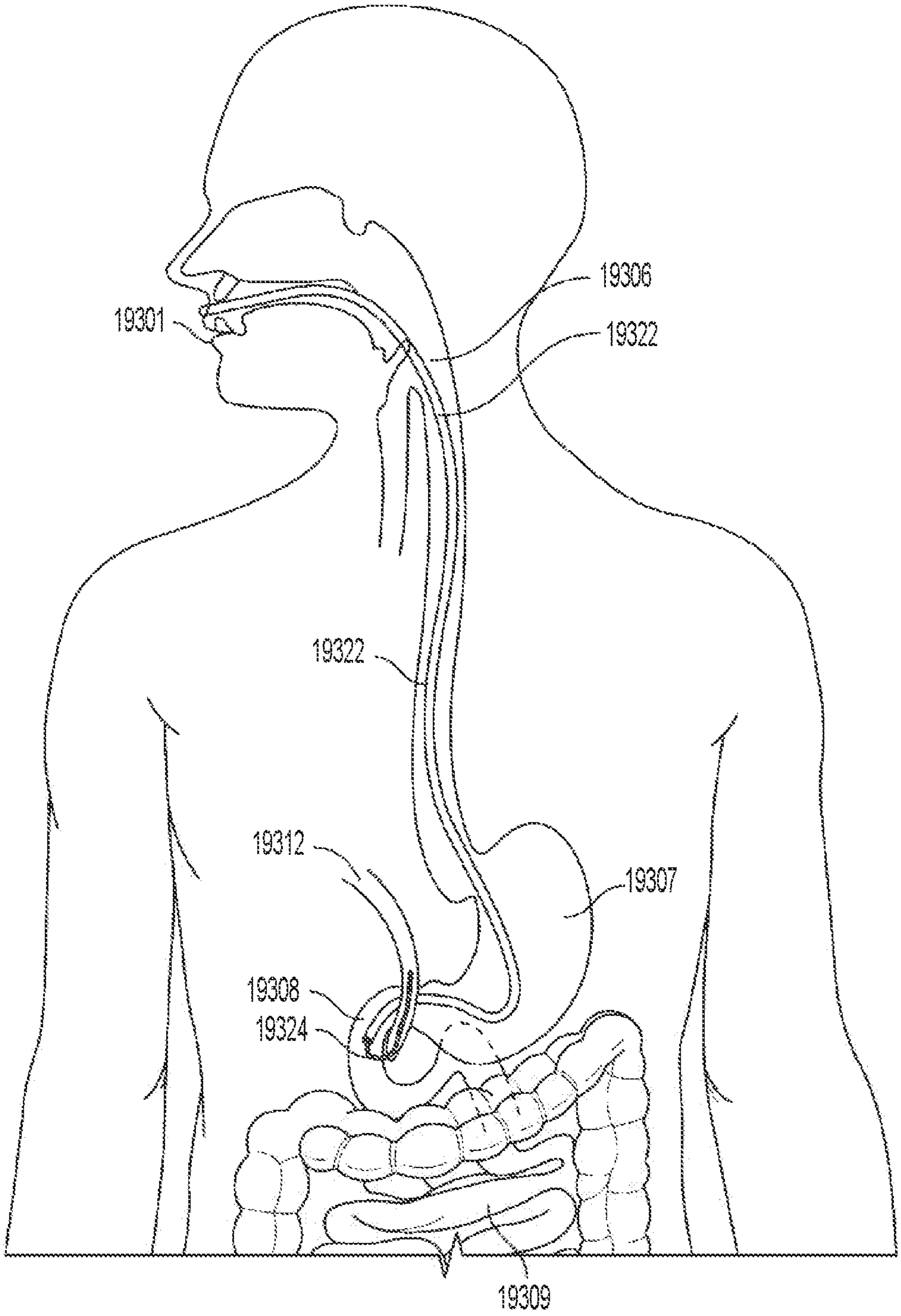
Figure 19B:
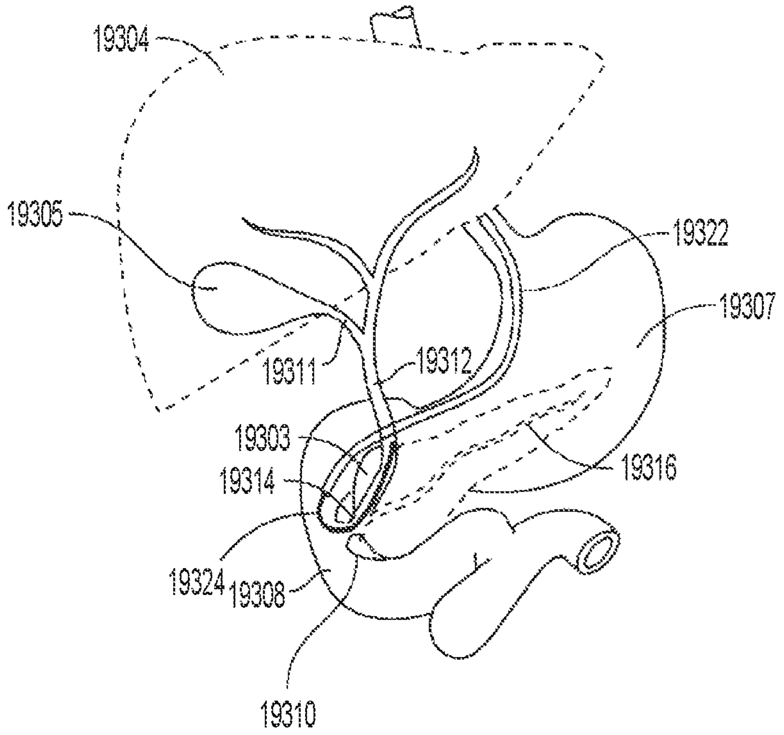

FIGS. 19A-19B are diagrams illustrating an example of peroral cholangioscopy involving direct insertion of a cholangioscope into patient bile duct as in a DPOC procedure, and a portion of patient anatomy where the procedure is performed.

Figure 20A:
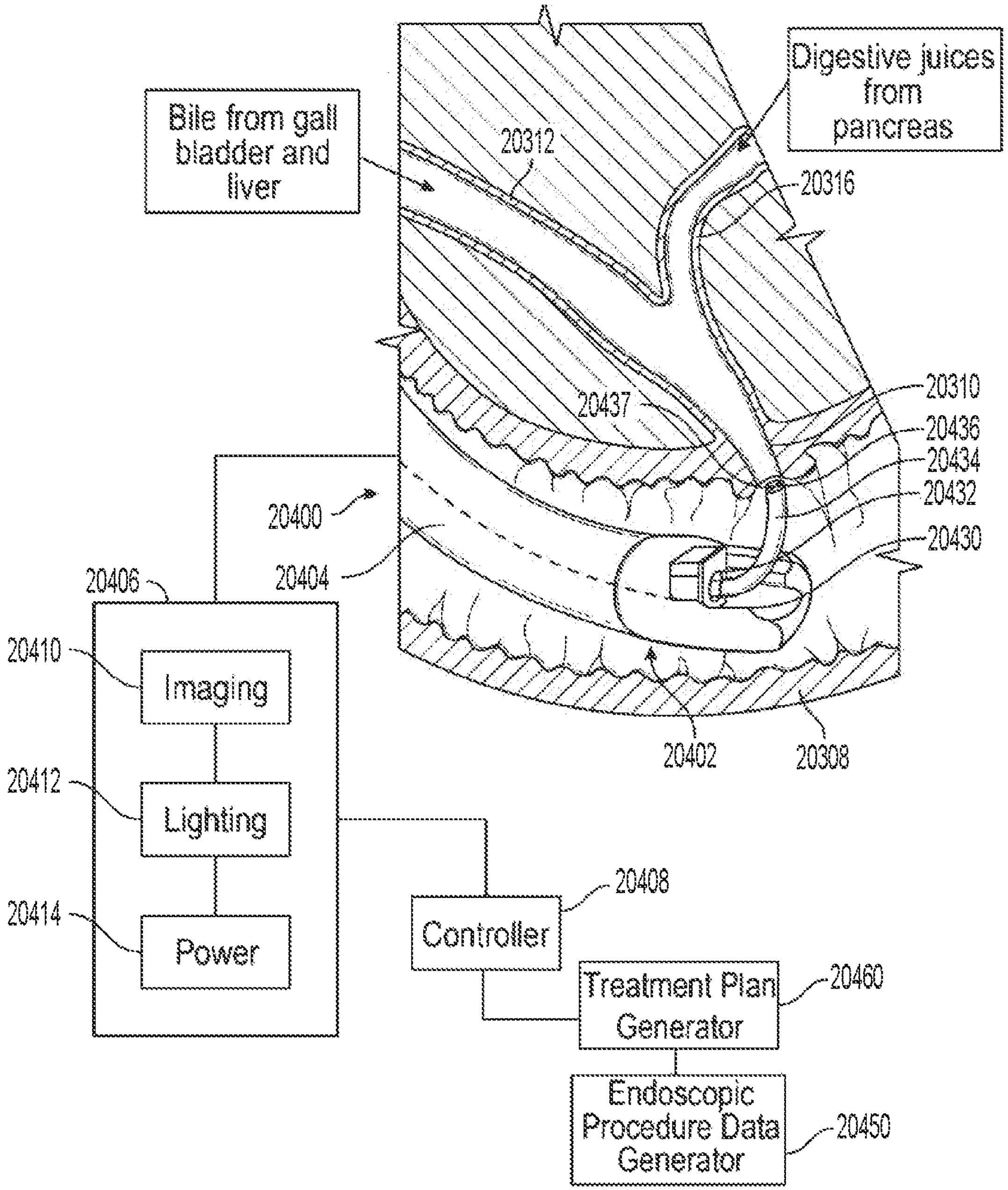
Figure 20B:
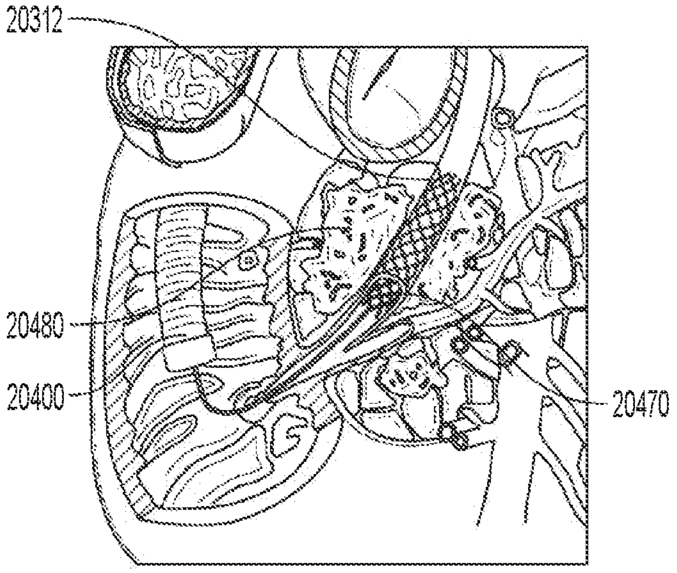
Figure 20C:
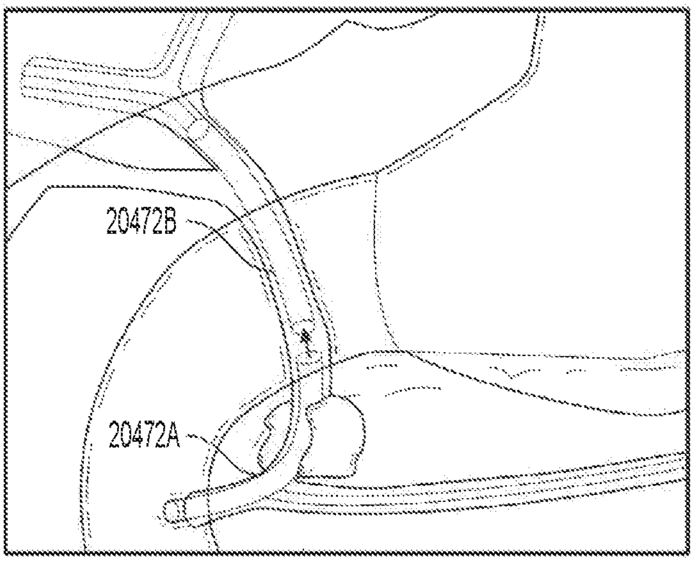

FIGS. 20A-20C are diagrams illustrating examples of mother-daughter endoscopes used in ERCP, biliary ductal stent placement via ERCP, and stent migration.

Figure 21:
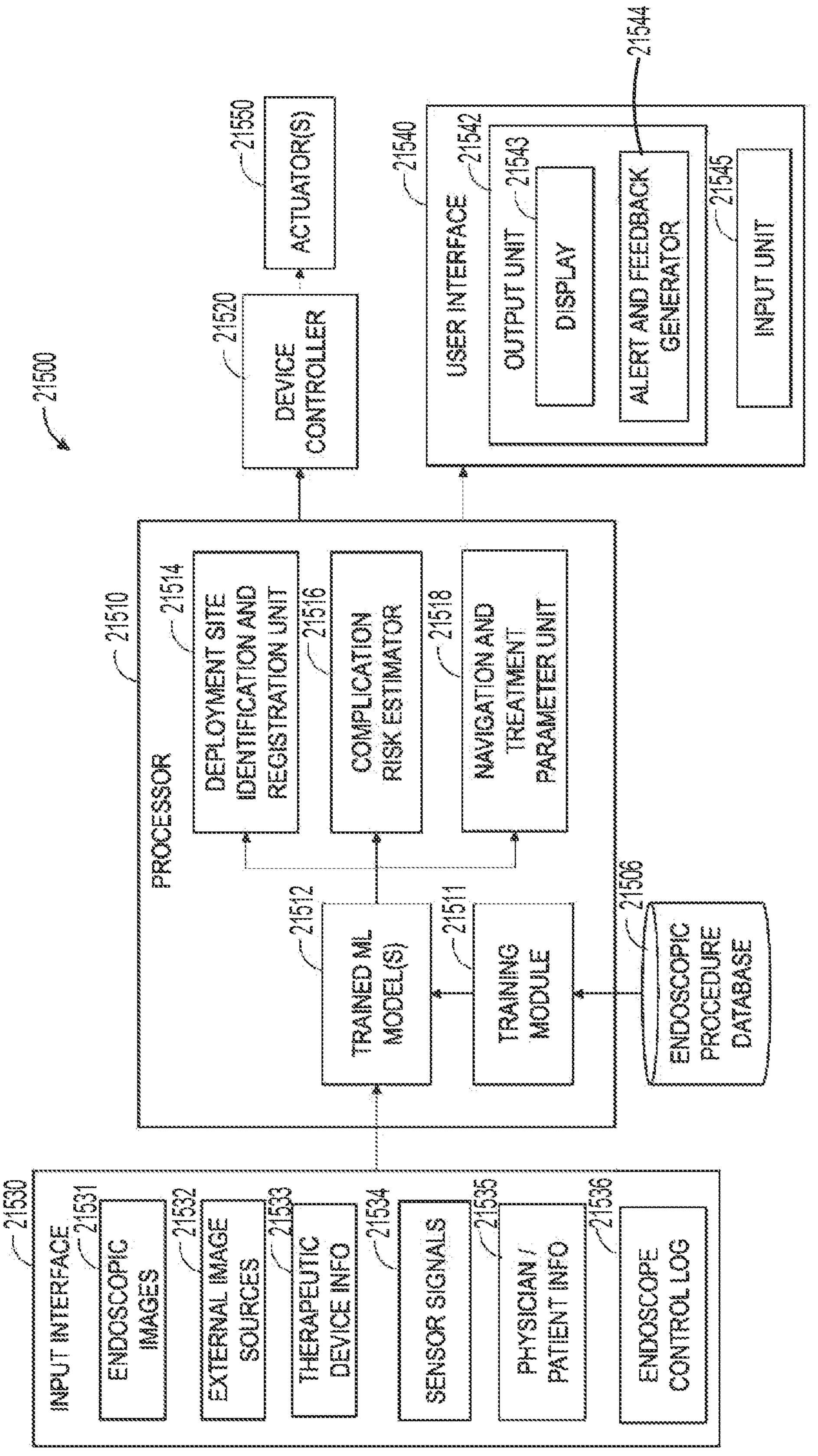

FIG. 21 is a block diagram illustrating an example of an SMD deployment and risk management system to automatically determine an SMD deployment plan and to estimate a complication risk associated with the SMD.

Figure 22A:
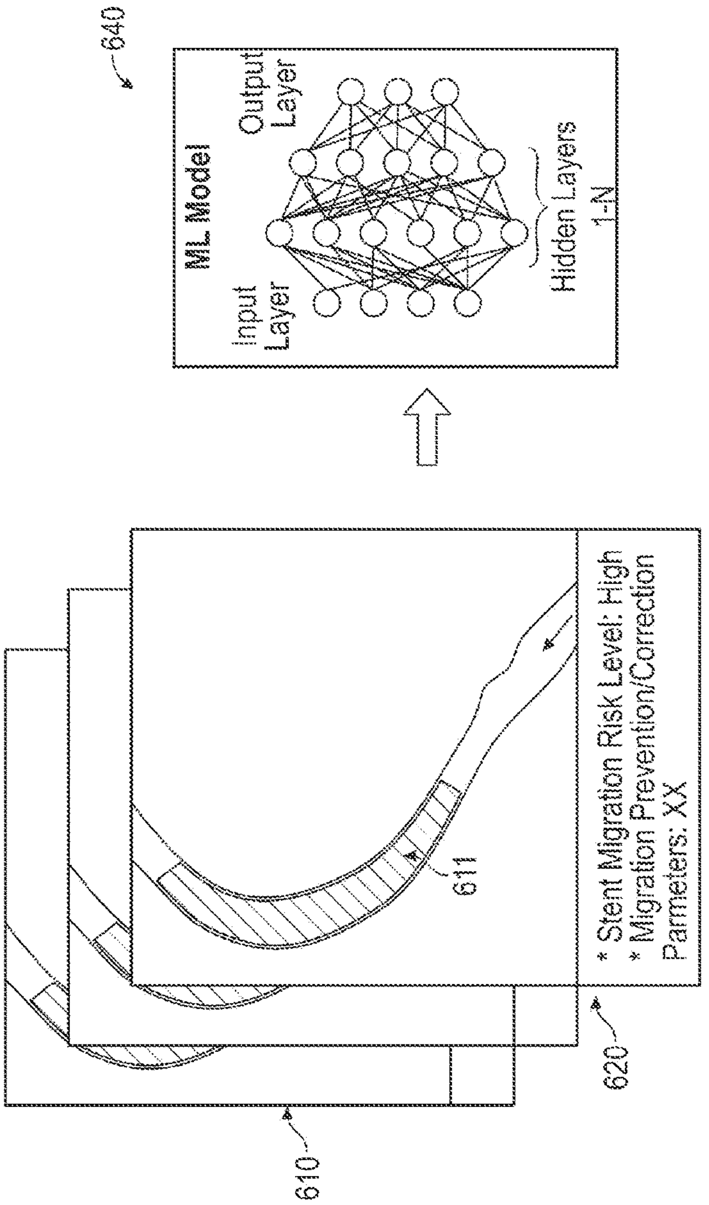
Figure 22B:
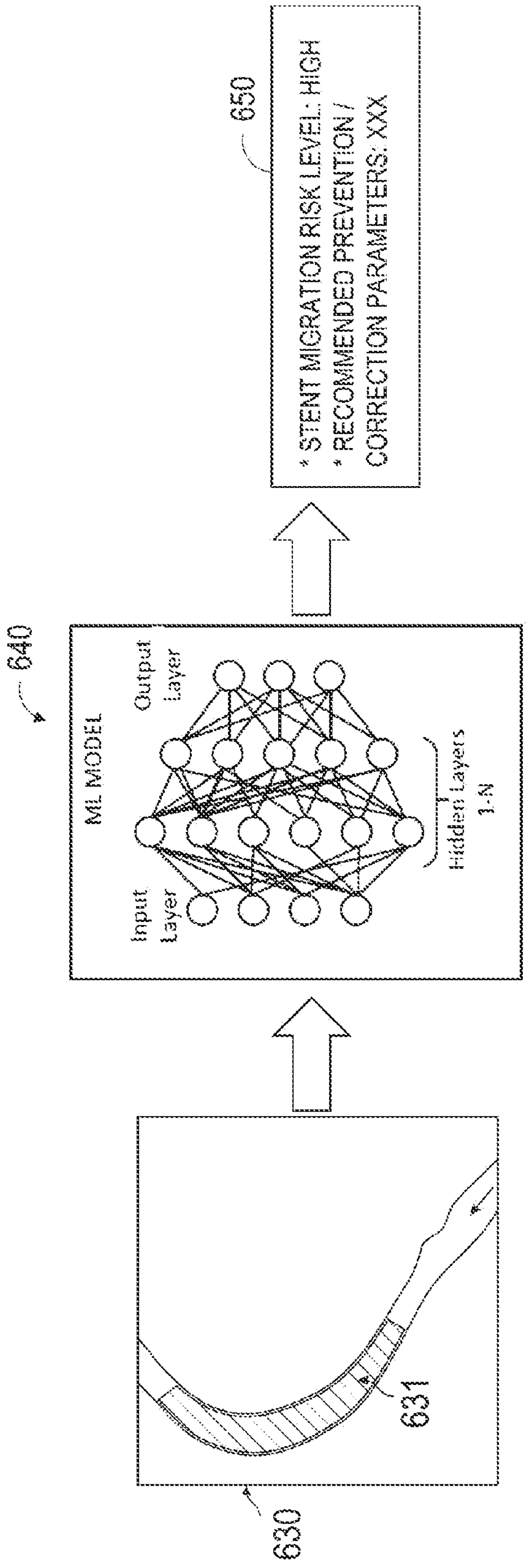

FIGS. 22A-22B are diagrams illustrating an example of training an ML model and using the trained ML model to determine a stent migration risk and a treatment recommendation.

Figure 23:
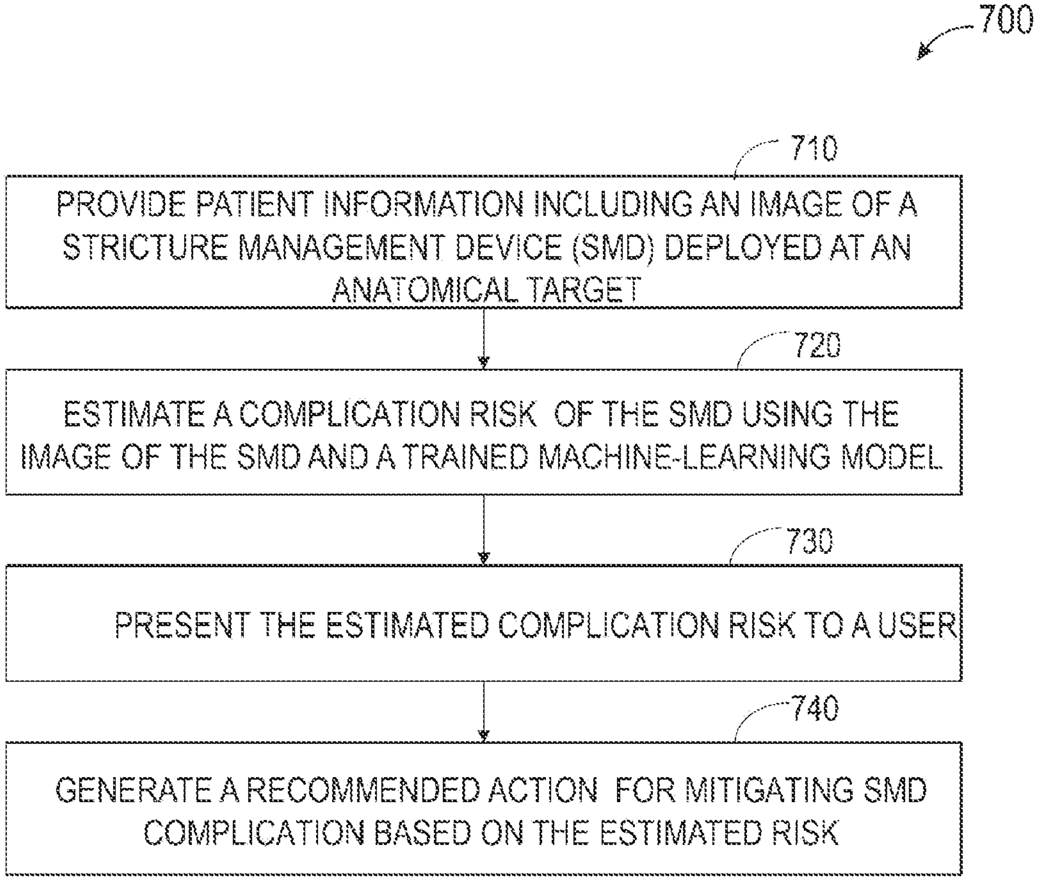

FIG. 23 is a flow chart illustrating an example method for managing a migration risk of an SMD deployed at an anatomical target.

Figure 24:
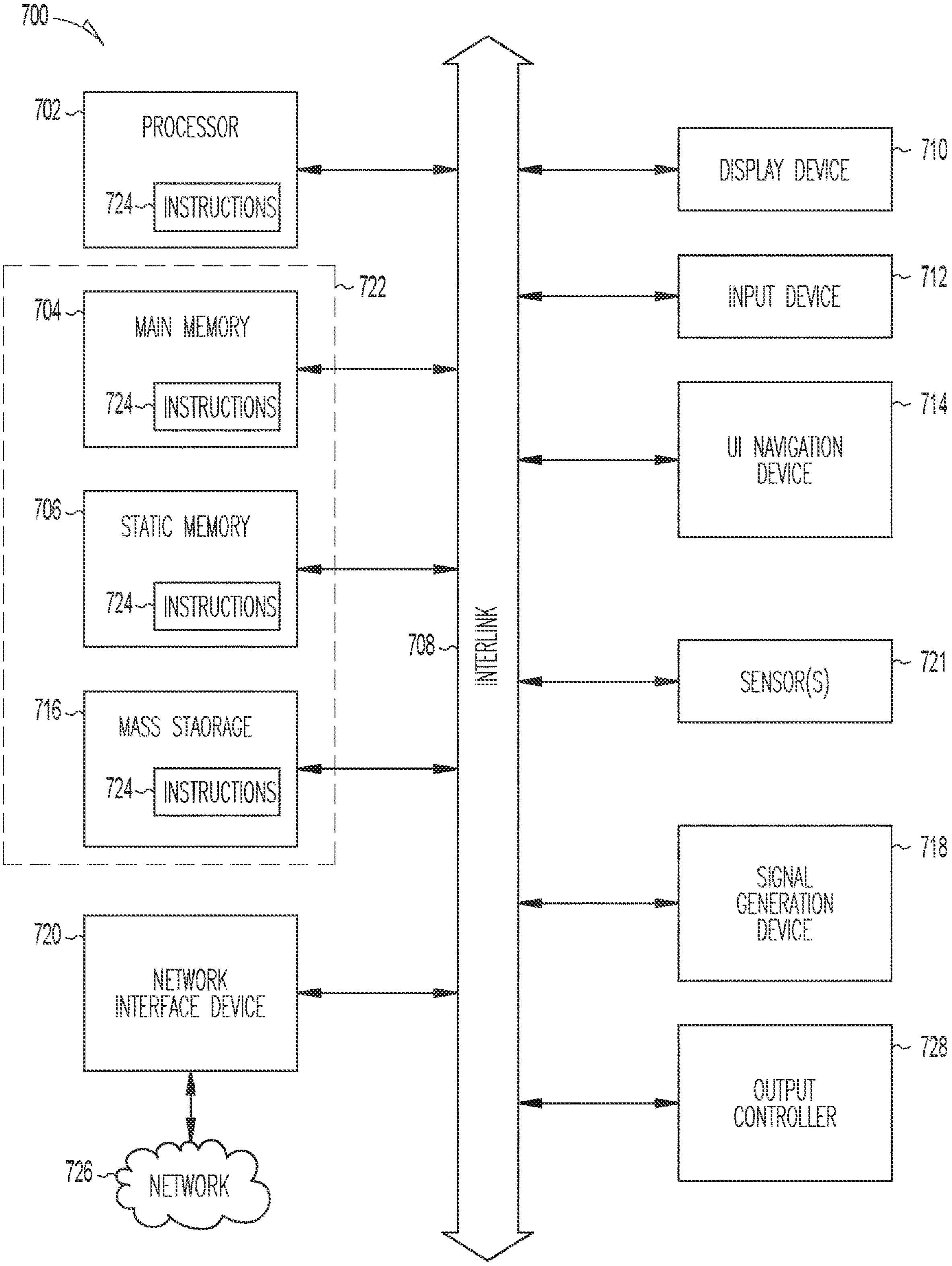

FIG. 24 is a block diagram illustrating an example machine upon which any one or more of the techniques (e.g., methodologies) discussed herein may perform.

DETAILED DESCRIPTION

This document describes systems, devices, and methods for managing risks of adverse events or complications associated with deployment or use of stricture management devices, such as pancreaticobiliary stent migration. According to one embodiment, an endoscopic system comprises an endoscope to deploy a stricture management device (SMD) at an anatomical target in a patient, and a processor to receive an image of the SMD and derive from the received image information correlated to a risk of complication associated with deployment or use of the SMD at the anatomical target. The derived information can include an estimate of a migration risk of the SMD. The processor can use a trained machine-learning model to estimate the migration risk. The processor can output the derived information correlated to the risk of complication to a user interface or a control circuit to provide a control signal to an actuator to perform robotic surgery. In some examples, the processor can identify and register an SMD deployment site based at least on images of patient anatomy, determine tissue characteristics such as malignancy at the deployment site, and generate a navigation path for navigating the endoscope and placing the SMD at the identified deployment site.

FIG. 17 is a schematic diagram illustrating an example of an endoscopy system 1710 for use in endoscopic procedures, such as an ERCP procedure. The system 1710 comprises an imaging and control system 1712 and an endoscope 1714. The endoscopy system 1710 is an illustrative example of an endoscopy system suitable for patient diagnosis and/or treatment using the systems, devices and methods described herein, such as tethered and optically enhanced biological matter and tissue collection, retrieval and storage devices and biopsy instruments that can be used for obtaining samples of tissue or other biological matter to be removed from a patient for analysis or treatment of the patient. According to some examples, the endoscope 1714 can be insertable into an anatomical region for imaging and/or to provide passage of or attachment to (e.g., via tethering) one or more sampling devices for biopsies, or one or more therapeutic devices for treatment of a disease state associated with the anatomical region.

The imaging and control system 1712 can comprise a control unit 1716, an output unit 1718, an input unit 1720, a light source 1722, a fluid source 1724, and a suction pump 1726. The imaging and control system 1712 can include various ports for coupling with endoscopy system 1710. For example, the control unit 1716 can include a data input/output port for receiving data from and communicating data to the endoscope 1714. The light source 1722 can include an output port for transmitting light to the endoscope 1714, such as via a fiber optic link. The fluid source 1724 can comprise one or more sources of air, saline or other fluids, as well as associated fluid pathways (e.g., air channels, irrigation channels, suction channels) and connectors (barb fittings, fluid seals, valves and the like). The fluid source 1724 can be in communication with the control unit 1716, and can transmit one or more sources of air or fluids to the endoscope 1714 via a port. The fluid source 1724 can comprise a pump and a tank of fluid or can be connected to an external tank, vessel or storage unit. The suction pump 1726 can comprise a port used to draw a vacuum from the endoscope 1714 to generate suction, such as for withdrawing fluid from the anatomical region into which the endoscope 1714 is inserted.

The output unit 18 and the input unit 1720 can be used by a human operator and/or a robotic operator of endoscopy system 10 to control functions of endoscopy system 10 and view output of endoscope 1714. In some examples, the control unit 1716 can additionally be used to generate signals or other outputs for treating the anatomical region into which the endoscope 1714 is inserted. Examples of such signals or outputs can include electrical output, acoustic output, a radio-frequency energy output, a fluid output and the like for treating the anatomical region with, for example, cauterizing, cutting, freezing and the like.

The endoscope 1714 can interface with and connect to the imaging and control system 1712 via a coupler section 1736. In the illustrated example, the endoscope 1714 comprises a duodenoscope that may be use in a ERCP procedure, though other types of endoscopes can be used with the features and teachings of the present disclosure. The endoscope 1714 can comprise an insertion section 1728, a functional section 1730, and a handle section 1732, which can be coupled to a cable section 1734 and the coupler section 1736.

The insertion section 1728 can extend distally from the handle section 1732, and the cable section 1734 can extend proximally from the handle section 1732. The insertion section 1728 can be elongate and include a bending section, and a distal end to which functional section 1730 can be attached. The bending section can be controllable (e.g., by control knob 38 on the handle section 1732) to maneuver the distal end through tortuous anatomical passageways (e.g., stomach, duodenum, kidney, ureter, etc.). Insertion section 1728 can also include one or more working channels (e.g., an internal lumen) that can be elongate and support insertion of one or more therapeutic tools of functional section 1730, such as a cholangioscope as shown in FIGS. 20A-20C. The working channel can extend between handle section 1732 and functional section 1730. Additional functionalities, such as fluid passages, guidewires, and pull wires can also be provided by insertion section 1728 (e.g., via suction or irrigation passageways, and the like).

The handle section 1732 can comprise a control knob 1738 and ports 1740. The ports 1740 can be configured to couple various electrical cables, guidewires, auxiliary scopes, tissue collection devices of the present disclosure, fluid tubes and the like to handle section 1732 for coupling with insertion section 1728. The control knob 38 can be coupled to a pull wire, or other actuation mechanisms, extending through insertion section 1728. The control knob 1738 can be used by a user to manually advance or retreat the insertion section 1728 of the endoscope 1714, and to adjust bending of a bending section at the distal end of the insertion section 28. In some examples, an optional drive unit 1846 (FIG. 18) can be used to provide motorized drive for advancing a distal section of endoscope 1714 under the control of the control unit 1716.

The imaging and control system 1712, according to examples, can be provided on a mobile platform (e.g., cart 1741) with shelves for housing light source 1722, suction pump 1726, image processing unit 1842 (FIG. 18), etc. Alternatively, several components of the imaging and control system 1712 shown in FIGS. 17 and 18 can be provided directly on the endoscope 1714 such that the endoscope is "self-contained."

The functional section 1730 can comprise components for treating and diagnosing anatomy of a patient. The functional section 30 can comprise an imaging device, an illumination device, and an elevator. The functional section 1730 can further comprise optically enhanced biological matter and tissue collection and retrieval devices. For example, the functional section 1730 can comprise one or more electrodes conductively connected to handle section 32 and functionally connected to the imaging and control system 1712 to analyze biological matter in contact with the electrodes based on comparative biological data stored in the imaging and control system 1712. In other examples, the functional section 1730 can directly incorporate tissue collectors.

In some examples, the endoscope 1714 can be robotically controlled, such as by a robot arm attached thereto. The robot arm can automatically, or semi-automatically (e.g., with certain user manual control or commands), via an actuator, position and navigate an instrument such as the endoscope 1714 (e.g., the functional section 1730 and/or the insertion section 1728) of in the target anatomy, or position a device at a desired location with desired posture to facilitate an operation of an anatomical target, such as a stricture management device (e.g., a stent) to open or dilate an obstructed or narrowed portion of the ductal system. In accordance with various examples discussed in this document, a controller can use artificial intelligence (AI) to determine cannulation and navigation parameters and/or tool operational parameters (e.g., position, angle, posture, force, and navigation path), and generate a control signal to the actuator of the robot arm to facilitate operation of such instrument or tools in accordance with the determined navigation and operational parameters in a robot-assisted procedure.

FIG. 18 is a schematic diagram of the endoscopy system 1710 shown in FIG. 17, which comprises the imaging and control system 1712 and the endoscope 1714. FIG. 18 schematically illustrates components of the imaging and control system 1712 coupled to the endoscope 1714, which in the illustrated example comprises a duodenoscope. The imaging and control system 1712 can comprise a control unit 1716, which can include or be coupled to an image processing unit 1842, a treatment generator 1844, and a drive unit 1846, as well as the light source 1722, the input unit 1720, and the output unit 1718 as discussed above with reference to FIG. 17. The control unit 1716 can comprise, or can be in communication with, a surgical instrument 18200 comprising a device configured to engage tissue and collect and store a portion of that tissue and through which an imaging device (e.g., a camera) can view target tissue via inclusion of optically enhanced materials and components. The control unit 1716 can be configured to activate an imaging device (e.g., a camera) at the functional section of the endoscope 1714 to view target tissue distal of surgical instrument 18200 and endoscopy system 1710, which can be fabricated of a translucent material to minimize the impacts of the camera being obstructed or partially obstructed by the tissue retrieval device. Likewise, the control unit 1716 can be configured to activate the light source 1722 to shine light on the surgical instrument 18200, which can include select components that are configured to reflect light in a particular manner, such as tissue cutters being enhanced with reflective particles.

The image processing unit 1842 and the light source 1722 can each interface with the endoscope 1714 (e.g., at the functional section 1730) by wired or wireless electrical connections. The imaging and control system 1712 can accordingly illuminate an anatomical region using the light source 1722, collect signals representing the anatomical region, process signals representing the anatomical region using the image processing unit 1842, and display images representing the anatomical region on the output unit 1718. The imaging and control system 1712 can include the light source 1722 to illuminate the anatomical region using light of desired spectrum (e.g., broadband white light, narrow-band imaging using preferred electromagnetic wavelengths, and the like). The imaging and control system 1712 can connect (e.g., via an endoscope connector) to the endoscope 1714 for signal transmission (e.g., light output from light source, video signals from the imaging device such as positioned at the distal portion of the endoscope 1714, diagnostic and sensor signals from a diagnostic device, and the like).

The treatment generator 1844 can generate a treatment plan for delivering and deploying a stricture management device (SMD), such as a pancreaticobiliary stent, at a deployment site. Such a plan, also referred to as an SMD deployment plan, can include identification of a proper SMD deployment site, characteristics such as tissue malignancy at the SMD deployment site, and a navigation path for navigating the endoscope and placing the SMD at the desired deployment site. In some examples, the treatment generator 1844 can estimate a risk of migration, shift, dislodgment, or deformation of the SMD (hereinafter collectively referred to as SMD migration risk). The SMD deployment plan and the estimated SMD migration risk can be generated using patient information including an image of the potential SMD deployment site, or an image of a previously deployed SMD and the anatomical environment at the deployment site. Examples of the images can include endoscopic images, or images from external imaging devices such as X-ray or fluoroscopy images, electrical potential map or an electrical impedance map, computer tomography (CT) images, magnetic resonance imaging (MRI) images obtained in Magnetic resonance cholangiopancreatography (MRCP), or acoustic images such as endoscopic ultrasonography (EUS) images, among others. In some examples, the treatment generator 1844 can generate the SMD deployment plan and/or estimate the SMD migration risk using artificial intelligence (AI) or machine learning (ML). The SMD deployment plan and the SMD migration risk can be presented to an operating physician (e.g., an endoscopist) as a procedure guidance for operating the endoscope 1714, deploying an SMD, or taking appropriate preventive or corrective actions (e.g., repositioning, extracting, or modifying an existing SMD). Additionally or alternatively, the SMD deployment plan or the SMD migration risk can be used to facilitate a robot-assisted endoscopic procedure. Examples of AI-based SMD deployment planning and migration risk assessment are discussed below with reference to FIGS. 21 and 22A-22B.

FIGS. 19A-19B are diagrams illustrating an example of peroral cholangioscopy performed via direct insertion of a cholangioscope 19324 into the bile duct, as in a DPOC procedure, and a portion of patient anatomy where the procedure is performed. The cholangioscope 19324 is nested inside of a guide sheath 19322, and inserted perorally into a patient to reach duodenum 19308. Duodenum 19308 comprises an upper part of the small intestine. The guide sheath 19322 can extend into mouth 19301, through esophagus 19306, through stomach 19307 to reach the duodenum 19308. Before reaching intestines 19309, the guide sheath 19322 can position the cholangioscope 19324 proximate common bile duct 19312. The common bile duct 19312 carries bile from the gallbladder 19305 and liver 19304, and empties the bile into the duodenum 19308 through sphincter of Oddi 19310 (FIG. 19B). The cholangioscope 19324 can extend from guide sheath 19322 to extend into common bile duct 19312. In some examples, steering features of guide sheath 19322 (e.g., pull wire) can be used to facilitate navigating and bending of cholangioscope 19324 through stomach 19307, in addition to direct steering of cholangioscope 19324 via the pull wires. For example, navigation of the Pyloric canal and Pyloric sphincter can be difficult to navigate using only an endoscope. Thus, the guide sheath 19322 can be used to turn or bend elongate body of cholangioscope 19324, or reduce the amount of steering or bending of the elongate body of the cholangioscope 19324 required by pull wires, to facilitate traversing the Pyloric sphincter.

FIG. 19B is a schematic view of duodenum 19308 connected to common bile duct 19312 via duodenal papilla 19314. Common bile duct 19312 can branch off into pancreatic duct 19316 and gallbladder duct 19311. Duodenal papilla 19314 can include sphincter of Oddi 19310 that controls flow of bile and pancreatic juice into the intestine (duodenum). Pancreatic duct 19316 can lead to pancreas 19303. Pancreatic duct 19316 carries pancreatic juice from pancreas 19303 to the common bile duct 19312. Gallbladder duct 19311 can lead to gallbladder 19305. In some patients, it can be difficult to navigate surgical instruments to duodenal papilla 19314. It can also be difficult to navigate a surgical instrument into common bile duct 312 via insertion through duodenal papilla 19314. Therefore, it is common during medical procedures to cut sphincter of Oddi 310 to enlarge duodenal papilla 19314 to allow for easier access of instrument into common bile duct 19312.

FIGS. 20A-20C are diagrams illustrating an example of mother-daughter endoscopes used in ERCP and a portion of patient anatomy of the procedure site, including, among other things, a pancreatic duct 20316, biliary ductal stent placement via ERCP, and stent migration. As illustrated in FIG. 20A, the mother-daughter endoscopes comprise an auxiliary scope 434 (cholangioscope) attached to and advanced through a lumen 432 of a main scope 400 (duodenoscope). The auxiliary scope 434 can comprise a lumen 436. The distal portion of the main scope 400 positioned in patient duodenum 308 comprises a functional module 402, an insertion section module 404, and a control module 406. The control module 406 can include, or be coupled to, a controller 408. Similar to the discussion above with respect to FIG. 17, the control module 406 can include other components, such as those described with reference to endoscopy system 10 (FIG. 17) and control unit 16 (FIG. 18). Additionally, the control module 406 can comprise components for controlling an imaging device (e.g., a camera) and a light source connected to the auxiliary scope 434, such as an imaging unit 410, a lighting unit 412 and a power unit 414. The main scope 400 can be configured similarly as endoscope 14 of FIGS. 17 and 18.

The functional module 20402 of the main scope 20400 can comprise an elevator portion 20430. The auxiliary scope 20434 can itself include functional components, such as camera lens 20437 and a light lens (not illustrated) coupled to control module 20406, to facilitate navigation of the auxiliary scope 20434 from the main scope 20400 through the anatomy and to facilitate viewing of components extending from lumen 20432.

In ERCP, the auxiliary scope 20434 can be guided into the sphincter of Oddi 20310. Therefrom, a surgeon operating the auxiliary scope 20434 can navigate the auxiliary scope 20434 through the lumen 20432 of the main scope toward the gallbladder 20305, liver 20304, or other locations in the gastrointestinal system to perform various procedures. In some examples, the auxiliary scope 20434 can be used to guide an additional device to the anatomy to obtain biological matter (e.g., tissue), such as by passage through or attachment to lumen 20436.

The biological sample matter can be removed from the patient, typically by removal of the additional device from the auxiliary device, so that the removed biological matter can be analyzed to diagnose one or more conditions of the patient. According to several examples, the mother-daughter endoscope assembly (including the main scope 20400 and the auxiliary scope 20434) can include additional device features, such as forceps or an auger, for gathering and removing cancerous or pre-cancerous matter (e.g., carcinoma, sarcoma, myeloma, leukemia, lymphoma and the like), or performing endometriosis evaluation, biliary ductal biopsies, and the like.

The controller 20408 can include, or be coupled to, an endoscopic procedure data generator 20450, and a treatment plan generator 20460. The endoscopic procedure data generator 20450 can generate images of an anatomical target, such as strictures or stenosis in the biliary and pancreatic ductal system. In an example, the endoscopic procedure data generator 20450 can generate real-time endoscope images of the anatomical target and its surrounding environment using an imaging sensor on the endoscope, such as a camera located at the functional section 1730 of the endoscope 1714. In some examples, the endoscopic procedure data generator 20450 can receive images from external imaging devices such as X-ray or fluoroscopy images, electrical potential map or an electrical impedance map, CT scans, MRI scans such as obtained in MRCP, or acoustic images such as EUS images, among others. The endoscopic procedure data generator 450 may additionally generate or receive other procedure-related information, including sensor information (e.g., sensors associated with the endoscope or with a therapeutic device passing through the endoscope), device information, patient medical history etc. In some examples, the endoscopic procedure data generator 20450 can retrieve, such as from a database, stored control log data (e.g., time-series data) of past endoscopic procedures performed by a plurality of physicians on a plurality of patients. The control log data can represent preferred cannulation and endoscope navigation approaches and habits of physicians with different experience levels.

The treatment plan generator 20460, which is an example of the treatment generator 1844 as illustrated in FIG. 18, can automatically generate a deployment plan for placing a stricture management device (SMD) at a target deployment site, and estimate a migration risk of a previously deployed SMD. The generation of the deployment plan and the estimation of the migration risk can be based on images, among other information produced by the endoscopic procedure data generator 20450. The SMD deployment plan can include an identification of SMD deployment site, characteristics such as tissue malignancy at the identified deployment site, and a navigation path for navigating the endoscope (or other steerable elongate instruments over which the SMD is deployed) and placing the SMD at the identified deployment site, among other treatment or control parameters. According to some examples, the SMD deployment plan and/or the estimation of the SMD migration risk can be generated using a trained machine-learning (ML) model. Images of the deployment site (e.g., the stricture), the SMD deployment plan, and the estimated migration risk of a deployed SMD can be displayed to the operating physician. The SMD deployment plan may also be provided to a robot system to facilitate a robot-assisted procedure.

FIGS. 20B-20C are diagrams illustrating an example of endoscopic placement of a pancreaticobiliary stent in ERCP, and migration of a previously deployed stent away from its deployment site. In FIG. 20B, stricture tissue 20480, such as scar tissue or tumors, causes blockage or narrowing of normal duct drainage in common bile duct 20312. A biliary ductal stent 20470 can be delivered through the duodenoscope 20400, bypass the stricture tissue 20480, and placed at a location in the common bile duct 20312. The stent 20470 can be made of plastic, or metal wires. A plastic stent can be pushed through the ERCP scope (e.g., the duodenoscope 20400) into a blocked duct to allow normal drainage. A metal stent can be more flexible and spring open to a larger diameter than plastic stents. Generally, metal stents are permanent while plastic stents can be easily removed at a repeat procedure.

Stent dislocation and proximal or distal migration are among the frequent complications associated with bile duct stents. FIG. 20C illustrates an example of proximal stent migration, where a distal end of a previously placed stent 20470 migrates intraluminally from its original ductal location 20472A into more distal location 20472B of the common bile duct or the hepatic duct. Proximal stent migration can cause biliary obstruction and cholangitis. Migrated stent can be retrieved via indirect traction with a balloon, or direct grasping of the stent with a wire basket, snare, or forceps. A new stent may be deployed at a desired deployment site of the common bile duct.

FIG. 21 is a block diagram illustrating an example of an SMD deployment and risk management system 21500 that can be configured to automatically determine an SMD deployment plan and estimate risks of adverse events or complications associated with deployment or use of and SMD, such as migration or dislodgment risk. The system 21500 can be a part of the control unit 1716 in FIG. 17, or the controller 20408 in FIG. 20A along with other devices or functional units such as the endoscopic procedure data generator 20450 and the treatment plan generator 20460 shown and discussed in for FIG. 20A. As illustrated in FIG. 21, the system 21500 can include a processor 21510, a device controller 21520, an input interface 21530, and a user interface device 21540. In some examples, the system 21500 can include or be communicatively coupled to an endoscopic procedure database 21506.

The processor 21510 may include circuit sets comprising one or more other circuits or sub-circuits that may, alone or in combination, perform the functions, methods, or techniques described herein. In an example, the processor 21510 and the circuits sets therein may be implemented as a part of a microprocessor circuit, which may be a dedicated processor such as a digital signal processor, application specific integrated circuit (ASIC), microprocessor, or other type of processor for processing information including physical activity information. Alternatively, the microprocessor circuit may be a general-purpose processor that may receive and execute a set of instructions of performing the functions, methods, or techniques described herein. In an example, hardware of the circuit set may be immutably designed to carry out a specific operation (e.g., hardwired). In an example, the hardware of the circuit set may include variably connected physical components (e.g., execution units, transistors, simple circuits, etc.) including a computer readable medium physically modified (e.g., magnetically, electrically, moveable placement of invariant massed particles, etc.) to encode instructions of the specific operation. In connecting the physical components, the underlying electrical properties of a hardware constituent are changed, for example, from an insulator to a conductor or vice versa. The instructions enable embedded hardware (e.g., the execution units or a loading mechanism) to create members of the circuit set in hardware via the variable connections to carry out portions of the specific operation when in operation. Accordingly, the computer readable medium is communicatively coupled to the other components of the circuit set member when the device is operating. In an example, any of the physical components may be used in more than one member of more than one circuit set. For example, under operation, execution units may be used in a first circuit of a first circuit set at one point in time and reused by a second circuit in the first circuit set, or by a third circuit in a second circuit set at a different time.

The processor 21510 may generate an SMD deployment plan using various sources of data specific to a patient received from the input interface 21530. In some embodiments, the input interface 21530 may be a direct data link between the system 21500 and one or more medical devices that generate at least some of the input features. For example, the input interface 21530 may transmit endoscopic images 21531, external image sources 21532, or sensor signals 21534 directly to the system 21500 during a therapeutic and/or diagnostic medical procedure. Additionally or alternatively, the input interface 21530 may be a classical user interface that facilitates interaction between a user and the system 21500. For example, the input interface 21530 may facilitate a user interface through which the user may manually enter some input data to the system 21500. Additionally or alternatively, the input interface 530 may provide the system 500 with access to an electronic patient record from which one or more data features may be extracted. In any of these cases, the input interface 21530 can collect one or more of the following sources of data in association with a specific patient on or before a time at which the system 21500 is used to identify an anatomical target and generate a treatment plan to treat said target.

By way of example and not limitation, data received from the input interface 21530 may include one or more of endoscopic images 21531 of the target anatomy, external image sources 21532, endo-therapeutic device information 21533, sensor signals 21534, or physician/patient information 21535, as illustrated in FIG. 21. The endoscopic images 21531 may include real-time endoscope images of potential SMD deployment sites (e.g., biliary duct strictures), or images of previously placed SMD and the anatomical environment at the deployment site, which can be captured by an imaging sensor associated with the endoscope during an endoscopic procedure, such as DPOC or ERCP as described above. The external image sources 21532 may include pre- or peri-procedural images acquired by external imaging devices other than the endoscope, which may include, for example, X-ray or fluoroscopy images, electrical potential map or an electrical impedance map, CT images, MRI images such as images obtained during MRCP, or acoustic images such as EUS images, among others, among others. The endo-therapeutic device information 21533 may include specification data, including size, dimension, shape, and structures of the endoscope used in an ERCP procedure or other steerable instruments such as a cannular, a catheter, or a guidewire; size, dimension, shape, and structures of SMDs for stricture management. Such device specification information may be used to determine cannulation or navigation parameter values such as the angle and/or the force applied to the device, or for selecting suitable SMD (e.g., stent of a proper size). The sensor signals 21534 may be acquired by sensors coupled to the endoscope or a treatment device passing through the endoscope, or otherwise associated with the patient. In an example, the sensor signals 21534 may include position, direction, or proximity of a distal portion of the endoscope relative to an anatomical target, sensed by a proximity sensor at a distal portion of the endoscope. In another example, the sensor signals 21534 may include stent shape or a change thereof indicative of a stent deformation, sensed by a sensor associated with the stent. The physician/patient information 21535 may include the operating physician's habits or preference of using a steerable elongate instrument, such as a preferred approach for cannulation and endoscope navigation, or past procedures of the similar type to the present procedure performed by the physician and the corresponding procedure outcome (e.g., success/failure assessment, procedure time, prognosis and complications). The physician/patient information 21535 may include patient information, including patient demographics (e.g., age, gender, race), patient medical history such as prior endoscopic procedures and images or data associated therewith, etc. The endoscope control log data 21536 may include time-series data representing changes in the movement and deflection of the device (e.g., endoscope, catheter, or cannula) on the endoscopic image as being maneuvered during a procedure.

The processor 21510 may include one or more of a deployment site identification and registration unit 21514, a complication risk estimator 21516, and a navigation and treatment parameter unit 21518. The deployment site identification and registration unit 21514 can use an input image (e.g., endoscopic images 21531 and/or external image sources 21532) of the stricture to automatically identify one or more locations for deploying an SMD, such as different locations in the biliary duct affected by stricture or stenosis and suitable for stent placement. The deployment site identification and registration unit 21514 can further identify one or more characteristics of a deployment site, such as stricture level, inflammation of neighboring tissue, or malignancy state of the stricture. In some examples, the deployment site identification and registration unit 21514 can extract image features (e.g., statistical or morphological features) from the input image, and identify the deployment site and its characteristics based on the extracted image features.

The deployment site identification and registration unit 21514 can register the identified deployment site. Alternatively, a user can manually register the deployment sites. The registered deployment sites, along with other treatment parameters (e.g., navigation routes, direction, angle, force applied to the cholangioscope or the stent) generated by the navigation and treatment parameter unit 21518 (as to be further discussed below), can be presented to the operating physician to assist in endoscopic stent placement, or provided to a robotic system to facilitate robot-assisted stent placement.

The complication risk estimator 21516 can estimate risks of adverse events or complications associated with deployment or use of an SMD. By way of example and not limitation, the complication risk estimator 516 can estimate a risk of a previously placed stent being migrated or dislodged from its deployment site. The migration risk can be correlated to a degree of deformation of the stent from its pre-deployment state. The complication risk estimator 21516 can determine a degree of stent deformation, and estimate the stent migration risk based on the degree of stent deformation. In an example, stent deformation can be determined using an input image (e.g., endoscopic images 21531 and/or external image sources 21532) of the previously placed stent and its neighboring environment, or image features extracted from the input image that are indicative of a shape or a change in shape (deformation) of the stent. In an example, the image features can include a shape or geometric measurements such as stent diameter, lumen diameter or area. The complication risk estimator 516 can determine a degree of stent deformation based on a change in shape or geometric measurements from stent images prior to deployment, or from stent specification. In another example, the image features can include a curvature of a specific portion of the stent image. The complication risk estimator 21516 can determine a degree of stent deformation based on a change in curvature from a baseline stent image (e.g., taken at stent placement). In yet another example, the image features can include a count of curved sections on the stent image. The complication risk estimator 21516 can determine a degree of stent deformation based on the number of curved sections.

The complication risk estimator 21516 can determine an elevated stent migration risk if the degree of stent deformation exceeds a threshold value (e.g., a curvature change threshold, or a curved section count threshold). In some examples, the estimated migration risk can have a numerical value (e.g., from 1 to 5 wherein 1 indicates the lowest risk level and 5 the highest risk level) or a categorical value (e.g., High, Medium, or Low). The complication risk estimator 21516 can determine a categorical or numerical migration risk level based on a comparison of the degree of stent deformation with multiple thresholds (e.g., multiple curvature change thresholds, or curved section count thresholds). For example, the complication risk estimator 21516 can determine a "High" migration risk if the stent deformation exceeds a first threshold $TH_1$, a "Medium" migration risk if the stent deformation is between the first threshold $TH_1$ and a second threshold $TH_2$ lower than $TH_1$, or a "Low" migration risk if the stent deformation is below the second threshold $TH_2$.

In addition or alternative to the input images, other data from the input interface 21530 may be used to estimate the stent migration risk. In an example, the complication risk estimator 21516 can estimate the migration risk using a sensor signal produced by a sensor included in or associated with the stent. The sensor signal can be indicative of a shape (e.g., geometric measurements such as stent diameter, lumen diameter or area) or a change in shape (e.g., collapsing, bending, twisting, or other forms of stent deformation). In some examples, the complication risk estimator 21516 can estimate the migration risk using characteristics of tissue at the stent deployment site such as inflammation status, stricture or stenosis level, malignancy state, or size and shape of an anatomical target (e.g., biliary ductal calculi) to be passed through the lumen of the popped stent.

In some examples, the complication risk estimator 21516 can estimate the migration risk assessment in response to a trigger event, such as an endoscopic procedure interacting with the SMD, such as endoscopic extraction of unwanted tissue or calculi structures through the stent, or stent repositioning, extraction, or modification.

The navigation and treatment parameter unit 21518 can automatically estimate navigation or treatment parameters for an endoscope or a treatment tool (e.g., an SMD delivered over the endoscope) used in an endoscopic procedure. In an example, the navigation and treatment parameter unit 21518 can automatically estimate a position of the distal portion (e.g., the functional section 1730 of the endoscope 1714 as shown in FIG. 17) of an endoscope or other steerable elongate instrument relative to an anatomical target of interest, such as a distance from the endoscope distal portion to duodenal papilla; a heading direction of the distal portion of the steerable elongate instrument relative to the anatomical target; an insertion angle of a cannula or a surgical element used in cannulation; a protrusion amount of a cannula or a surgical element; a speed or a force applied to the endoscope distal portion or a surgical element; a rotational direction or a cutting area of a surgical element; among others. In another example, the navigation and treatment parameter unit 21518 can automatically estimate navigation and operational parameters for deploying a stent. In the case of a previously placed stent with an elevated migration risk (such as a "High" risk as determined by the complication risk estimator 21516), the navigation and treatment parameter unit 21518 can automatically determine corrective actions such as navigation routes for repositioning, extracting, or modifying said stent, schedule patient follow-up visits (e.g., next appointment date and diagnostic or treatment options for the patient), among others. In some examples, the navigation and treatment parameter unit 21518 can estimate a probability of success, or estimated procedure time for an endoscopic stricture management procedure in accordance with the estimated navigation or treatment parameters.

One or more of the deployment site identification and registration unit 21514, the complication risk estimator 21516, or the navigation and treatment parameter unit 21518 can use one or more trained machine-learning (ML) models 21512 to perform their respective tasks as stated above. The ML model(s) can have a neural network structure comprising an input layer, one or more hidden layers, and an output layer. The input interface 21530 may deliver one or more sources of input data, or features generated therefrom, into the input layer of the ML model(s) 21512 which propagates the input data or data features through one or more hidden layers to the output layer. The ML model(s) 21512 can provide the system 21500 with the ability to perform tasks, without explicitly being programmed, by making inferences based on patterns found in the analysis of data. The ML model(s) 21512 explores the study and construction of algorithms (e.g., ML algorithms) that may learn from existing data and make predictions about new data. Such algorithms operate by building the ML model(s) 21512 from training data in order to make data-driven predictions or decisions expressed as outputs or assessments.

The ML model(s) 21512 may be trained using supervised learning or unsupervised learning. Supervised learning uses prior knowledge (e.g., examples that correlate inputs to outputs or outcomes) to learn the relationships between the inputs and the outputs. The goal of supervised learning is to learn a function that, given some training data, best approximates the relationship between the training inputs and outputs so that the ML model can implement the same relationships when given inputs to generate the corresponding outputs. Unsupervised learning is the training of an ML algorithm using information that is neither classified nor labeled, and allowing the algorithm to act on that information without guidance. Unsupervised learning is useful in exploratory analysis because it can automatically identify structure in data.

Common tasks for supervised learning are classification problems and regression problems. Classification problems, also referred to as categorization problems, aim at classifying items into one of several category values. Regression algorithms aim at quantifying some items (for example, by providing a score to the value of some input). Some examples of commonly used supervised-ML algorithms are Logistic Regression (LR), Naive-Bayes, Random Forest (RF), neural networks (NN), deep neural networks (DNN), matrix factorization, and Support Vector Machines (SVM). Examples of DNN include a convolutional neural network (CNN), a recurrent neural network (RNN), a deep belief network (DBN), or a hybrid neural network comprising two or more neural network models of different types or different model configurations.

Some common tasks for unsupervised learning include clustering, representation learning, and density estimation. Some examples of commonly used unsupervised learning algorithms are K-means clustering, principal component analysis, and autoencoders.

Another type of ML is federated learning (also known as collaborative learning) that trains an algorithm across multiple decentralized devices holding local data, without exchanging the data. This approach stands in contrast to traditional centralized machine-learning techniques where all the local datasets are uploaded to one server, as well as to more classical decentralized approaches which often assume that local data samples are identically distributed. Federated learning enables multiple actors to build a common, robust machine learning model without sharing data, thus allowing to address critical issues such as data privacy, data security, data access rights and access to heterogeneous data.

As illustrated in FIG. 21, the ML model(s) 21512 may be trained using a training module 21511, which can be included in the processor 21510 as shown in FIG. 21. Alternatively, the training module 21511 can be implemented in a separate unit. To train an ML model, a training dataset can be constructed using past endoscopic procedure data such as selected and retrieved from the endoscopic procedure database 21506. The training data may include procedure data acquired during respective endoscopic procedures performed on a plurality of patients. The endoscopic procedures can be those of the same type as the endoscopic procedure to be performed on the present patient. The training data can be from various data sources, such as any of those shown in the input interface 21530. The training data used for training an ML model can vary depending on the parameters to estimate. In an example of a ML-based determination of canulation and endoscope navigation, the training data can include endoscopic images or videos showing patient anatomy, cannulation and endoscope navigation routes, progress of cannulation or navigation, among other information. In another example of a ML-based estimation of stent migration risk, the training data can include past endoscopic images or images from external sources showing the previously placed stent and its neighboring environment, sensor signals (e.g., via a sensor included in or associated with the stent) indicative of a shape or a change in shape of the stent, or characteristics of tissue at the stent deployment site.

In an example, the training data can be screened such that only data of procedures performed by certain physicians (such as those with substantially similar experience levels to the operating physician), and/or data of procedures on certain patients with special requirement (such as those with substantially similar anatomy or patient medical information to the present patient) are included in the training dataset. In an example, the training data can be screened based on a success rate of the procedure, including times of attempts before a successful cannulation or navigation, such that only data of procedures with a desirable success rate achieved within a specified number of attempts are included in the training dataset. In another example, the training data can be screened based on complication associated with the patients. In some examples, particularly in case of a small training dataset (such as due to data screening), the ML model can be trained to identify stent deployment sites and determine navigation and treatment parameters (e.g., navigation paths for the endoscope and operational parameters for stent placement) by extrapolating, interpolating, or bootstrapping the training data, thereby creating an SMD deployment plan specifically tailored to the specific patient and physician. The training of the ML model may be performed continuously or periodically, or in near real time as additional procedure data are made available. The training involves algorithmically adjusting one or more ML model parameters, until the ML model being trained satisfies a specified training convergence criterion.

In some examples, a plurality of ML models can be separately trained, validated, and used (in an inference phase) in different applications, such as estimating different parameters of the devices used in an endoscopic procedure or planning of such a procedure. For example, a first ML model (or a first set of ML models) may be trained to establish a correspondence between (i) endoscopic images and/or other external images of strictures being treated with stents from past endoscopic procedures (optionally along with other information) and (ii) various stent deployment sites and characteristics therein (e.g., stricture or stenosis level, inflammation of neighboring tissue, or malignancy state of the stricture). The trained first ML model(s) can be used by the deployment site identification and registration unit 21514 in an inference phase to identify, from an input image (or a sequence of images or a live video) of strictures (optionally along with other information), one or more recommended stent deployment sites and estimated characteristics (e.g., malignancy of the stricture at the deployment site).

In an example, a second ML model (or a second set of ML models) may be trained to establish a correspondence between (i) endoscopic images and/or other external images of stents and respective neighboring environment from past endoscopic procedures, or image features extracted from the stent images indicative of stent deformation (e.g., curvatures or a count of curved sections on the stent image); and (ii) incidents of stent migration in those past endoscopic procedures. The trained second ML model(s) can be used by the complication risk estimator 21516 in an inference phase to automatically determine, from an input image (or a sequence of images or a live video) of a previously placed stent (optionally along with other information), an estimate of stent migration risk. As stated above, the estimated migration risk can have a numerical value (e.g., from 1 to 5 wherein 1 indicates the lowest risk level and 5 the highest risk level) or a categorical value (e.g., High, Medium, or Low).

In an example, a third ML model (or a third set of ML models) may be trained to establish a correspondence between (i) endoscopic images and/or other external images of anatomical targets from past endoscopic procedures (optionally along with other information) and (ii) navigation and treatment parameters in those past procedures, including direction, angle, speed, force, and amount of intrusion for navigating and placing endoscopes, catheters, or SMD devices (e.g., stents) to the anatomical target, or estimated success rate and procedure time, among other parameters. The trained third ML model(s) can be used by the navigation and treatment parameter unit 21518 in an inference phase to automatically determine, from an input image of patient anatomy including the anatomical target (optionally along with other information), proper navigation and treatment parameters for deploying a new stent, or repositioning, extracting, or modifying a previously placed stent determined to be at an elevated risk of migration (such as determined by the complication risk estimator 21516), among other corrective actions. In some examples, the trained third ML models(s) can be trained to generate recommended schedule of a follow-up visit, such as next appointment date and diagnostic or treatment options for the patient.

The device controller 21520 can generate a control signal to one or more actuators 21550, such as a motor actuating a robot arm. The one or more actuators 21550 can be coupled to a steerable elongate instrument, which can be a diagnostic or therapeutic endoscope, a cannula, a catheter, a guidewire, or a guide sheath, among others. The steerable elongate instrument may include a treatment tool (e.g., a lithotripsy device or a calculi extraction device) robotically operable via the one or more actuators 21550. In response to the control signal, the one or more actuators 21550 can robotically adjust position, posture, direction, and navigation path of the steerable elongate instrument (e.g., an endoscope) and a treatment tool included therein (e.g., a stent passed through the lumen the endoscope) in accordance with the navigation and treatment parameters estimated by the navigation and treatment parameter unit 21518.

As some of the canulation or navigation parameters (e.g., positions, angle, direction, navigation path) associated with a cannula or GW are determined based on images (e.g., endoscopic images or other images) generated an imaging system, such canulation or navigation parameters are with reference to the coordinates of the imaging system. To facilitate robotic control of the cannula or GW in accordance with the canulation or navigation parameters, in some examples the coordinates of the robotic system may be registered with the coordinates of the imaging system, such that an anatomical position in the coordinates of the imaging system can be mapped to a corresponding position in the coordinates of the robotic system. Such registration may be performed, for example, by using distinct landmarks whose positions are known in respective coordinate systems. The registration may be intensity- or feature-based, and can be represented by transformation model (a linear or a non-linear model) that maps the coordinates of imaging system to the coordinates of the robotic system.

The user interface device 21540 can include an output unit 21542 and an input unit 21545, which are examples of the output unit 1718 and the input unit 1720 respectively as shown in FIG. 18. The input unit 21545 can receive input from the user or from other data sources. In an example, the input interface 21530 can be included in the input unit 21545. The output unit 21542 can include a display 21543 that can display images of the stent deployment site and characteristics of the deployment site, as identified by the deployment site identification and registration unit 21514. For an existing stent, dislodgment or migration risk of such stent, estimated by the complication risk estimator 21516, can also be displayed on the display 21543. In some examples, the display 21543 can present a graphical representation of the navigation of an endoscope and the placement of the stent based on the navigation parameters produced by the navigation and treatment parameter unit 21518.

In an example, the displayed region of the target anatomy images can be automatically adjusted according to the position or direction of a distal end of the endoscope relative to an anatomical target. For example, the output unit 21542 may automatically zoom in an image as the endoscope tip gets closer to the papilla to show more details of the papilla. Alternatively, the zooming function can be activated and adjusted manually by the user (e.g., operating physician) via the input unit 21545. In an example, the output unit 21542 can display a cross-section view of an anatomy in a direction specified by a user, such as via the input unit 21545. In an example, the user may adjust viewing angle (e.g., rotating the view) and have a 360-degree view of the reconstructed or integrated 3D images via the input unit 21545. In an example, at least a portion of the input unit 21545 can be incorporated into the endoscope, such as the handle section 1732 of endoscope 14 in FIG. 17, to facilitate user operation during the procedure.

In some examples, the display 21543 may automatically center the target anatomy in a viewing area, such as based on the distance and viewing angle of the imaging device (e.g., camera) relative to the target anatomy. In an example, the device controller 21520 can control the positioning and direction of the endoscope to adjust viewing angle of the imaging device to achieve auto-centering of the target anatomy. Additionally or alternatively, the device controller 21520 can control an image processor to post-process the acquired image including repositioning the identified target anatomy at the center of the viewing area.

In some examples, the output unit 21542 may display on the image a visual indication of the target anatomy (e.g., duodenal papilla), a projected navigation path toward the target anatomy; or a progression of the endoscope toward the targe anatomy along the projected navigation path. Display settings can be adjusted by the user via the input unit 21545. The visual indication may take the format of markers, annotations (icons, texts, or graphs), highlights, or animation, among other visual indicators. For example, markers of different shapes, colors, forms, or sizes can be display on the reconstructed or integrated image to distinguish different tissue, anatomical regions, their accessibility or criticality.

The output unit 21542 can include an alert and feedback generator 21544 that can generate an alert, a notification, or other formats of human-perceptible feedback to the operating physician on the status or progress of the cannulation or navigation in reference to the navigation plan. For example, an alert can be generated to indicate a risk of tissue damage associated with improper cannulation. The feedback can be in one or more forms of audio feedback, visual feedback, or haptic feedback. For example, when the endoscope tip enters or comes closer to a "critical zone" (e.g., proximity sensor detecting a distance to a critical anatomy of interest shorter than a threshold distance), the critical zone can be shown in different colors to represent such distance (e.g., green zone, yellow zone, and read zone as the endoscope gets closer to the critical zone). Additionally or alternatively, haptic feedback such as touch or vibration may be generated and felt by the operating physician. In an example, the alert and feedback generator 21544 can automatically adjust the vibration strength according to the distance to the critical zone. For example, a low vibration can be generated when the endoscope tip is in a green zone. If the system predicts, based on present advancing speed and direction of the endoscope, that the endoscope tip will reach the critical zone in a time lower than a predetermined threshold, then alert and feedback generator 21544 can apply moderate vibration when the endoscope tip reaches a yellow zone, and apply high vibration when the endoscope tip reaches red zones to indicate a risk of tissue damage. The real-time alert and feedback in an image-guided endoscopic procedure as described herein can improve the efficiency of cannulation and endoscope navigation, especially for inexperienced physicians, and can improve endoscopic procedure success rate and patient outcome.

FIGS. 22A-22B are diagrams illustrating an example of training an ML model and using the trained ML model to determine a migration risk of a pancreaticobiliary stent and treatment recommendations. FIG. 22A illustrates an ML model training (or learning) phase during which an ML model 640 may be trained using training data comprising a plurality of images 610 from past endoscopic procedures performed on a plurality of patients. The plurality of images 610 each shows respective biliary stents 611 and the neighboring environment such as strictures. The training data may also include stent information (e.g., type, location, curvature or other geometric characteristics) and patient information. The training data may also include annotated procedure data 620, including incidents of stent migration in each of the past procedures corresponding to the plurality of images 610. The ML model 640 can be trained using supervised learning, unsupervised learning, or reinforcement leaning. Examples of ML model architectures and algorithms may include, for example, decision trees, neural networks, support vector machines, or a deep-learning networks, etc. Examples of deep-learning networks include a convolutional neural network (CNN), a recurrent neural network (RNN), a deep belief network (DBN), or a hybrid neural network comprising two or more neural network models of different types or different model configurations.

The training of the ML model may be performed continuously or periodically, or in near real time as additional procedure data are made available. The training involves algorithmically adjusting one or more ML model parameters, until the ML model being trained satisfies a specified training convergence criterion. The trained ML model 640 can establish a correspondence between the images of stents and respective neighboring environment from past endoscopic procedures and the stent migration risks in those past endoscopic procedures.

FIG. 22B illustrates an inference phase during which a live image 630 is applied to the trained ML model 640. The live image 630 shows a previously placed biliary stent 631 and its neighboring environment. An estimate of migration risk of the stent 631 can be determined and communicated to a user (e.g., a clinician) to guide a treatment procedure. As stated above, the estimated migration risk can have a numerical value (e.g., from 1 to 5 wherein 1 indicates the lowest risk level and 5 the highest risk level) or a categorical value (e.g., High, Medium, or Low). Additionally or alternatively, the tool recommendation may be used to facilitate robotic maneuvering of the tools in a robot-assisted procedure.

In some examples, the ML model 640 (or a different ML model) may be trained to provide recommended preventive or corrective actions to mitigate the stent migration risk. As illustrated in FIG. 22A, the training data can include the plurality of images 610, and the annotated procedure data 620 that includes migration prevention/correction parameters, such as values of navigation and treatment parameters for navigating an endoscope or other treatment tools to reposition, retrieve, or modify a stent with a specific migration risk, such as a "High" migration risk. During the inference phase as shown in FIG. 22B, the live image 630 is applied to the trained ML model 640 to determine recommended migration preventive/correction parameters 650 for repositioning, extracting, or modifying the stent 631 if such stent is estimated to have a specific migration risk level, such as a "High" migration risk.

FIG. 23 is a flow chart illustrating an example method 700 for managing risks of adverse events or complications associated with deployment or use of a stricture management device (SMD), such as a migration or dislodgment risk of a pancreaticobiliary stent. The method 700 can be implemented in and executed by the SMD deployment and risk management system 500 as illustrated in FIG. 21. The anatomical target can include soft or hard tissue, or calculi in kidney, gallbladder, ureter, among other stone-forming regions. Although the processes of the method 700 are drawn in one flow chart, they are not required to be performed in a particular order. In various examples, some of the processes can be performed in a different order than that illustrated herein.

At 710, patient information including an image of the deployed SMD can be provided for use in automatic migration risk assessment. The image of the anatomical target may include real-time endoscope images of the previously placed SMD (e.g., a stent) and its neighboring environment captured by an imaging sensor associated with the endoscope during an endoscopic procedure, such as DPOC or ERCP, or images from other sources including, for example, X-ray or fluoroscopy images, electrical potential map or an electrical impedance map, CT images, MRI images such as images obtained from Magnetic resonance cholangiopancreatography (MRCP) procedures, or acoustic images such as endoscopic ultrasonography (EUS) images, among others. In addition to the images of the anatomical target, other information may be used in the procedure planning process, including, for example, endo-therapeutic device information, sensor signals, physician information (e.g., the operating physician's habits or preference of using the steerable elongate instrument), and endoscope control log data, as described above with reference to FIG. 21.

At 720, a complication risk associated with the deployment or use of the SMD can be estimated based on the image of the SMD. By way of example and not limitation, the complication risk can include a risk of the SMD migrating away from the anatomical target. In an example, the complication risk can be estimated using a trained machine-learning (ML) model and at least the image of the SMD received at 710. The ML model may be trained using procedure data from past endoscopic procedures on a plurality of patients. The past procedure data can include images of SMDs deployed at respective anatomical targets from past procedures on a plurality of patients and assessments of migration risks of the SMDs at respective anatomical targets. In some examples, the image of the deployed SMD can be processed to extract image features indicative of a shape or a change in shape (deformation) of the SMD. The exacted image features may be applied to the trained ML model to determine a degree of deformation of the SMD and further to estimate a migration risk base on the degree of deformation. In an example, the image features can include a shape or geometric measurements such as stent diameter, lumen diameter or area, and the trained ML model can determine a degree of stent deformation based on a change in shape or geometric measurements from stent images prior to deployment, or from stent specification. In another example, the image features can include a curvature of a specific portion of the stent image, and the trained ML model can determine a degree of stent deformation based on a change in curvature from a baseline stent image (e.g., taken at stent placement). In yet another example, the image features can include a count of curved sections on the stent image, and the trained ML model can determine a degree of stent deformation based on the number of curved sections.

The same trained ML model, or a separately trained ML model may automatically estimate navigation or treatment parameters for an endoscope or a treatment tool (e.g., an SMD delivered over the endoscope) used in an endoscopic procedure. In an example, the trained ML model can be used to estimate a position of the distal portion of an endoscope or other steerable elongate instrument relative to an anatomical target of interest.

At 730, the estimated complication risk for a deployed SMD generated at 720 may be presented to a user, such as being displayed on a display of a user interface. The estimated risk can have a numerical value (e.g., from 1 to 5 wherein 1 indicates the lowest risk level and 5 the highest risk level) or a categorical value (e.g., High, Medium, or Low). In some examples, an ML model may be trained to automatically identify one or more locations for deploying an SMD, such as different locations in the biliary duct affected by stricture or stenosis and suitable for stent placement, and estimate navigation and operational parameters for deploying an SMD, based on the image of the stricture tissue. The trained ML model may further identify one or more characteristics of the potential deployment site, such as stricture or stenosis level, inflammation of neighboring tissue, or malignancy state of the stricture, can be determined. The images of the stent deployment site and characteristics of the deployment site may be displayed on a user interface.

At 740, a recommended action for correcting SMD migration can be generated such as by using the trained ML model. The recommended action can include, for example, navigation routes for endoscopically repositioning, extracting, or modifying the migrated stent depending upon the migration risk, or schedule patient follow-up visits (e.g., next appointment date and diagnostic or treatment options for the patient), etc.

FIG. 24 illustrates generally a block diagram of an example machine 800 upon which any one or more of the techniques (e.g., methodologies) discussed herein may perform. Portions of this description may apply to the computing framework of various portions of the SMD deployment and risk management system 500, such as the processor 510 and the device controller 520.

In alternative embodiments, the machine 800 may operate as a standalone device or may be connected (e.g., networked) to other machines. In a networked deployment, the machine 800 may operate in the capacity of a server machine, a client machine, or both in server-client network environments. In an example, the machine 800 may act as a peer machine in peer-to-peer (P2P) (or other distributed) network environment. The machine 800 may be a personal computer (PC), a tablet PC, a set-top box (STB), a personal digital assistant (PDA), a mobile telephone, a web appliance, a network router, switch or bridge, or any machine capable of executing instructions (sequential or otherwise) that specify actions to be taken by that machine. Further, while only a single machine is illustrated, the term "machine" shall also be taken to include any collection of machines that individually or jointly execute a set (or multiple sets) of instructions to perform any one or more of the methodologies discussed herein, such as cloud computing, software as a service (SaaS), other computer cluster configurations.

Examples, as described herein, may include, or may operate by, logic or a number of components, or mechanisms. Circuit sets are a collection of circuits implemented in tangible entities that include hardware (e.g., simple circuits, gates, logic, etc.). Circuit set membership may be flexible over time and underlying hardware variability. Circuit sets include members that may, alone or in combination, perform specified operations when operating. In an example, hardware of the circuit set may be immutably designed to carry out a specific operation (e.g., hardwired). In an example, the hardware of the circuit set may include variably connected physical components (e.g., execution units, transistors, simple circuits, etc.) including a computer readable medium physically modified (e.g., magnetically, electrically, moveable placement of invariant massed particles, etc.) to encode instructions of the specific operation. In connecting the physical components, the underlying electrical properties of a hardware constituent are changed, for example, from an insulator to a conductor or vice versa. The instructions enable embedded hardware (e.g., the execution units or a loading mechanism) to create members of the circuit set in hardware via the variable connections to carry out portions of the specific operation when in operation. Accordingly, the computer readable medium is communicatively coupled to the other components of the circuit set member when the device is operating. In an example, any of the physical components may be used in more than one member of more than one circuit set. For example, under operation, execution units may be used in a first circuit of a first circuit set at one point in time and reused by a second circuit in the first circuit set, or by a third circuit in a second circuit set at a different time.

Machine (e.g., computer system) 800 may include a hardware processor 802 (e.g., a central processing unit (CPU), a graphics processing unit (GPU), a hardware processor core, or any combination thereof), a main memory 804 and a static memory 806, some or all of which may communicate with each other via an interlink (e.g., bus) 808. The machine 800 may further include a display unit 810 (e.g., a raster display, vector display, holographic display, etc.), an alphanumeric input device 812 (e.g., a keyboard), and a user interface (UI) navigation device 814 (e.g., a mouse). In an example, the display unit 810, input device 812 and UI navigation device 814 may be a touch screen display. The machine 800 may additionally include a storage device (e.g., drive unit) 816, a signal generation device 818 (e.g., a speaker), a network interface device 820, and one or more sensors 821, such as a global positioning system (GPS) sensor, compass, accelerometer, or other sensors. The machine 800 may include an output controller 828, such as a serial (e.g., universal serial bus (USB), parallel, or other wired or wireless (e.g., infrared (IR), near field communication (NFC), etc.) connection to communicate or control one or more peripheral devices (e.g., a printer, card reader, etc.).

The storage device 816 may include a machine readable medium 822 on which is stored one or more sets of data structures or instructions 824 (e.g., software) embodying or utilized by any one or more of the techniques or functions described herein. The instructions 824 may also reside, completely or at least partially, within the main memory 804, within static memory 806, or within the hardware processor 802 during execution thereof by the machine 800. In an example, one or any combination of the hardware processor 802, the main memory 804, the static memory 806, or the storage device 816 may constitute machine readable media.

While the machine-readable medium 822 is illustrated as a single medium, the term "machine readable medium" may include a single medium or multiple media (e.g., a centralized or distributed database, and/or associated caches and servers) configured to store the one or more instructions 824.

The term "machine readable medium" may include any medium that is capable of storing, encoding, or carrying instructions for execution by the machine 800 and that cause the machine 800 to perform any one or more of the techniques of the present disclosure, or that is capable of storing, encoding or carrying data structures used by or associated with such instructions. Non-limiting machine-readable medium examples may include solid-state memories, and optical and magnetic media. In an example, a massed machine-readable medium comprises a machine readable medium with a plurality of particles having invariant (e.g., rest) mass. Accordingly, massed machine-readable media are not transitory propagating signals. Specific examples of massed machine-readable media may include: non-volatile memory, such as semiconductor memory devices (e.g., Electrically Programmable Read-Only Memory (EPROM), Electrically Erasable Programmable Read-Only Memory (EPSOM)) and flash memory devices; magnetic disks, such as internal hard disks and removable disks; magneto-optical disks; and CD-ROM and DVD-ROM disks.

The instructions 824 may further be transmitted or received over a communication network 826 using a transmission medium via the network interface device 820 utilizing any one of a number of transfer protocols (e.g., frame relay, internet protocol (IP), transmission control protocol (TCP), user datagram protocol (UDP), hypertext transfer protocol (HTTP), etc.). Example communication networks may include a local area network (LAN), a wide area network (WAN), a packet data network (e.g., the Internet), mobile telephone networks (e.g., cellular networks), Plain Old Telephone (POTS) networks, and wireless data networks (e.g., Institute of Electrical and Electronics Engineers (IEEE) 802.11 family of standards known as WiFi®, IEEE 802.16 family of standards known as WiMax®), IEEE 802.15.4 family of standards, peer-to-peer (P2P) networks, among others. In an example, the network interface device 820 may include one or more physical jacks (e.g., Ethernet, coaxial, or phone jacks) or one or more antennas to connect to the communication network 826. In an example, the network interface device 820 may include a plurality of antennas to wirelessly communicate using at least one of single-input multiple-output (SIMO), multiple-input multiple-output (MIMO), or multiple-input single-output (MISO) techniques. The term "transmission medium" shall be taken to include any intangible medium that is capable of storing, encoding or carrying instructions for execution by the machine 800, and includes digital or analog communications signals or other intangible medium to facilitate communication of such software.

ADDITIONAL NOTES

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

54. An endoscopic system, comprising:
  an endoscope configured to deploy a stricture management device (SMD) at an anatomical target in a patient; and
  a processor configured to:
    receive an image of the SMD deployed at the anatomical target;
    derive, from the received image, information correlated to a risk of complication associated with deployment or use of the SMD at the anatomical target; and
    output the derived information correlated to the risk of complication.

55. The endoscopic system of example 54, wherein the derived information correlated to the risk of complication includes an estimate of a migration risk of the SMD migrating away from the anatomical target.

56. The endoscopic system of example 55, wherein the SMD includes a stent deployed at a portion of patient pancreaticobiliary system,
  wherein the processor is configured to estimate the migration risk of the stent in response to a procedure interacting with the SMD.

57. The endoscopic system of example 55, wherein the processor is configured to categorize the estimate of the migration risk into one of a plurality of risk levels.

58. The endoscopic system of example 54, wherein the derived information correlated to the risk of complication includes a recommended action to avoid or mitigate complication caused by deployment of the SMD at the anatomical target.

59. The endoscopic system of example 54, wherein the derived information correlated to the risk of complication includes a recommended schedule of a follow-up visit for the patient.

60. The endoscopic system of example 54, wherein the received image of the SMD includes one or more of an endoscopic image, an X-ray or fluoroscopy image, a computer tomography (CT) image, a magnetic resonance imaging (MRI) image, or an acoustic image.

61. The endoscopic system of example 54, wherein the processor is configured to:
  extract a morphological feature from the received image of the SMD; and
  derive the information correlated to the risk of complication further using the extracted morphological feature.

62. The endoscopic system of example 61, wherein the morphological feature includes a curvature of a curved portion of the received image of the SMD.

63. The endoscopic system of example 61, wherein the morphological feature includes a count of curved sections of the image of the SMD.

64. The endoscopic system of example 54, wherein the processor is configured to derive the information correlated to the risk of complication further using sensor data acquired by a sensor included in the SMD, the sensor data indicative of a shape or a change in shape of the SMD.

65. The endoscopic system of example 54, wherein the processor is configured to derive the information correlated to the risk of complication further using a characteristic of the anatomical target at which the SMD is deployed.

66. The endoscopic system of example 65, wherein the characteristic of the anatomical target includes a tissue inflammation state of the anatomical target.

67. The endoscopic system of example 65, wherein the SMD includes a stent deployed at a portion of patient pancreaticobiliary system, and the characteristic of the anatomical target includes size and shape of a tissue target or a calculi target to be extracted and passed through the stent.

68. The endoscopic system of example 54, wherein the processor is configured to derive the information correlated to the risk of complication further using information about a pre-deployment shape or geometry of the SMD.

69. The endoscopic system of example 54, wherein the processor is configured to derive the information correlated to the risk of complication further using patient demographic information.

70. The endoscopic system of example 54, wherein to derive the information correlated to the risk of complication, the processor is configured to apply the received image of the SMD to a trained machine-learning (ML) model to estimate the information correlated to the risk of complication.

71. The endoscopic system of example 70, wherein the processor includes a training module configured to train an ML model using a training dataset comprising (i) images of SMDs deployed at respective anatomical targets from past procedures on a plurality of patients and (ii) assessments of migration risks of the SMDs at respective anatomical targets.

72. The endoscopic system of example 71, wherein the training module is configured to train the ML model using supervised learning or unsupervised learning.

73. The endoscopic system of example 70, wherein the processor is configured to apply the received image of the SMD to the trained ML model to generate a recommended action for correcting SMD migration.

74. The endoscopic system of example 54, comprising a user interface configured to receive a user input designating a deployment site at the anatomical target for deploying the SMD via a steerable elongate instrument,
  wherein the processor is further configured to register the designated deployment site, and generate a deployment plan for navigating the steerable elongate instrument and deploying the SMD at the designated deployment site.

75. The endoscopic system of example 54, wherein the anatomical target includes an anatomical stricture in a vicinity of the deployed SMD,
  wherein the processor is further configured to receive an image of the anatomical stricture, and to estimate malignancy of the anatomical stricture using the received endoscopic image of the anatomical stricture.

76. The endoscopic system of example 54, comprising a user interface configured to present the derived information correlated to the risk of complication to the user.

77. The endoscopic system of example 54, comprising a controller configured to provide a control signal to an actuator to robotically facilitate a procedure with respect to the SMD based at least on the derived information correlated to the risk of complication.

78. A method of managing migration of a stricture management device (SMD) deployed at an anatomical target in a patient, the method comprising:

receiving patient information including an image of the deployed SMD;

deriving, from the received image, information correlated to a risk of complication associated with deployment or use of the SMD at the anatomical target; and outputting the derived information correlated to the risk of complication.

79. The method of example 78, wherein deriving the information correlated to a risk of complication includes estimating a migration risk of the SMD migrating away from the anatomical target.

80. The method of example 78, wherein the image of the SMD includes one or more of an endoscopic image, an X-ray or fluoroscopy image, a computer tomography (CT) image, a magnetic resonance imaging (MRI) image, or an acoustic image.

81. The method of example 78, comprising extracting a morphological feature from the image of the SMD, the morphological feature including one or more of a curvature of a curved portion or a count of curved sections on the image of the deployed SMD, wherein deriving the information correlated to the risk of complication further includes using the extracted morphological feature.

82. The method of example 78, wherein deriving the information correlated to the risk of complication further includes using one or more of:

a tissue inflammation state of the anatomical target at which the SMD is deployed;

a pre-deployment shape or geometry of the SMD; or patient demographic information.

83. The method of example 78, wherein the SMD includes a stent deployed at a portion of patient pancreaticobiliary system, wherein deriving the information correlated to the risk of complication further includes using size and shape of a tissue target or a calculi target to be extracted and passed through the stent.

84. The method of example 78, further comprising applying the image of the SMD to a trained machine-learning (ML) model to estimate the information correlated to the risk of complication.

85. The method of example 84, further comprising, via a training module, training an ML model using a training dataset comprising (i) images of SMDs deployed at respective anatomical targets from past procedures on a plurality of patients and (ii) assessments of migration risks of the SMDs at respective anatomical targets.

86. The method of example 78, further comprising:

receiving a user input designating a deployment site at the anatomical target for deploying the SMD via a steerable elongate instrument; and registering the designated deployment site and generating a deployment plan for navigating the steerable elongate instrument and deploying the SMD at the designated deployment site.

87. The method of example 78, wherein outputting the derived information correlated to the risk of complication includes presenting the derived information to a user interface, or providing a control signal to an actuator to robotically facilitate a procedure with respect to the SMD based at least on the derived information.

88. A non-transitory machine-readable storage medium that includes instructions that, when executed by one or more processors of a machine, cause the machine to perform operations comprising:

receiving an image of a stricture management device (SMD) deployed at an anatomical target of a patient;

deriving, from the received image, information correlated to a risk of complication associated with deployment or use of the SMD at the anatomical target; and outputting the derived information correlated to the risk of complication.

89. The non-transitory machine-readable storage medium of example 35, wherein the operation of deriving the information correlated to the risk of complication includes estimating a migration risk of the SMD migrating away from the anatomical target.

90. The non-transitory machine-readable storage medium of example 88, wherein the instructions cause the machine to perform operations including extracting a morphological feature from the image of the SMD, the morphological feature including one or more of a curvature of a curved portion or a count of curved sections on the image of the deployed SMD, wherein deriving the information correlated to the risk of complication further includes using the extracted morphological feature.

91. The non-transitory machine-readable storage medium of example 88, wherein the instructions cause the machine to perform operations including applying the image of the SMD to a trained machine-learning (ML) model to estimate the information correlated to the risk of complication.

92. The non-transitory machine-readable storage medium of example 88, wherein the instructions cause the machine to perform operations including:

receiving a user input designating a deployment site at the anatomical target for deploying the SMD via a steerable elongate instrument; and registering the designated deployment site and generating a deployment plan for navigating the steerable elongate instrument and deploying the SMD at the designated deployment site.

What is claimed is:

1. An endoscopic system, comprising:

a steerable elongate instrument configured to be positioned and navigated in a patient anatomy;

a processor configured to:

generate a pre-procedure treatment plan for treating an anatomical target prior to initiating treatment of the anatomical target;

receive patient information including real-time images of the anatomical target captured by an imaging sensor during an endoscopic procedure;

apply the received real-time images of the anatomical target to at least one trained machine-learning (ML) model to (i) identify the anatomical target and a characteristic thereof, and (ii) generate, based on the identified anatomical target and the characteristic thereof, an updated treatment plan based on the identified anatomical target and the characteristic thereof, wherein the at least one ML model performs a real-time analysis of the received real-time images to detect a change in one or more anatomical characteristics of the anatomical target and responsively automatically real-time update the updated treatment plan based on the detected change in the one or more anatomical characteristics of the anatomical target, wherein the identified anatomical target is a calculus, and wherein the detected change in the one or more anatomical characteristics includes a detected change in at least one of: a size, a shape, a hardness level, or a composition for the anatomical target;

predict a risk of an adverse event during the endoscopic procedure based on the identified anatomical target and one or more patient characteristics;

generate one or more risk mitigation strategies as part of the updated treatment plan based on predicting the risk of the adverse event; and update the predicted risk of the adverse event during the endoscopic procedure responsive to the detected change in the one or more anatomical characteristics of the calculus; and a user interface configured to;

present the identified characteristic of the anatomical target and the updated treatment plan to a user; and present human-perceptible real-time feedback on a status or progress of cannulation or navigation in reference to a navigation plan included in the updated treatment plan.

2. The endoscopic system of claim 1, further comprising:

a controller circuit configured to generate a control signal to an actuator to robotically facilitate operation of the steerable elongate instrument or a treatment tool associated therewith to treat the anatomical target in accordance with at least one of, the pre-procedure treatment plan or the updated treatment plan.

3. The endoscopic system of claim 1, wherein the processor is configured to use the at least one trained ML model to identify the anatomical target as a calculi target, and to determine a characteristic including one or more of size, shape, hardness, or composition of the calculi target, wherein the one or more characteristics include at least one of: a size, a shape, a hardness level, or a composition for the calculi target, and wherein the processor is configured to detect changes in the one or more characteristics of the calculi target during the endoscopic procedure based on a real-time spectroscopic analysis of the calculi target.

4. The endoscopic system of claim 1, wherein the processor is configured to use the at least one trained ML model to identify the anatomical target as a tissue target, and to determine a characteristic including one or more of inflammation status, level of stricture, or malignancy state of the tissue target, wherein the processor is configured to continuously monitor the one or more characteristics of the target tissue throughout the endoscopic procedure and automatically adjust one or more treatment parameters based on the detected changes in the one or more characteristics, and wherein at least one of the at least one trained ML models is trained to determine one or more settings for a treatment tool of or connected to the steerable elongate instrument based at least in part on spectroscopic data of the anatomical target or tissue proximate the anatomical target.

5. The endoscopic system of claim 1, wherein the processor is configured to use the at least one trained ML model to generate the updated treatment plan including a recommended tool of a specific type or size for use in treating the anatomical target.

6. The endoscopic system of claim 5, wherein the anatomical target includes a calculi target, and wherein the recommended tool includes one of a mechanical lithotripsy device, a laser lithotripsy device, or an electrohydraulic lithotripsy device for ablating or fragmenting the calculi target.

7. The endoscopic system of claim 5, wherein the recommended tool includes one of a balloon, a basket, or a snare for extracting the anatomical target or a portion thereof.

8. The endoscopic system of claim 5, wherein the processor is configured to determine the recommended tool further based on one or more of:

a position of the anatomical target;

spatial restrictions of an environment of the anatomical target; or sizes or geometries of candidate tools for treating the anatomical target.

9. The endoscopic system of claim 5, wherein the updated treatment plan further includes one or more operational parameters for using the recommended tool to treat the anatomical target.

10. The endoscopic system of claim 9, wherein the anatomical target includes a calculi target, and wherein the one or more operational parameters include an energy output of a lithotripsy device for ablating or fragmenting the calculi target.

11. The endoscopic system of claim 9, wherein the one or more operational parameters include a position, a heading direction, or an angle of at least a portion of the recommended tool with respect to the anatomical target.

12. The endoscopic system of claim 9, wherein the one or more operational parameters include a navigation path for navigating the steerable elongate instrument or maneuvering the recommended tool with respect to the anatomical target.

13. The endoscopic system of claim 1, wherein the anatomical target includes a calculi target, and wherein the processor is configured to use the at least one trained ML model to generate the updated treatment plan including a geometric location on the calculi target and an aiming angle or orientation of a laser lithotripsy device to direct laser energy at the geometric location to ablate or fragment the calculi target.

14. The endoscopic system of claim 1, wherein the anatomical target includes a plurality of anatomical structures to be treated, and wherein the processor is configured to use the at least one trained ML model to generate the updated treatment plan including to determine an order of treating the plurality of structures.

15. The endoscopic system of claim 1, wherein the processor is configured to:

use the at least one trained ML model to determine a probability of success or an estimate of treatment time in accordance with the updated treatment plan; and analyze time-series data representing a change in at least one of movement or deflection of the steerable elongate instrument during the endoscopic procedure and incorporate the analyzed movement data into determining a probability of success of the endoscopic procedure or an estimate of treatment time.

16. The endoscopic system of claim 1, wherein the processor is further configured to train an ML model using a training dataset comprising procedure data from past endoscopic procedures on a plurality of patients, the procedure data including (i) images of anatomical targets of the plurality of patients and (ii) identified characteristics of the anatomical targets and assessments of treatment plans for treating respective anatomical targets, and wherein the training dataset comprises procedure data from one or more past endoscopic procedures performed at one or more different medical facilities, and wherein the processor is configured to generate at least one of the pre-procedure treatment plan or the updated treatment plan based on cross-facility treatment outcome data.

17. The endoscopic system of claim 16, wherein the ML model is trained using supervised learning or unsupervised learning.

18. The endoscopic system of claim 1, wherein the anatomical target includes a plurality of targets, and wherein the user interface is configured to:

display images of the plurality of targets; and responsive to a user selection of one of the plurality of targets, display the identified characteristic of the selected target and the updated treatment plan for treating the selected target.

19. A method of identifying an anatomical target and planning an endoscopic procedure via an endoscopic system, the method comprising:

generating a pre-procedure treatment plan for treating the anatomical target prior to initiating treatment of the anatomical target;

providing patient information including real-time images of the anatomical target captured by an imaging sensor during an endoscopic procedure;

applying the real-time images of the anatomical target to at least one trained machine-learning (ML) model to (i) identify the anatomical target and a characteristic thereof, and (ii) generate, based on the identified anatomical target and the characteristic thereof, an updated treatment plan for treating the anatomical target, wherein the at least one ML model performs a real-time analysis of the real-time images to detect a change in one or more anatomical characteristics of the anatomical target and responsively automatically real-time update the updated treatment plan based on the detected change in the one or more anatomical characteristics of the anatomical target, wherein the identified anatomical target is a calculus, and wherein the detected change in the one or more anatomical characteristics includes a detected change in at least one of: a size, a shape, a hardness level, or a composition for the anatomical target;

predicting a risk of an adverse event during the endoscopic procedure based on the identified anatomical target and one or more patient characteristics;

generating one or more risk mitigation strategies as part of the updated treatment plan based on predicting the risk of the adverse event;

updating the predicted risk of the adverse event during the endoscopic procedure responsive to the detected change in the one or more anatomical characteristics of the calculus;

presenting the identified characteristic of the anatomical target and the updated treatment plan on a user interface; and presenting human-perceptible real-time feedback on a status or progress of cannulation or navigation in reference to a navigation plan included in the updated treatment plan on the user interface.

20. The method of claim 19, further comprising:

training the at least one ML model using a training dataset comprising procedure data from past endoscopic procedures on a plurality of patients, the procedure data including (i) images of anatomical targets of the plurality of patients and (ii) identified characteristics of the anatomical targets and assessments of treatment plans for treating respective anatomical targets.

* * * * *